United States Patent
Jeon et al.

(10) Patent No.: US 10,043,984 B2
(45) Date of Patent: Aug. 7, 2018

(54) CONDENSED CYCLIC COMPOUND AND ORGANIC LIGHT-EMITTING DEVICE INCLUDING THE SAME

(71) Applicants: Samsung Electronics Co., Ltd., Suwon-si, Gyeonggi-do (KR); Samsung SDI Co., Ltd., Yongin-si, Gyeonggi-do (KR)

(72) Inventors: Soonok Jeon, Seoul (KR); Sangmo Kim, Hwaseong-si (KR); Hyungjun Kim, Suwon-si (KR); Yeonsook Chung, Seoul (KR); Yongsik Jung, Yongin-si (KR); Miyoung Chae, Suwon-si (KR); Dalho Huh, Suwon-si (KR); Joonghyuk Kim, Seoul (KR); Sooghang Ihn, Hwaseong-si (KR)

(73) Assignees: SAMSUNG ELECTRONICS CO., LTD., Gyeonggi-Do (KR); SAMSUNG SDI CO., LTD., Gyeonggi-Do (KR)

(*) Notice: Subject to any disclaimer, the term of this patent is extended or adjusted under 35 U.S.C. 154(b) by 180 days.

(21) Appl. No.: 14/969,257

(22) Filed: Dec. 15, 2015

(65) Prior Publication Data

US 2017/0005275 A1    Jan. 5, 2017

(30) Foreign Application Priority Data

Jul. 1, 2015 (KR) .................. 10-2015-0094004
Aug. 17, 2015 (KR) .................. 10-2015-0115420

(51) Int. Cl.
| | |
|---|---|
| *H01L 51/00* | (2006.01) |
| *C07D 401/10* | (2006.01) |
| *C09K 11/02* | (2006.01) |
| *C09K 11/06* | (2006.01) |
| *H01L 51/50* | (2006.01) |

(52) U.S. Cl.
CPC ........ *H01L 51/0072* (2013.01); *C07D 401/10* (2013.01); *C09K 11/025* (2013.01); *C09K 11/06* (2013.01); *H01L 51/0061* (2013.01); *C09K 2211/1007* (2013.01); *C09K 2211/1022* (2013.01); *C09K 2211/1044* (2013.01); *C09K 2211/185* (2013.01); *H01L 51/0085* (2013.01); *H01L 51/0087* (2013.01); *H01L 51/5004* (2013.01); *H01L 51/5016* (2013.01); *H01L 2251/552* (2013.01)

(58) Field of Classification Search
CPC .... C07D 401/10; C09K 11/025; C09K 11/06; C09K 2211/1007; C09K 2211/1022; C09K 2211/1044; C09K 2211/185; H01L 51/0072; H01L 51/009; H01L 51/0061; H01L 51/0071
See application file for complete search history.

(56) References Cited

U.S. PATENT DOCUMENTS

| | | | |
|---|---|---|---|
| 2010/0155706 A1* | 6/2010 | Yu | C07D 213/38 257/40 |
| 2012/0319052 A1* | 12/2012 | Brocke | C07D 401/04 252/500 |
| 2014/0158999 A1* | 6/2014 | Jung | C09K 11/06 257/40 |
| 2014/0252318 A1* | 9/2014 | Boudreault | H01L 51/0094 257/40 |
| 2016/0133856 A1* | 5/2016 | Yang | H01L 51/0072 257/40 |
| 2016/0181546 A1* | 6/2016 | Kang | H01L 51/0072 257/40 |

FOREIGN PATENT DOCUMENTS

| | | |
|---|---|---|
| JP | 2011256143 A | 12/2011 |
| KR | 1020130118269 A | 10/2013 |
| KR | 1020140071732 A | 6/2014 |
| WO | 2013108589 A1 | 7/2013 |

* cited by examiner

*Primary Examiner* — Anca Eoff
(74) *Attorney, Agent, or Firm* — Cantor Colburn LLP

(57) ABSTRACT

A condensed cyclic compound represented by Formula 1, comprising at least one cyano (—CN) group:

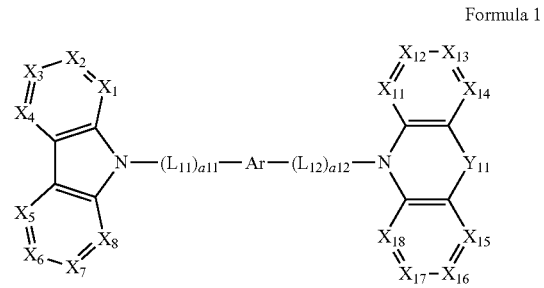

Formula 1 wherein, in Formula 1, groups and variables are the same as described in the specification.

20 Claims, 4 Drawing Sheets

CONDENSED CYCLIC COMPOUND AND ORGANIC LIGHT-EMITTING DEVICE INCLUDING THE SAME

CROSS-REFERENCE TO RELATED APPLICATIONS

This application claims priority to and the benefit of Korean Patent Application No. 10-2015-0094004, filed on Jul. 1, 2015, and Korean Patent Application No, 10-2015-0115420, filed on Aug. 17, 2015, in the Korean Intellectual Property Office, the contents of which are incorporated herein in their entirety by reference.

BACKGROUND

1. Field

The present disclosure relates to a condensed cyclic compound and an organic light-emitting device including the same.

2. Description of the Related Art

Organic light-emitting devices (OLEDs) are self-emitting devices that have wide viewing angles, high contrast, and quick response times. In addition, the OLEDs exhibit high brightness, low driving voltage characteristics, and can provide multicolored images.

A typical organic light-emitting device may include an anode, a cathode and an organic layer that is disposed between the anode and the cathode, wherein the organic layer includes an emission layer. A hole transport region may be disposed between the anode and the emission layer, and an electron transport region may be disposed between the emission layer and the cathode. Holes injected from the anode move to the emission layer via the hole transport region, while electrons injected from the cathode move to the emission layer via the electron transport region. Carriers, e.g., the holes and the electrons, recombine in the emission layer to generate excitons. When the excitons drop from an excited state to a ground state, light is emitted.

Different types of organic light emitting devices are known. However, there still remains a need in OLEDs having low driving voltage, high efficiency, high brightness, and long lifespan.

SUMMARY

Provided are a novel condensed cyclic compound and an organic light-emitting device including the same.

Additional aspects will be set forth in part in the description which follows and, in part, will be apparent from the description, or may be learned by practice of the presented exemplary embodiments.

According to an aspect of an exemplary embodiment, there is provided a condensed cyclic compound represented by Formula 1, including at least one cyano (—CN) group:

Formula 1

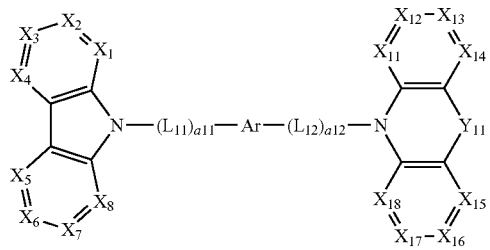

In Formula 1, $X_1$ may be N or $C(R_1)$, $X_2$ may be N or $C(R_2)$, $X_3$ may be N or $C(R_3)$, $X_4$ may be N or $C(R_4)$, $X_5$ may be N or $C(R_5)$, $X_6$ may be N or $C(R_6)$, $X_7$ may be N or $C(R_7)$, $X_8$ may be N or $C(R_8)$, $X_{11}$ may be N or $C(R_{11})$, $X_{12}$ may be N or $C(R_{12})$, $X_{13}$ may be N or $C(R_{13})$, $X_{14}$ may be N or $C(R_{14})$, $X_{15}$ may be N or $C(R_{15})$, $X_{16}$ may be N or $C(R_{16})$, $X_{17}$ may be N or $C(R_{17})$, and $X_{18}$ may be N or $C(R_{18})$, $Y_{11}$ may be O, S, $C(R_{101})(R_{102})$, or $Si(R_{101})(R_{102})$, $R_1$ to $R_8$, $R_{11}$ to $R_{18}$, $R_{101}$, and $R_{102}$ may each be independently selected from:

a hydrogen, a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{50}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, and —$Si(Q_1)(Q_2)(Q_3)$, wherein the substituted or unsubstituted monovalent non-aromatic condensed heteropolycyclic group does not include a substituted or unsubstituted carbazolyl group, and $R_{101}$ and $R_{102}$ may be optionally linked to each other to form a saturated or unsaturated ring, Ar may be a group represented by one of Formulae 2A to 2D:

Formula 2A

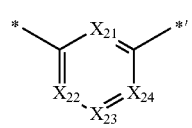

Formula 2B

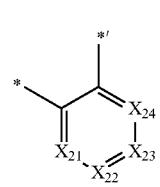

Formula 2C

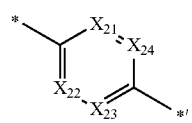

Formula 2D

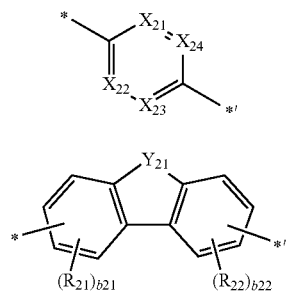

wherein, in Formulae 2A to 2D,

* and *' may each independently indicate a binding site to a neighboring atom, $X_{21}$ may be N or $C(R_{21})$, $X_{22}$ may be N or $C(R_{22})$, $X_{23}$ may be N or $C(R_{23})$, and $X_{24}$ may be N or $C(R_{24})$, $Y_{21}$ may be O, S, $P(=O)_2$, Se, $C(R_{25})(R_{26})$, or $Si(R_{25})(R_{26})$, $R_{21}$ to $R_{25}$ may each be independently selected from a hydrogen, a deuterium, a $C_1$-$C_4$ alkyl group, a $C_5$-$C_{20}$ aryl group, a $C_1$-$C_{20}$ heteroaryl group, and —$Si(Q_{11})(Q_{12})(Q_{13})$, and b21 and b22 may each be independently selected from integers of 1 to 3, provided that when b21 is 2 or more, groups $R_{21}$ may be identical to or different from each other, and provided that when b22 is 2 or more, groups $R_{22}$ may be identical to or different from each other, $L_{11}$ and $L_{12}$ may each be independently selected from:

a phenylene group, a pyridinylene group, a pyrimidinylene group, a pyrazinylene group, a pyridazinylene group, a triazinylene group, a dibenzofuranylene group, a dibenzothiophenylene group, and a dibenzosilolylene group; and a phenylene group, a pyridinylene group, a pyrimidinylene group, a pyrazinylene group, a pyridazinylene group, a triazinylene group, a dibenzofuranylene group and a dibenzothiophenylene group, each substituted with at least one of a deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —$Si(Q_{21})(Q_{22})(Q_{23})$.

a11 and a12 may each be independently selected from 0, 1, 2, 3, 4, and 5, provided that when a11 is 2 or more, groups $L_{11}$ may be identical to or different from each other, and provided that when a12 is 2 or more, groups $L_{12}$ may be identical to or different from each other, and $Q_1$ to $Q_3$, $Q_{11}$ to $Q_{13}$, $Q_{21}$ to $Q_{23}$, and $Q_{31}$ to $Q_{33}$ may each be independently selected from a hydrogen, a $C_1$-$C_{60}$ alkyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic condensed heteropolycyclic group, provided that the monovalent non-aromatic condensed heteropolycyclic group does not include a carbazolyl group.

According to an aspect of another exemplary embodiment, there is provided an organic light-emitting device including:

a first electrode;

a second electrode; and an organic layer disposed between the first electrode and the second electrode, wherein the organic layer includes an emission layer and at least one condensed cyclic compound of Formula 1.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
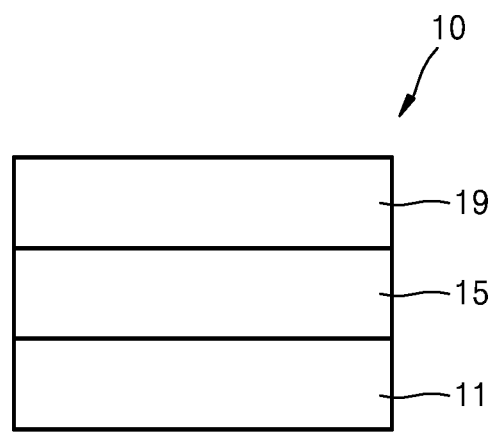
FIG. 1 is a schematic cross-sectional view of a structure of an organic light-emitting device according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

There is provided a condensed cyclic compound represented by Formula 1, including at least one cyano (—CN) group:

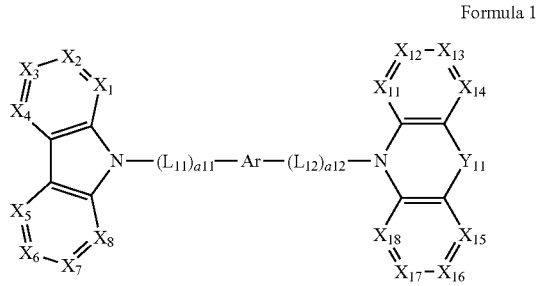

Formula 1

In Formula 1, at least one of a group represented by

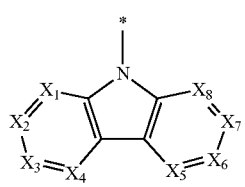

and a group represented by

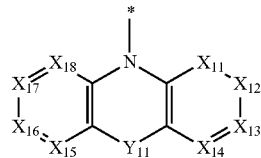

may include at least one cyano (—CN) group.

In an exemplary embodiment, at least one of $X_1$ to $X_8$ in Formula 1 may be C(CN), but embodiments are not limited thereto.

In another exemplary embodiment, at least one of $X_{11}$ to $X_{18}$ in Formula 1 may be C(CN), but embodiments are not limited thereto.

In another exemplary embodiment, $Y_{11}$ in Formula 1 may be a group including a cyano (—CN) group, but embodiments are not limited thereto.

In Formula 1, $X_1$ may be N or $C(R_1)$, $X_2$ may be $C(R_2)$, $X_3$ may be N or $C(R_3)$, $X_4$ may be $C(R_4)$, $X_5$ may be $C(R_5)$, $X_6$ may be N or $C(R_6)$, $X_7$ may be N or $C(R_7)$, $X_8$ may be N or $C(R_8)$, $X_{11}$ may be N or $C(R_{11})$, $X_{12}$ may be $C(R_{12})$, $X_{13}$ may be N or $C(R_{13})$, $X_{14}$ may be $C(R_{14})$, $X_{15}$ may be $C(R_{15})$, $X_{16}$ may be N or $C(R_{16})$, $X_{17}$ may be N or $C(R_{17})$, and $X_{18}$ may be N or $C(R_{18})$, and descriptions of $R_1$ to $R_{16}$ may be each independently as referred to in the descriptions thereof in the present specification.

In an exemplary embodiment, in Formula 1, $X_1$ may be N, $X_2$ may be $C(R_2)$, $X_3$ may be $C(R_3)$, $X_4$ may be $C(R_4)$, $X_5$ may be $C(R_5)$, $X_6$ may be $C(R_6)$, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but embodiments are not limited thereto.

In an exemplary embodiment, in Formula 1, $X_1$ may be $C(R_1)$, $X_2$ may be N, $X_3$ may be $C(R_3)$, $X_4$ may be $C(R_4)$, $X_5$ may be $C(R_5)$, $X_6$ may be $C(R_6)$, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but embodiments are not limited thereto.

In an exemplary embodiment, in Formula 1, $X_1$ may be $C(R_1)$, $X_1$ may be $C(R_2)$, $X_3$ may be N, $X_4$ may be $C(R_4)$, $X_5$ may be $C(R_5)$, $X_6$ may be $C(R_6)$, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{15})$, $X_{17}$ may be $C(R_{17})$, and $X_{18}$ may be $C(R_{18})$, but embodiments are not limited thereto.

In another exemplary embodiment, in Formula 1, $X_1$ may be $C(R_1)$, $X_2$ may be $C(R_2)$, $X_3$ may be $C(R_3)$, $X_4$ be N, $X_5$ may be $C(R_5)$, $X_6$ may be $C(R_6)$, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but embodiments are not limited thereto.

In another exemplary embodiment, in Formula 1, $X_1$ may be $C(R_1)$, $X_2$ may be $C(R_2)$, $X_3$ may be $C(R_3)$, $X_4$ may be $C(R_4)$, $X_5$ may be N, $X_6$ may be $C(R_6)$, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but embodiments are not limited thereto.

In another exemplary embodiment, in Formula 1, $X_1$ may be $C(R_1)$, $X_2$ may be $C(R_2)$, $X_3$ may be $C(R_3)$, $X_4$ may be $C(R_4)$, $X_5$ may be $C(R_5)$, $X_6$ may be N, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but embodiments are not limited thereto.

In another exemplary embodiment, in Formula 1, $X_1$ may be $C(R_1)$, $X_2$ may be $C(R_2)$, $X_3$ may be $C(R_3)$, $X_4$ may be $C(R_4)$, $X_5$ may be $C(R_5)$, $X_6$ may be $C(R_6)$, $X_7$ may be N, $X_8$ may be $C(R_8)$, $X_{11}$ may be $C(R_{11})$. $X_{12}$ may be $C(R_{12})$, $X_{13}$ may be $C(R_{13})$, may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but embodiments are not limited thereto.

In another exemplary embodiment, in Formula 1, $X_1$ may be $C(R_1)$, $X_2$ may be $C(R_2)$, $X_3$ may be $C(R_3)$, $X_4$ may be $C(R_4)$, $X_5$ may be $C(R_5)$, $X_6$ may be $C(R_5)$, $X_7$ may be $C(R_7)$, $X_8$ may be N, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but embodiments are not limited thereto.

In another exemplary embodiment, in Formula 1, $X_1$ may be $C(R_1)$, $X_2$ may be $C(R_2)$, $X_3$ may be $C(R_3)$, $X_4$ may be $C(R_4)$, $X_5$ may be $C(R_5)$, $X_5$ may be $C(R_6)$, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{18})$, $X_{17}$ may be $C(R_{17})$, and $X_{18}$ may be $C(R_{18})$, but embodiments are not limited thereto.

In an exemplary embodiment, in Formula 1, $Y_{11}$ may be O, S, $C(R_{101})(R_{102})$, or $Si(R_{101})(R_{102})$. Descriptions of $R_{101}$ and $R_{102}$ may be each independently as referred to in the descriptions thereof in the present specification.

In Formula 1, $Y_{11}$ may be $C(R_{101})(R_{102})$, but $Y_{11}$ is not limited thereto.

In Formula 1, $R_1$ to $R_8$, $R_{11}$ to $R_{18}$, $R_{101}$, and $R_{102}$ may each be independently selected from:

a hydrogen, a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{80}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{13}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, and —$Si(Q_1)(Q_2)(Q_3)$, wherein the substituted or unsubstituted monovalent non-aromatic condensed heteropolycyclic group does not include a substituted or an unsubstituted carbazolyl group, and $R_{101}$ and $R_{102}$ may be optionally linked to each other to form a saturated or unsaturated ring.

In an exemplary embodiment, in Formula 1, $R_1$ to $R_8$, $R_{11}$ to $R_{18}$, $R_{101}$, and $R_{102}$ may each be independently selected from:

a hydrogen, a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one of a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, a pyrimidinyl group, a pyrazinyl group, a pyridazinyl group, and a triazinyl group, a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyndinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazotyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyridimidinyl group, and an imidazopyridinyl group, a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyridimidinyl group, and an imidazopyridinyl group, each substituted with at least one of a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, and —Si($Q_{31}$)($Q_{32}$)($Q_{33}$), and —Si($Q_1$)($Q_2$)($Q_3$), wherein $R_{11})_1$ and $R_{102}$ may be optionally linked to each other to form a saturated or unsaturated ring, and $Q_1$ to $Q_3$ and $Q_{31}$ to $Q_{33}$ may each be independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cinnolinyl group, and a quinazolinyl group, but embodiments are not limited thereto.

In another exemplary embodiment, in Formula 1, $R_1$ to $R_8$, $R_{11}$ to $R_{18}$, $R_{101}$, and $R_{102}$ may each be independently selected from:

a hydrogen, a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a phenyl group, a naphthyl group, a pyridinyl group, a pyrimidinyl group, a pyrazinyl group, a pyridazinyl group, and a triazinyl group;

a phenyl group, a naphthyl group, a pyridinyl group, a pyrimidinyl group, a pyrazinyl group, a pyridazinyl group, and a triazinyl group, each substituted with at least one of a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —Si($Q_{31}$)($Q_{32}$)($Q_{33}$); and —Si($Q_1$)($Q_2$)($Q_3$), wherein $R_{101}$ and $R_{102}$ may be optionally linked to each other to form a saturated or unsaturated ring, and $Q_1$ to $Q_3$ and $Q_{31}$ to $Q_{33}$ may each be independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, and a triazinyl group, but embodiments are not limited thereto.

In another exemplary embodiment, in Formula 1, $R_1$ to $R_8$, $R_{11}$ to $R_{18}$, $R_{101}$, and $R_{102}$ may each be independently selected from:

a hydrogen, a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a methyl group, an ethyl group, an n-propyl group, an iso-propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a phenyl group, a naphthyl group, a pyridinyl group, a pyrimidinyl group, and a triazinyl group;

a methyl group, an ethyl group, an n-propyl group, an iso-propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a phenyl group, a naphthyl group, a pyridinyl group, a pyrimidinyl group, and a triazinyl group, each substituted with at least one of a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, and a phosphoric acid group or a salt thereof; and —Si($Q_1$)($Q_2$)($Q_3$), wherein $R_{101}$ and $R_{102}$ may be optionally linked to each other to form a saturated or unsaturated ring, and $Q_1$ to $Q_3$ may each be independently selected from a hydrogen, a $C_1$-$C_{10}$ alkyl group, a $C_1$-$C_{10}$ alkoxy group, and a phenyl group, but embodiments are not limited thereto.

In another exemplary embodiment, in Formula 1, $R_1$ to $R_8$ and $R_{11}$ to $R_{18}$ may each be independently selected from a hydrogen, a deuterium, a cyano (—CN) group, a methyl group, an ethyl group, an n-propyl group, an iso-propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, and —Si($Q_1$)($Q_2$)($Q_3$), wherein $Q_1$ to $Q_3$ may each be independently selected from a hydrogen, a $C_1$-$C_{10}$ alkyl group, a $C_1$-$C_{10}$ alkoxy group, and a phenyl group, but embodiments are not limited thereto.

In another exemplary embodiment, in Formula 1, $R_{101}$ and $R_{102}$ may each be independently selected from:

a methyl group, an ethyl group, an n-propyl group, an iso-propyl group, an n-butyl group, an isobutyl group, a sec-butyl group, a tert-butyl group, a phenyl group, and a naphthyl group; and a methyl group substituted with a cyano (—CN) group, an ethyl group, an n-propyl group, an iso-propyl group, an n-butyl group, an isobutyl group, a sec-butyl group, a tert-butyl group, a phenyl group, and a naphthyl group, but embodiments are not limited thereto.

In another exemplary embodiment, in Formula 1, $R_{101}$ and $R_{102}$ may be linked to each other to form a group represented by Formula 8, but embodiments are not limited thereto:

Formula 8

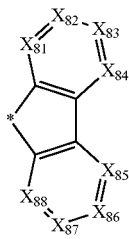

In Formula 8,

\* may indicate a carbon atom included in $Y_{11}$ of Formula 1, $X_{81}$ may be N or $C(R_{81})$, $X_{82}$ may be $C(R_{82})$, $X_{83}$ may be N or $C(R_{83})$, $X_{84}$ may be $C(R_{84})$, $X_{88}$ may be $C(R_{88})$, $X_{86}$ may be N or $C(R_{88})$, $X_{87}$ may be N or $C(R_{87})$, and $X_{88}$ may be N or $C(R_{88})$, and $R_{81}$ to $R_{88}$ may each be independently selected from a hydrogen, a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —$Si(Q_{31})(Q_{32})(Q_{33})$, wherein $Q_{31}$ to $Q_{33}$ may each be independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, and a triazinyl group.

In another exemplary embodiment, in Formula 1, $R_{101}$ and $R_{102}$ may be linked to each other to form a group represented by Formula 9, but embodiments are not limited thereto:

Formula 9

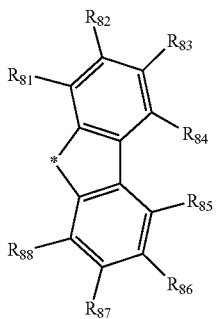

In Formula 9,

\* may indicate a carbon atom included in $Y_{11}$ of Formula 1, $R_{81}$ to $R_{88}$ may each be independently selected from a hydrogen, a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —$Si(Q_{31})(Q_{32})(Q_{33})$, wherein $Q_{31}$ to $Q_{33}$ may each be independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, and a triazinyl group.

In another exemplary embodiment, in Formula 1, $R_{101}$ and $R_{102}$ may be linked to each other to form a group represented by one of Formulae 10-1 and 10-2, but embodiments are not limited thereto:

10-1

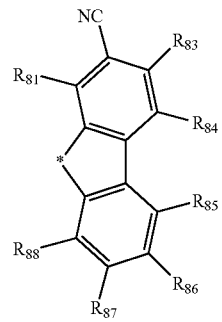

10-2

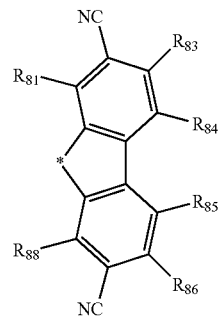

In Formulae 10-1 and 10-2,

\* may indicate a carbon atom included in $Y_{11}$ of Formula 1, $R_{91}$ to $R_{98}$ may each be independently selected from a hydrogen, a deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —$Si(Q_{31})(Q_{32})(Q_{33})$, wherein $Q_{31}$ to $Q_{33}$ may each be independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, and a triazinyl group.

In an exemplary embodiment, at least one of $X_1$ to $X_8$ and $X_{11}$ to $X_{18}$ in Formula 1 may be C(CN).

In another exemplary embodiment, at least one of $X_3$, $X_8$, $X_{13}$, and $X_{18}$ in Formula 1 may be C(CN), but embodiments are not limited thereto.

In another exemplary embodiment, at least one of $R_1$, $R_2$, $R_4$, $R_5$, $R_7$, $R_8$, $R_{11}$, $R_{12}$, $R_{14}$, $R_{15}$, $R_{17}$, and $R_{18}$ in Formula 1 may not be a cyano (—CN) group, but embodiments are not limited thereto.

In Formula 1, Ar may be a group represented by one of Formulae 2A to 2C:

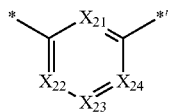
Formula 2A

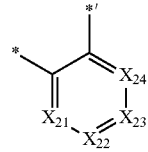
Formula 2B

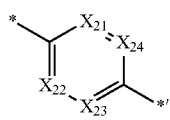
Formula 2C

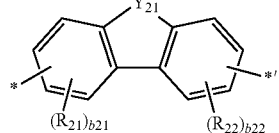
Formula 2D

In Formulae 2A to 2D,

* and *' may each independently indicate a binding site to a neighboring atom, $X_{21}$ may be N or $C(R_{21})$, $X_{22}$ may be N or $C(R_{22})$, $X_{23}$ may be N or $C(R_{23})$, and $X_{24}$ may be $C(R_{24})$, $Y_{21}$ may be O, S, P(=O)$_2$, Se, $C(R_{25})(R_{25})$, or $Si(R_{25})(R_{25})$, $R_{21}$ to $R_{26}$ may each be independently selected from a hydrogen, a deuterium, a $C_1$-$C_4$ alkyl group, a $C_6$-$C_{20}$ aryl group, a $C_1$-$C_{20}$ heteroaryl group, and —$Si(Q_{11})(Q_{12})(Q_{13})$, and b21 and b22 may each be independently selected from integers of 1 to 3, provided that when b21 is 2 or more, groups $R_{21}$ may be identical to or different from each other, and provided that when b22 is 2 or more, groups $R_{22}$ may be identical to or different from each other.

In another exemplary embodiment, Ar in Formula 1 may be a group represented by one of Formulae 2-1 to 2-28, but embodiments are not limited thereto:

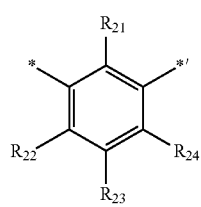
2-1

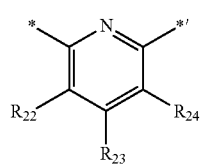
2-2

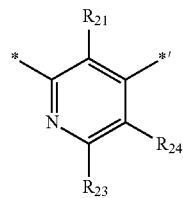
2-3

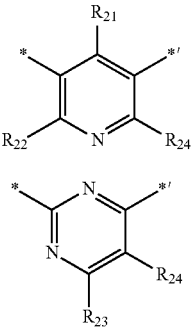
2-4

2-5

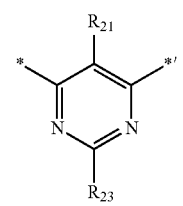
2-6

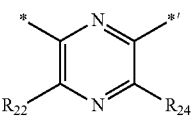
2-7

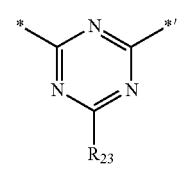
2-8

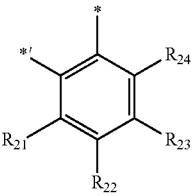
2-9

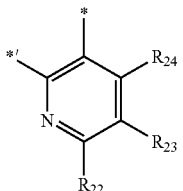
2-10

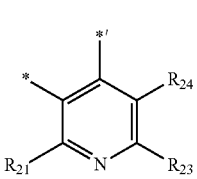
2-11

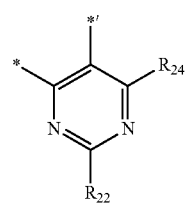 2-12
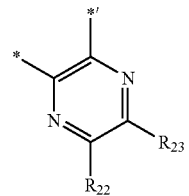 2-13
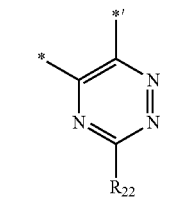 2-14
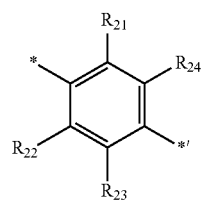 2-15
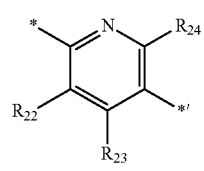 2-16
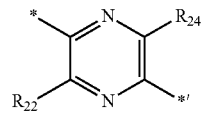 2-17
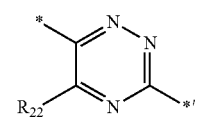 2-18
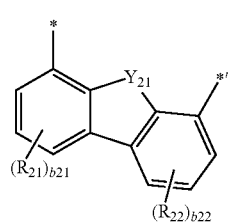 2-19
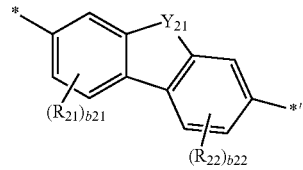 2-20
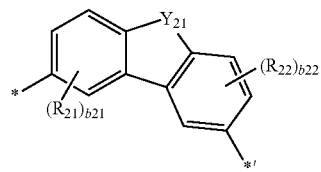 2-21
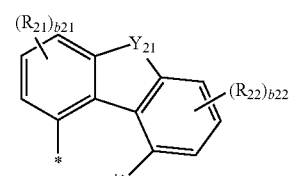 2-22
2-23
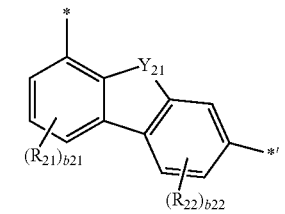 2-24
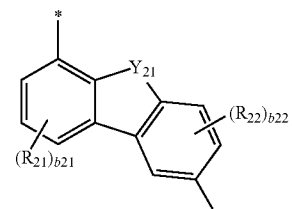 2-25
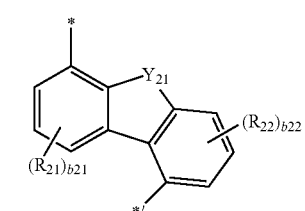 2-26
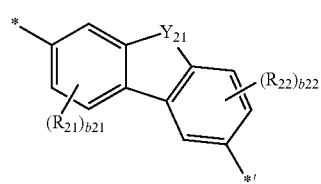 2-27

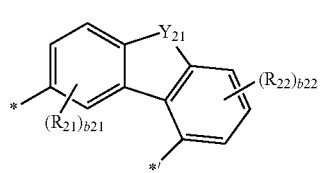

2-28

In Formulae 2-1 to 2-28, $Y_{21}$ may be O or S, $R_{21}$ to $R_{24}$ may each be independently selected from a hydrogen, a deuterium, a methyl group, an ethyl group, an n-propyl group, an iso-propyl group, an n-butyl group, an isobutyl group, a sec-butyl group, a tert-butyl group, a phenyl group, a pyridinyl group, a pyrimidinyl group, a pyrazinyl group, a pyridazinyl group, a triazinyl group, and $-Si(Q_{11})(Q_{12})(Q_{13})$, wherein $Q_{11}$ to $Q_{13}$ may each be independently selected from a hydrogen, a $C_1$-$C_{10}$ alkyl group, a $C_1$-$C_{10}$ alkoxy group, and a phenyl group, b21 and b22 may each be independently selected from 1, 2, and 3, and

* and *' may each independently indicate a binding site to a neighboring atom.

In another exemplary embodiment, Ar in Formula 1 may be a group represented by one of Formulae 2-1 to 2-4, 2-9 to 2-11, and 2-17 above, but embodiments are not limited thereto.

In Formula 1, $L_{11}$ and $L_{12}$ may each be independently selected from:

a phenylene group, a pyridinylene group, a pyrimidinylene group, a pyrazinylene group, a pyridazinylene group, a triazinylene group, a dibenzofuranylene group, a dibenzothiophenylene group, and a dibenzosilolyl group; and a phenylene group, a pyridinylene group, a pyrimidinylene group, a pyrazinylene group, a pyridazinylene group, a triazinylene group, a dibenzofuranylene group, a dibenzothiophenylene group, each substituted with at least one of a deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{13}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and $-Si(Q_{21})(Q_{22})(Q_{23})$.

In an exemplary embodiment, $L_{11}$ and $L_{12}$ in Formula 1 may each be independently selected from:

a phenylene group, a pyridinylene group, a pyrimidinylene group, a pyrazinylene group, a pyridazinylene group, a triazinylene group, a dibenzofuranylene group, and a dibenzothiophenylene group; and a phenylene group, a pyridinylene group, a pyrimidinylene group, a pyrazinylene group, a pyridazinylene group, a triazinylene group, a dibenzofuranylene group, and a dibenzothiophenylene group, each substituted with at least one of a deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and $-Si(Q_{21})(Q_{22})(Q_{23})$, but embodiments are not limited thereto.

In another exemplary embodiment, $L_{11}$ and $L_{12}$ in Formula 1 may each be independently selected from:

a phenylene group, a pyridinylene group, a pyrimidinylene group, and a triazinylene group; and a phenylene group, a pyridinylene group, a pyrimidinylene group, and a triazinylene group, each substituted with at least one of a deuterium, a methyl group, an ethyl group, an n-propyl group, an iso-propyl group, an n-butyl group, an isobutyl group, a sec-butyl group, a tert-butyl group, a phenyl group, a pyridinyl group, a pyrimidinyl group, a pyrazinyl group, a pyridazinyl group, a triazinyl group, and $-Si(Q_{21})(Q_{22})(Q_{23})$, but embodiments are not limited thereto.

In Formula 1, a11 indicates the number of $L_{11}$, and may be selected from 0, 1, 2, 3, 4, and 5. When a11 is 2 or more, groups $L_{11}$ may be identical to or different from each other.

In Formula 1, a12 indicates the number of $L_{12}$, and may be selected from 0, 1, 2, 3, 4, and 5. When a12 is 2 or more, groups $L_{12}$ may be identical to or different from each other.

In an exemplary embodiment, a11 and a12 in Formula 1 may each be independently 0 or 1, but embodiments are not limited thereto.

In another exemplary embodiment, in Formula 1, $L_{11}$ and $L_{12}$ may each be independently selected from:

a phenylene group; and a phenylene group substituted with at least one of a deuterium, a methyl group, an ethyl group, an n-propyl group, an iso-propyl group, an n-butyl group, an isobutyl group, a sec-butyl group, a tert-butyl group, a phenyl group, a pyridinyl group, a pyrimidinyl group, a pyrazinyl group, a pyridazinyl group, a triazinyl group, and $-Si(Q_{21})(Q_{22})(Q_{23})$, wherein $Q_{21}$ to $Q_{23}$ may each be independently selected from a hydrogen, a $C_1$-$C_{10}$ alkyl group, a $C_1$-$C_{10}$ alkoxy group, and a phenyl group, and a11 and a12 may each be independently 0 or 1, but embodiments are not limited thereto.

In another exemplary embodiment, in Formula 1, $L_{11}$ and $L_{12}$ may each independently a group represented by one of Formulae 3-1 to 3-3, and a11 and a12 may each be independently 0 or 1, but embodiments are not limited thereto:

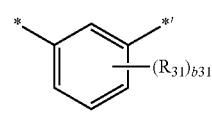

3-1

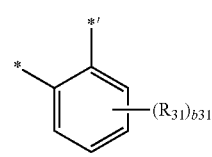

3-2

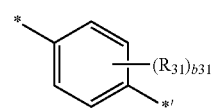

3-3

In Formulae 3-1 to 3-3, $R_{31}$ may be selected from a hydrogen, a deuterium, a methyl group, an ethyl group, an n-propyl group, an iso-propyl group, an n-butyl group, an isobutyl group, a sec-butyl group, a tert-butyl group, a phenyl group, a pyridinyl group, a pyrimidinyl group, a pyrazinyl group, a pyridazinyl group, a triazinyl group, and $-Si(Q_{21})(Q_{22})(Q_{23})$, wherein $Q_{21}$ to $Q_{23}$ may each be independently selected from a hydrogen, a $C_1$-$C_{10}$ alkyl group, a $C_1$-$C_{13}$ alkoxy group, and a phenyl group, b31 may be selected from 1, 2, 3, and 4, and

* and *' may each independently indicate a binding site to a neighboring atom.

For example, in Formula 1, Ar may be a group represented by one of Formulae 2A, 2B, and 2C, and a sum of a11 and a12 (a11+a12) may not be 0, but embodiments are not limited thereto.

In another exemplary embodiment, in Formula 1, Ar may be a group represented by Formula 2D above, and a sum of a11 and a12 (a11+a12) may be 0, but embodiments are not limited thereto.

In Formula 1, *-$(L_{11})_{a11}$-Ar-$(L_{12})_{a12}$-*' may be a group represented by one of Formulae 4-1 to 4-19, but *-$(L_{11})_{a11}$-Ar-$(L_{12})_{a12}$-*' is not limited thereto:

4-1
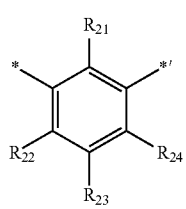

4-2
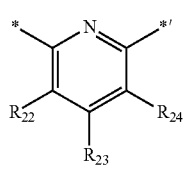

4-3
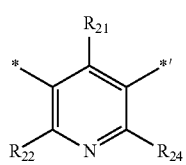

4-4
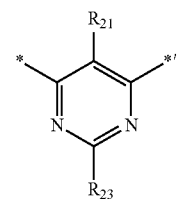

4-5
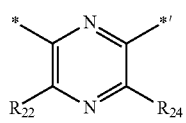

4-6
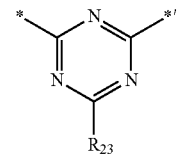

-continued 4-7
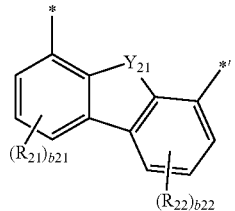

4-8
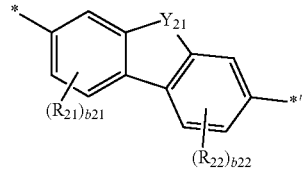

4-9
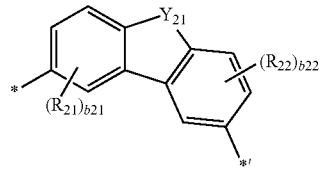

4-10
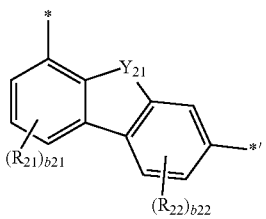

4-11
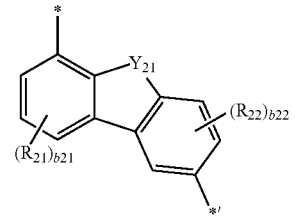

4-12
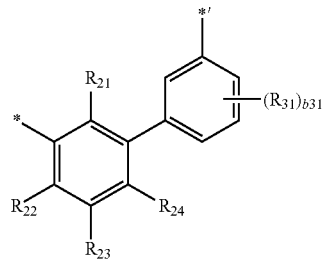

4-13
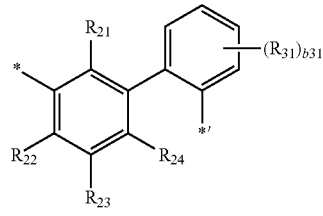

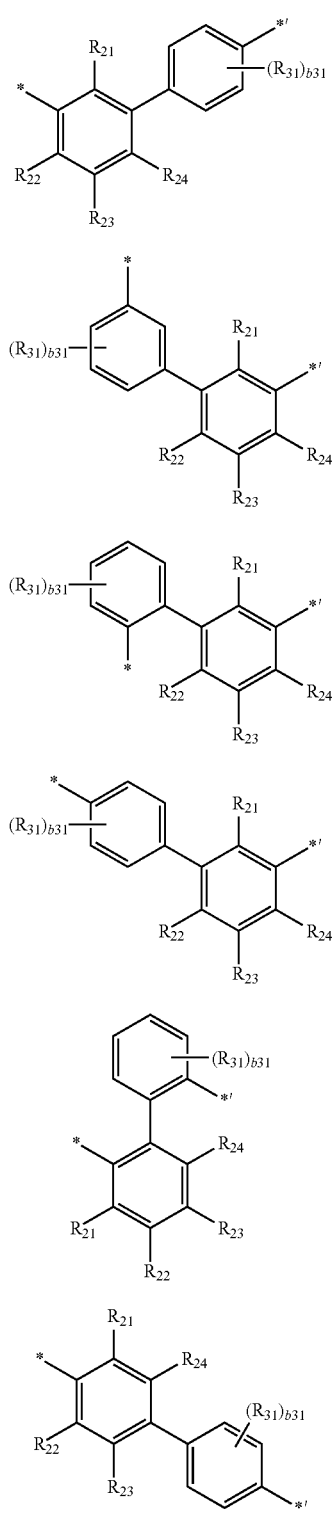

In Formulae 4-1 to 4-19,

Y$_{21}$ may be O or S,

R$_{21}$ to R$_{24}$ and R$_{31}$ may each be independently selected from a hydrogen, a deuterium, a methyl group, an ethyl group, an n-propyl group, an iso-propyl group, an n-butyl group, an isobutyl group, a sec-butyl group, a tert-butyl group, a phenyl group, a pyridinyl group, a pyrimidinyl group, a pyrazinyl group, a pyridazinyl group, a triazinyl group, and —Si(Q$_{21}$)(Q$_{22}$)(Q$_{23}$), wherein Q$_{21}$ to Q$_{23}$ may each be independently selected from a hydrogen, a C$_1$-C$_{10}$ alkyl group, a C$_1$-C$_{10}$ alkoxy group, and a phenyl group, b21 and b22 may each be independently selected from 1, 2, and 3, b31 may be selected from 1, 2, 3, and 4, and \* and \*' may each independently indicate a binding site to a neighboring atom.

The condensed cyclic compound of Formula 1 may be represented by one of Formulae 1-1 to 1-15, but the condensed cyclic compound of Formula 1 is not limited thereto:

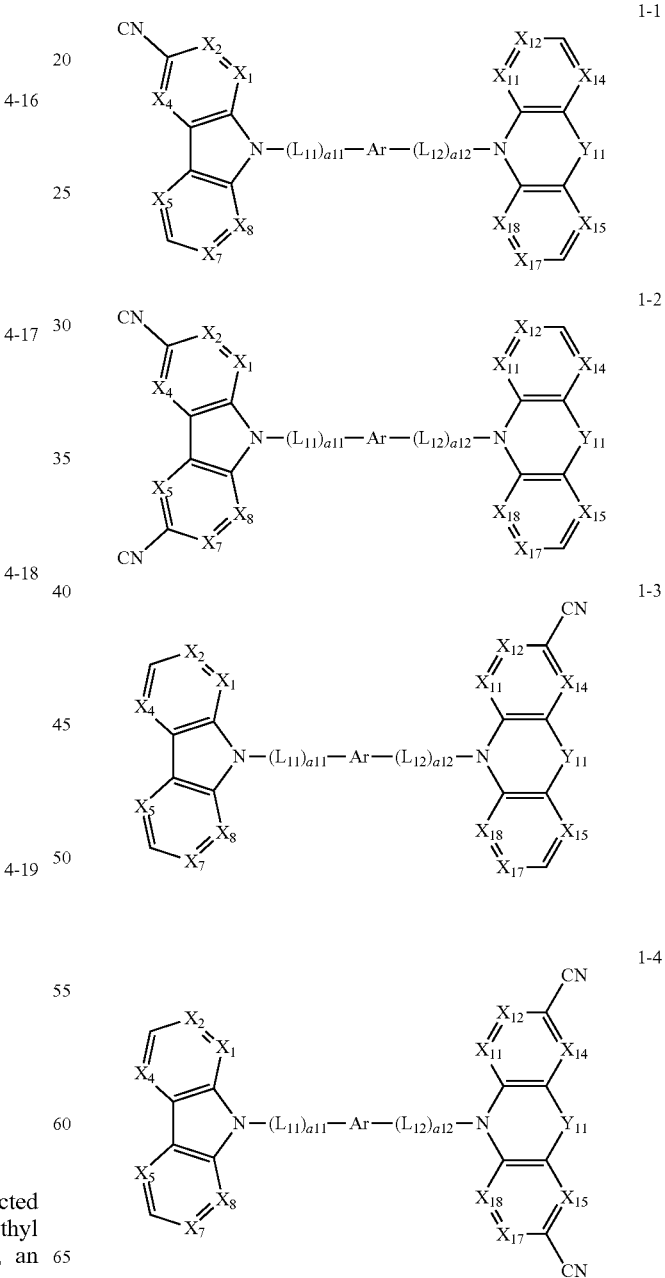

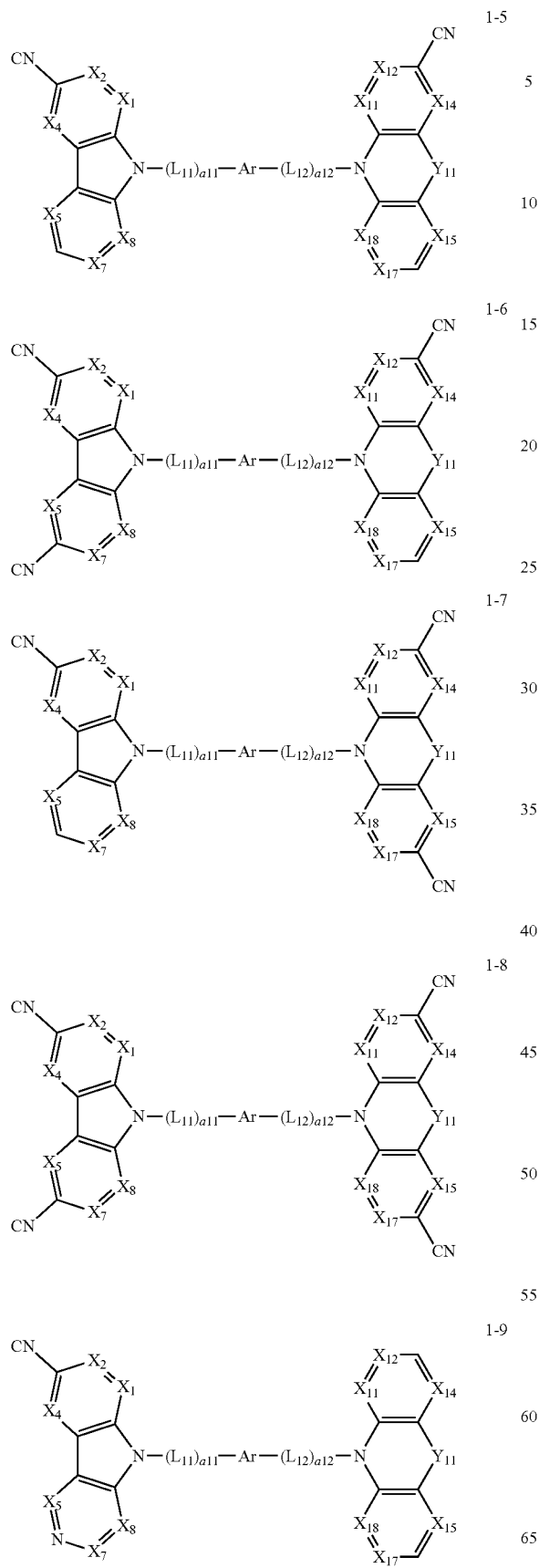

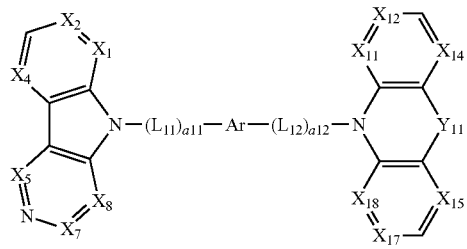

1-15

In Formulae 1-1 to 1-15, descriptions of $X_1$, $X_2$, $X_4$, $X_5$, $X_7$, $X_8$, $X_{11}$, $X_{12}$, $X_{14}$, $X_{15}$, $X_{17}$, $X_{17}$, $Y_{11}$, Ar, $L_{11}$, $L_{12}$, a11, and a12 may each be independently as referred to in the descriptions provided in connection with Formula 1.

In an exemplary embodiment, in Formulae 1-1 to 1-15, $X_1$ may be N, $X_2$ may be $C(R_2)$, $X_4$ may be $C(R_4)$, $X_5$ may be $C(R_5)$, $X_7$ may be $C(R_7)$, $X_8$ may be $C(R_8)$, $X_{11}$ may be $C(R_{11})$, $X_{12}$ may be $C(R_{12})$, $X_{14}$ may be $C(R_{14})$, $X_{15}$ may be $C(R_{15})$, $X_{17}$ may be $C(R_{17})$, and $X_{18}$ may be $C(R_{18})$, $X_1$ may be $C(R_1)$, $X_2$ may be N, $X_4$ may be $C(R_4)$, $X_5$ may be $C(R_5)$, $X_7$ may be $C(R_7)$, $X_8$ may be $C(R_8)$, $X_{11}$ may be $C(R_{11})$, $X_{12}$ may be $C(R_{12})$, $X_{14}$ may be $C(R_{14})$, $X_{15}$ may be $C(R_{15})$, $X_{17}$ may be $C(R_{17})$, and $X_{18}$ may be $C(R_{18})$, $X_1$ may be $C(R_1)$, $X_2$ may be $C(R_2)$, $X_4$ may be N, $X_5$ may be $C(R_5)$, $X_7$ may be $C(R_7)$, $X_8$ may be $C(R_8)$, $X_{11}$ may be $C(R_{11})$, $X_{12}$ may be $C(R_{12})$, $X_{14}$ may be $C(R_{14})$, $X_{15}$ may be $C(R_{15})$, $X_{17}$ may be $C(R_{17})$, and $X_{18}$ may be $C(R_{18})$, $X_1$ may be $C(R_1)$, $X_2$ may be $C(R_2)$, $X_4$ may be $C(R_4)$, $X_5$ may be N, $X_7$ may be $C(R_7)$, $X_8$ may be $C(R_8)$, $X_{11}$ may be $C(R_{11})$, $X_{12}$ may be $C(R_{12})$, $X_{14}$ may be $C(R_{14})$, $X_{15}$ may be $C(R_{15})$, $X_{17}$ may be $C(R_{17})$, and $X_{18}$ may be $C(R_{18})$, $X_1$ may be $C(R_1)$, $X_2$ may be $C(R_2)$, $X_4$ may be $C(R_4)$, $X_5$ may be $C(R_5)$, $X_7$ may be N, $X_8$ may be $C(R_8)$, $X_1$ may be $C(R_{11})$, $X_{12}$ may be $C(R_{12})$, $X_{14}$ may be $C(R_{14})$, $X_{15}$ may be $C(R_{15})$, $X_{17}$ may be $C(R_{17})$, and $X_{18}$ may be $C(R_{18})$, or $X_1$ may be $C(R_1)$, $X_2$ may be $C(R_2)$, $X_4$ may be $C(R_4)$, $X_5$ may be $C(R_5)$, $X_7$ may be $C(R_7)$, $X_8$ may be N, $X_{11}$ may be $C(R_{11})$, $X_{12}$ may be $C(R_{12})$, $X_{14}$ may be $C(R_{14})$, $X_{15}$ may be $C(R_{15})$, $X_{17}$ may be $C(R_{17})$, and $X_{18}$ may be $C(R_{18})$, but embodiments are not limited thereto.

In Formulae 1-1 to 1-15, *-$(L_{11})_{a11}$-Ar-$(L_{12})_{a12}$-*' may be a group represented by one of Formulae 4-1 to 4-20 above, but *-$(L_{11})_{a11}$-Ar-$(L_{12})_{a12}$-*' is not limited thereto.

The condensed cyclic compound of Formula 1 may be represented by one of Formulae 1-21 to 1-47:

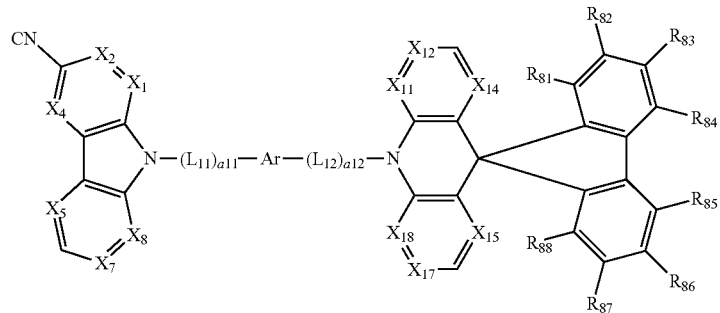

1-21

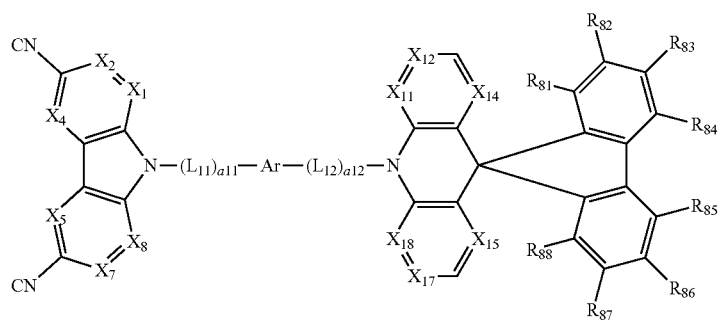

1-22

-continued
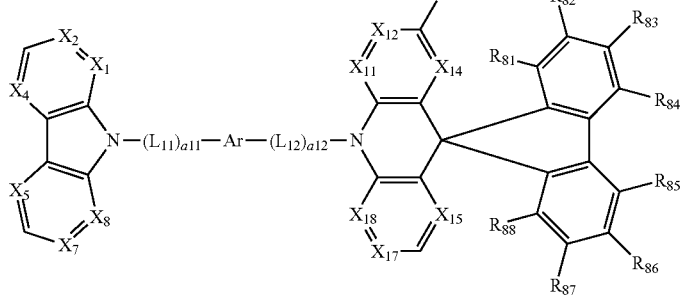
1-23
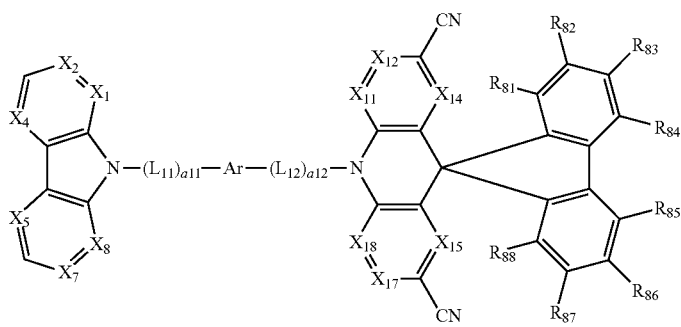
1-24
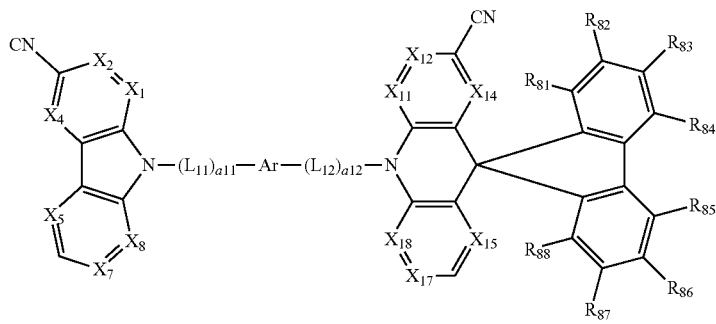
1-25
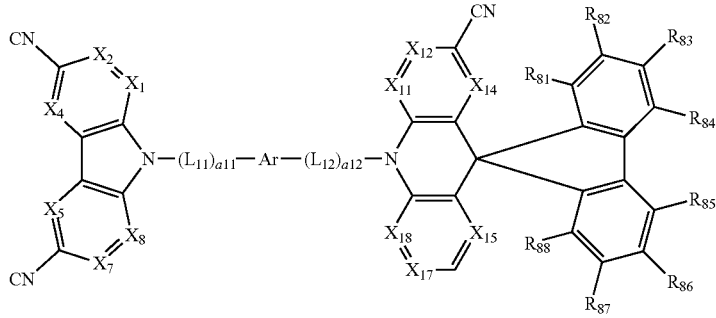
1-26
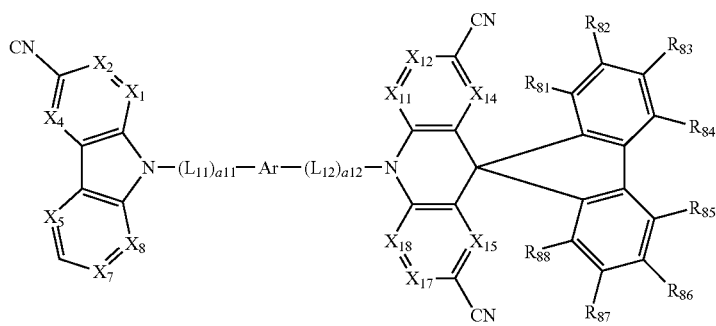
1-27

-continued
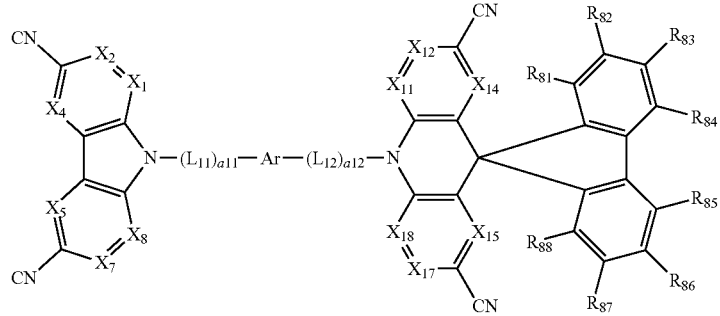
1-28
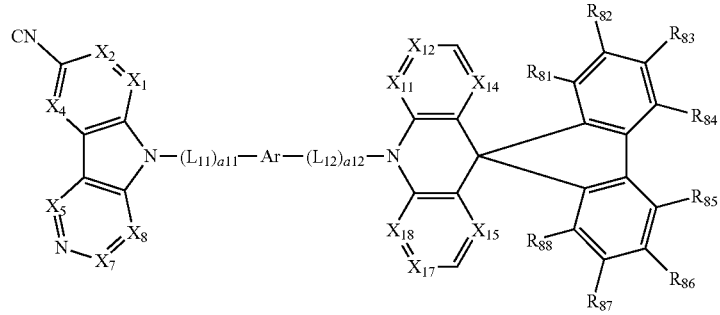
1-29
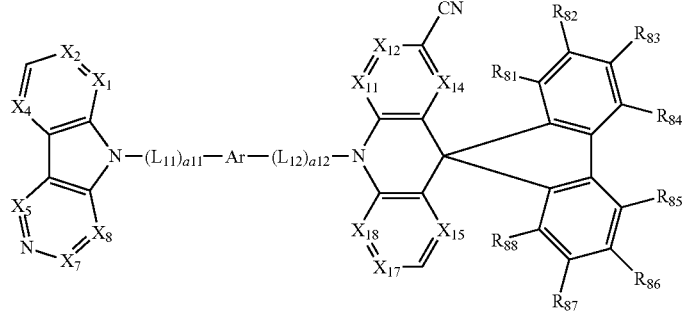
1-30
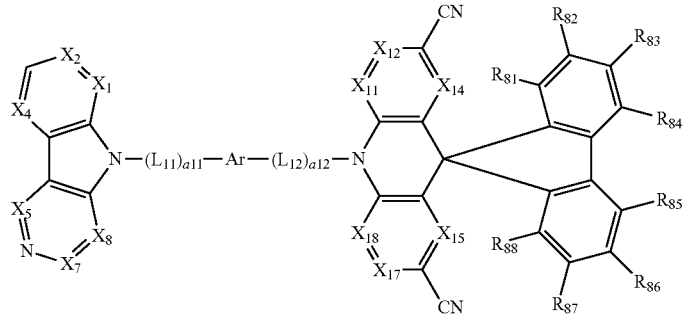
1-31
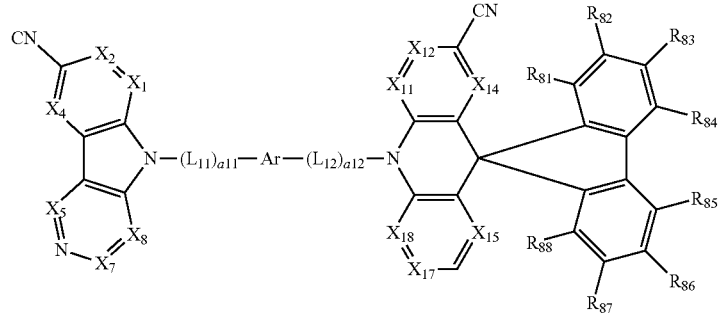
1-32

-continued
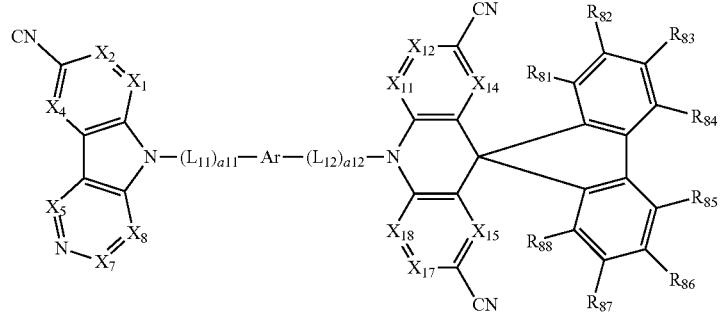 1-33
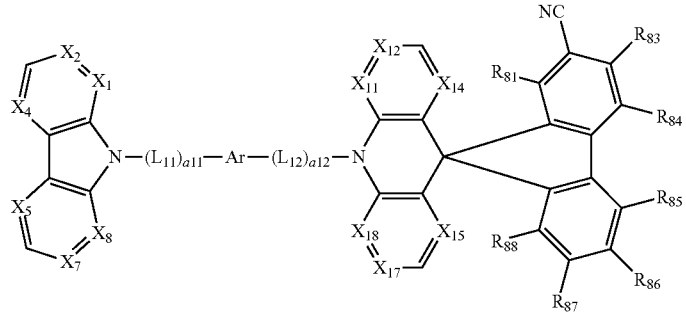 1-34
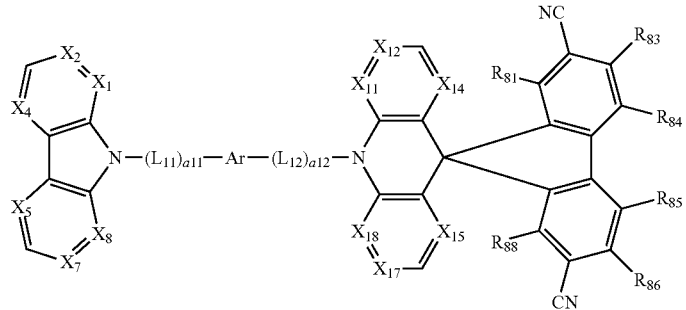 1-35
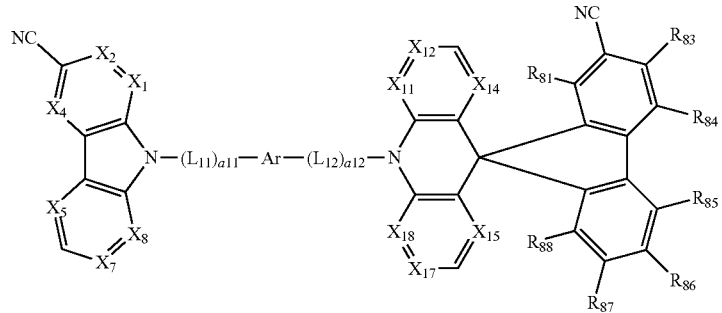 1-36
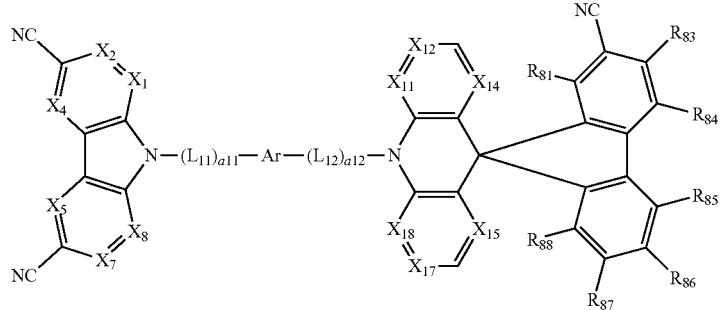 1-37

-continued
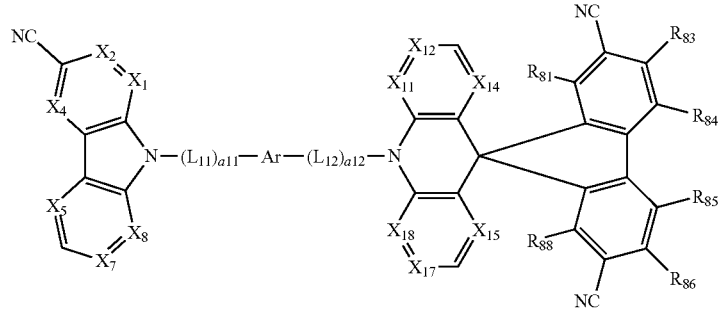
1-38
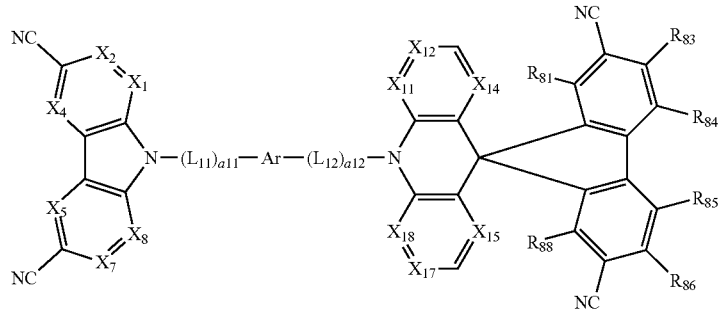
1-39
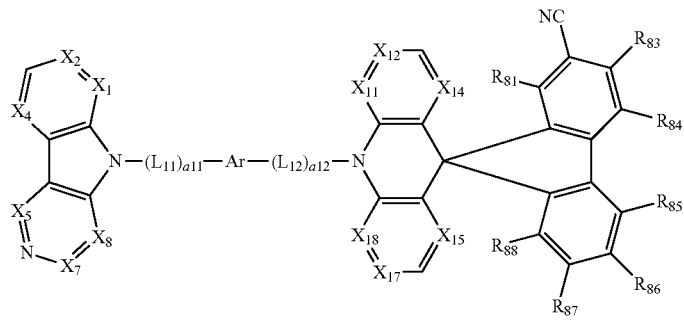
1-40
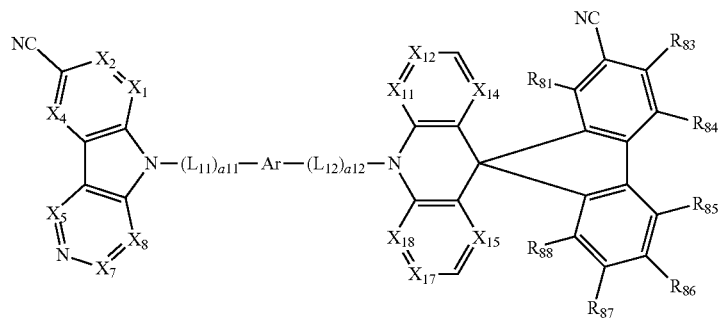
1-41
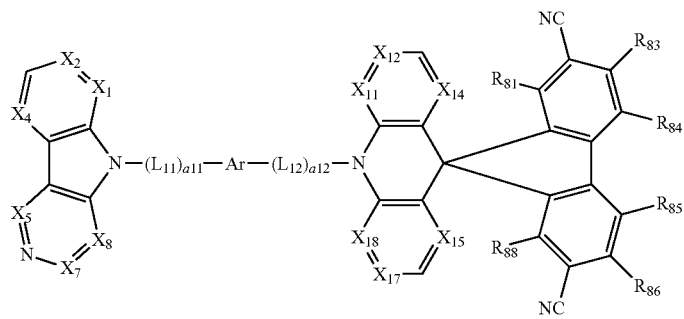
1-42

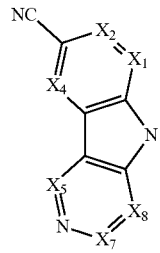
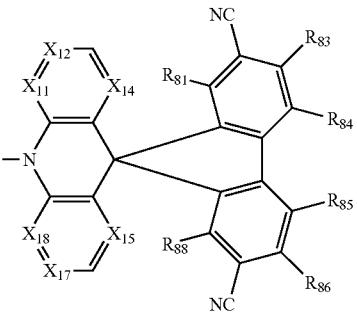

1-43

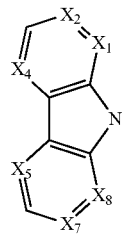

1-44

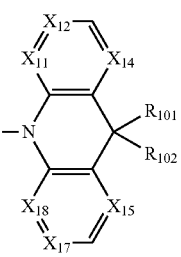

1-45

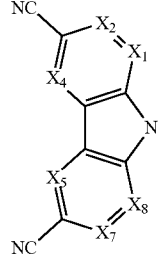

1-46

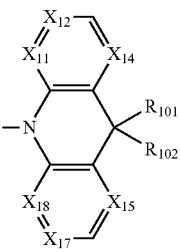

1-47

In Formulae 1-21 to 1-47,
descriptions of $X_1$, $X_2$, $X_4$, $X_5$, $X_7$, $X_8$, $X_{11}$, $X_{12}$, $X_{14}$, $X_{15}$, $X_{17}$, $X_{17}$, Ar, $L_{11}$, $L_{12}$, a11, and a12 may each be independently as referred to in the descriptions provided in connection with Formula 1, $R_{81}$ to $R_{88}$ may each be independently selected from a hydrogen, a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —Si($Q_{31}$)($Q_{32}$)($Q_{33}$), wherein $Q_{31}$ to $Q_{33}$ may each be independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, and a triazinyl group, and $R_{101}$ and $R_{102}$ may each be independently selected from:
a methyl group, an ethyl group, an n-propyl group, an iso-propyl group, an n-butyl group, an isobutyl group, a sec-butyl group, a tert-butyl group, a phenyl group, and a naphthyl group; and
a methyl group substituted with a cyano (—CN) group, an ethyl group, an n-propyl group, an iso-propyl group, an n-butyl group, an isobutyl group, a sec-butyl group, a tert-butyl group, a phenyl group, and a naphthyl group.

In an exemplary embodiment, in Formulae 1-21 to 1-47,
$X_1$ may be N, $X_2$ may be C($R_2$), $X_4$ may be C($R_4$), $X_5$ may be C($R_5$), $X_7$ may be C($R_7$), $X_8$ may be C($R_8$), $X_{11}$ may be C($R_{11}$), $X_{12}$ may be C($R_{12}$), $X_{14}$ may be C($R_{14}$), $X_{15}$ may be C($R_{15}$), $X_{17}$ may be C($R_{17}$), and $X_{18}$ may be C($R_{18}$), $X_1$ may be C($R_1$), $X_2$ may be N, $X_4$ may be C($R_4$), $X_5$ may be C($R_5$), $X_7$ may be C($R_7$), $X_8$ may be C($R_8$), $X_{11}$ may be C($R_{11}$), $X_{12}$ may be C($R_{12}$), $X_{14}$ may be C($R_{14}$), $X_{15}$ may be C($R_{15}$), $X_{17}$ may be C($R_{17}$), and $X_{18}$ may be C($R_{18}$), $X_1$ may be C($R_1$), $X_2$ may be C($R_2$), $X_4$ may be N, $X_5$ may be C($R_5$), $X_7$ may be C($R_7$), $X_8$ may be C($R_8$), $X_{11}$ may be C($R_{11}$), $X_{12}$ may be C($R_{12}$), $X_{14}$ may be C($R_{14}$), $X_{15}$ may be C($R_{15}$), $X_{17}$ may be C($R_{17}$), and $X_{18}$ may be C($R_{18}$), $X_1$ may be C($R_1$), $X_2$ may be C($R_2$), $X_4$ may be C($R_4$), $X_5$ may be N, $X_7$ may be C($R_7$), $X_8$ may be C($R_8$), $X_{11}$ may be C($R_{11}$), $X_{12}$ may be C($R_{12}$), $X_{14}$ may be C($R_{14}$), $X_{15}$ may be C($R_{15}$), $X_{17}$ may be C($R_{17}$), and $X_{18}$ may be C($R_{18}$), $X_1$ may be C($R_1$), $X_2$ may be C($R_2$), $X_4$ may be C($R_4$), $X_5$ may be C($R_5$), $X_7$ may be N, $X_8$ may be C($R_8$), $X_{11}$ may be C($R_{11}$), $X_{12}$ may be C($R_{12}$), $X_{14}$ may be C($R_{14}$), $X_{15}$ may be C($R_{15}$), $X_{17}$ may be C($R_{17}$), and $X_{18}$ may be C($R_{18}$), $X_1$ may be C($R_1$), $X_2$ may be C($R_2$), $X_4$ may be C($R_4$), $X_5$ may be C($R_5$), $X_7$ may be C($R_7$), $X_8$ may be N, $X_{11}$ may be C($R_{11}$), $X_{12}$ may be C($R_{12}$), $X_{14}$ may be C($R_{14}$), $X_{15}$ may be C($R_{15}$), $X_{17}$ may be C($R_{17}$), and $X_{18}$ may be C($R_{18}$), but embodiments are not limited thereto.

In another exemplary embodiment, in Formulae 1-21 to 1-47, *-(L$_{11}$)$_{a11}$-Ar-(L$_{12}$)$_{a12}$-*' may be a group represented by one of Formulae 4-1 to 4-20 above, but embodiments are not limited thereto.
The condensed cyclic compound of Formula 1 may be selected from Compounds 1 to 103, but the condensed cyclic compound of Formula 1 is not limited thereto.
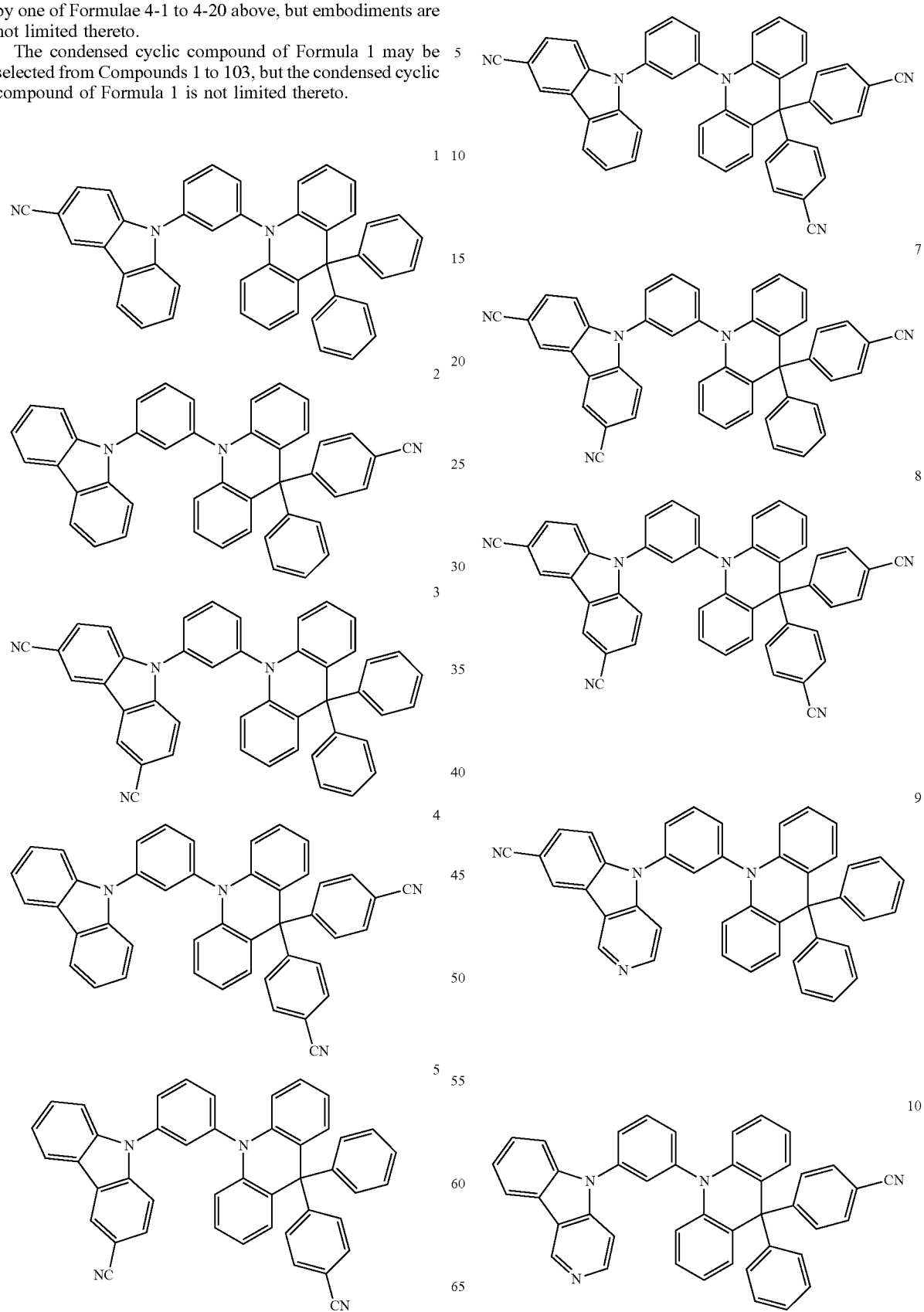

11
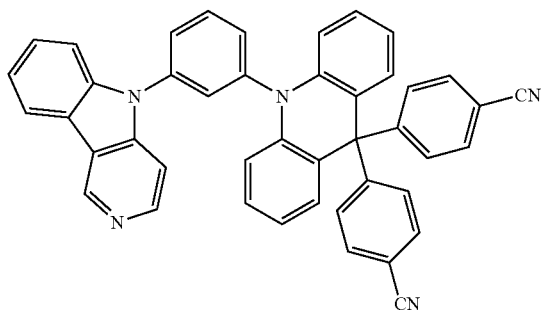
12
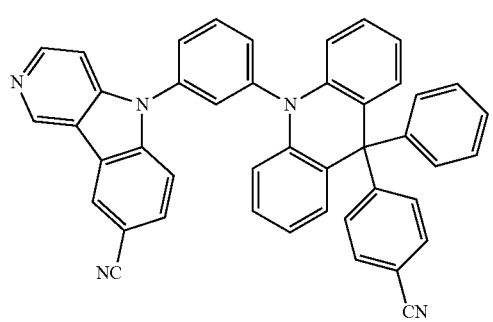
13
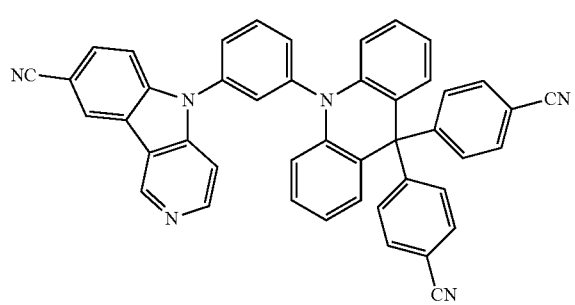
14
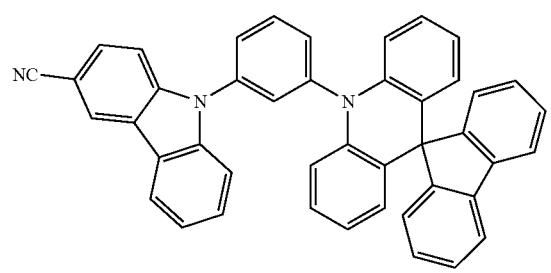
15
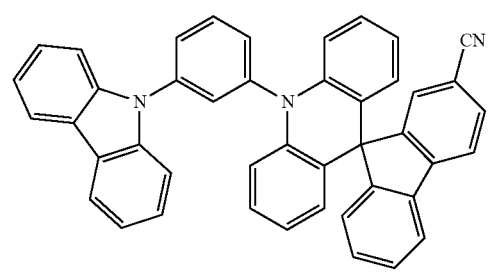
16
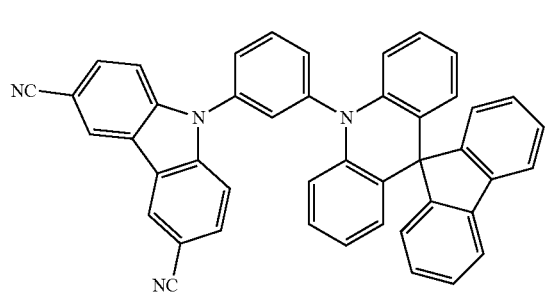
17
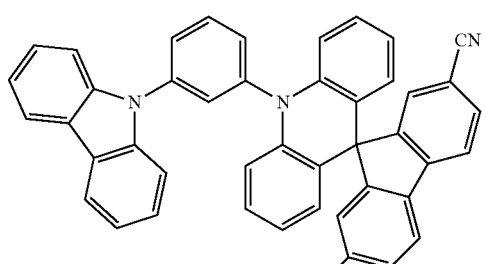
18
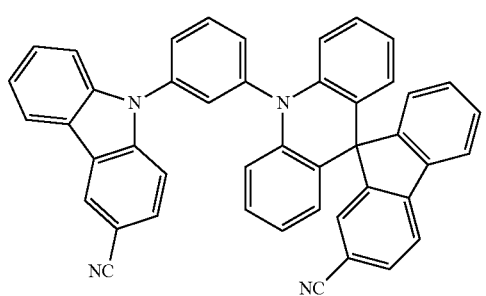
19
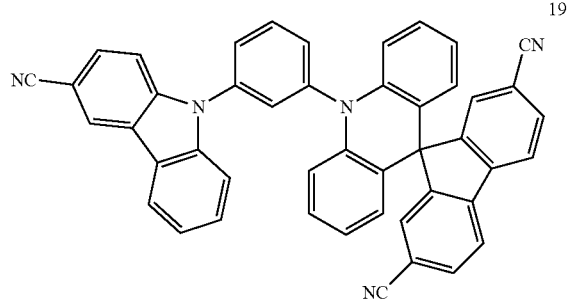
20
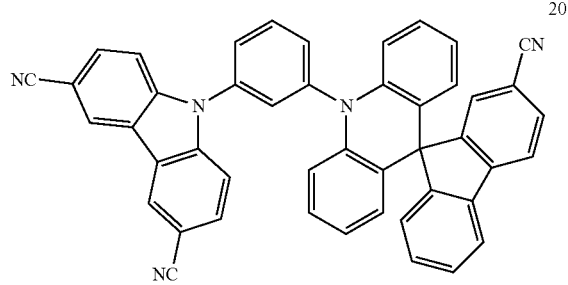

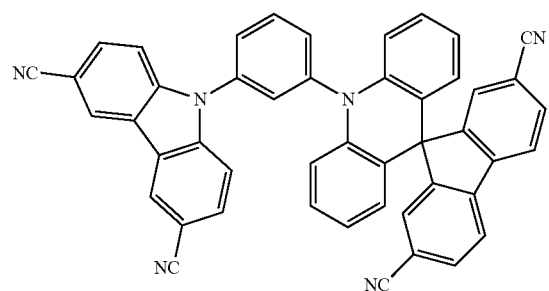
21
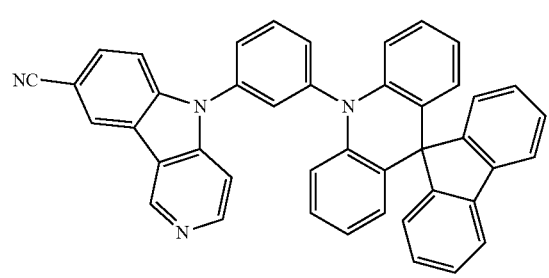
22
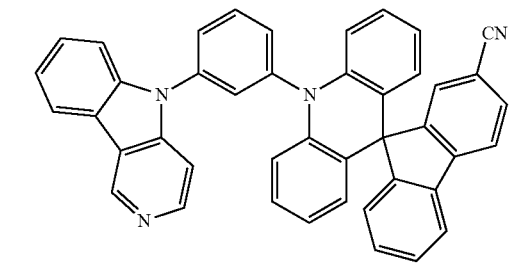
23
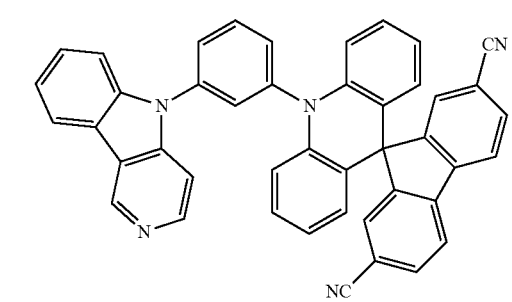
24
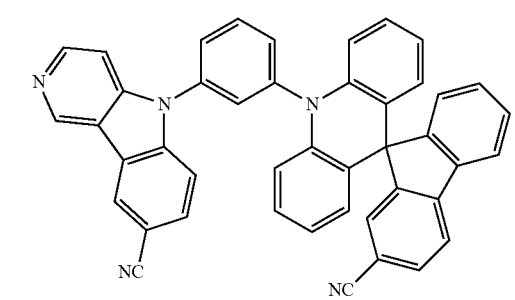
25
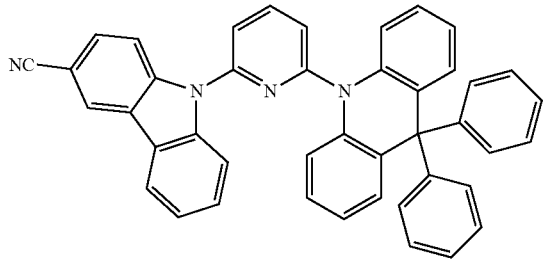
26
27
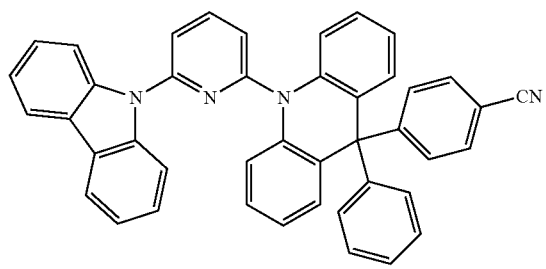
28
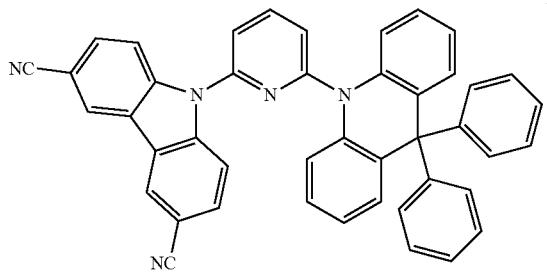
29
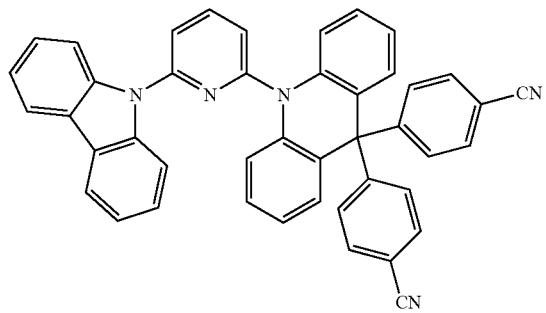
30

-continued
31
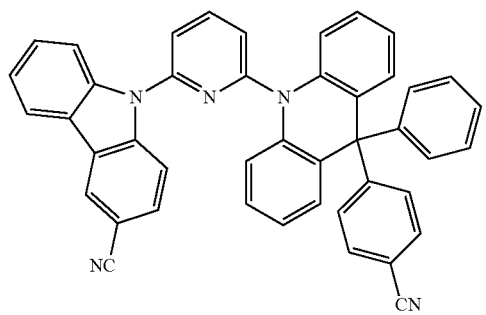
32
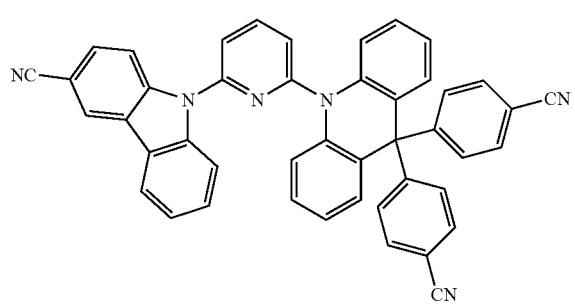
33
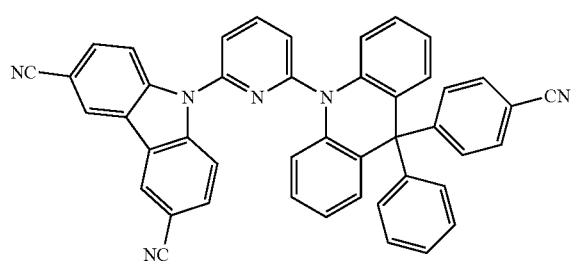
34
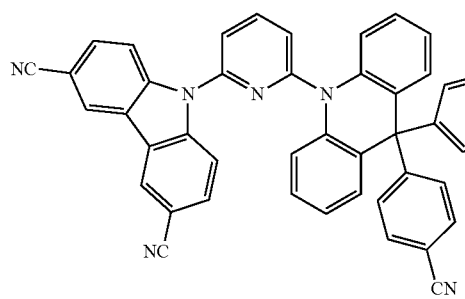
35
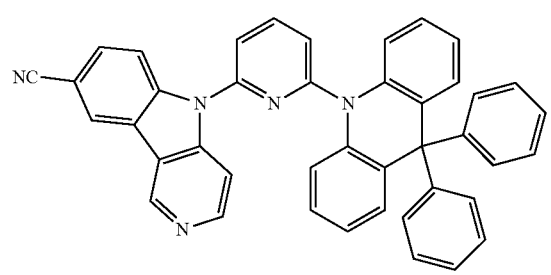
-continued
36
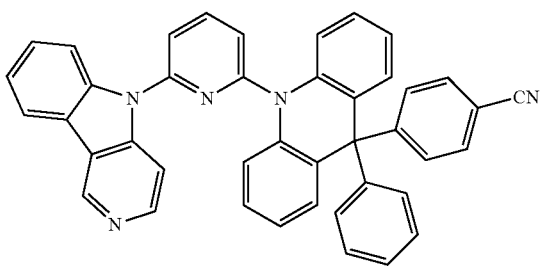
37
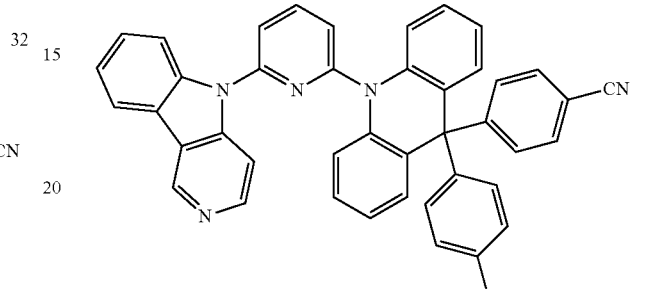
38
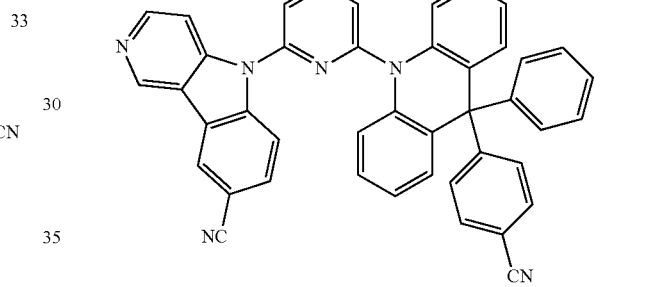
39
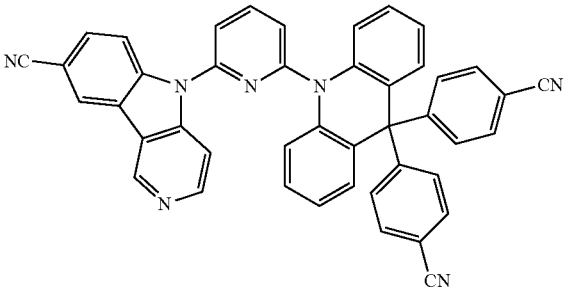
40

41
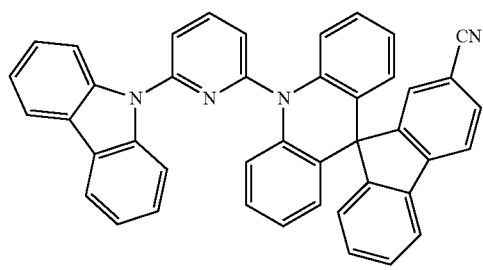
42
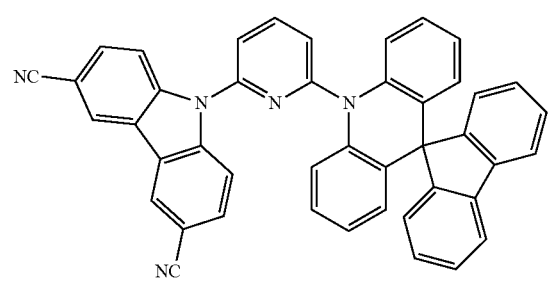
43
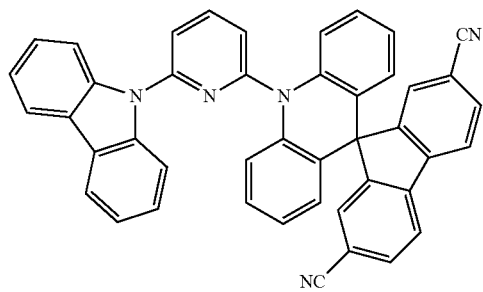
44
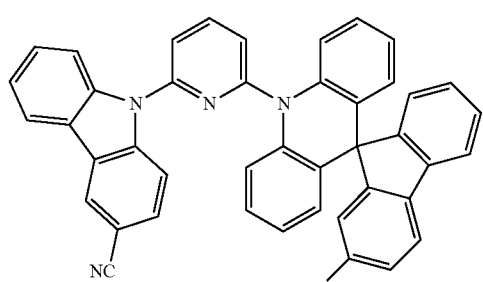
45
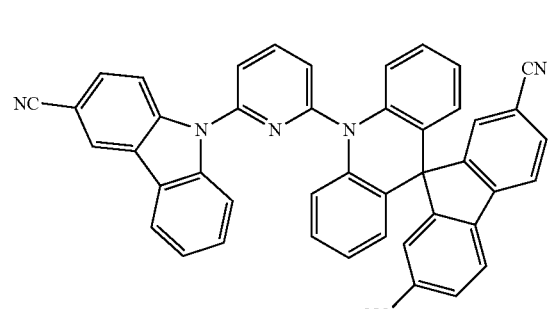
46
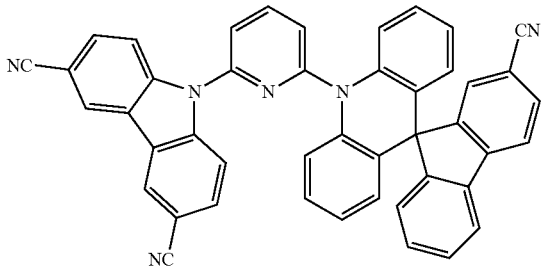
47
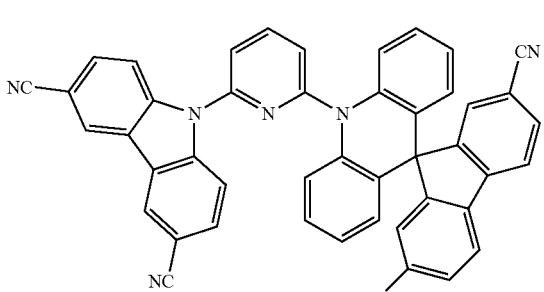
48
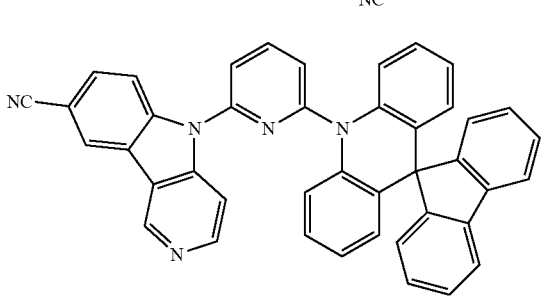
49
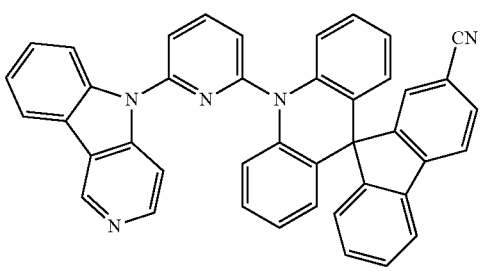
50
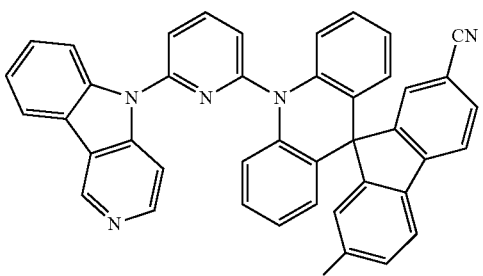

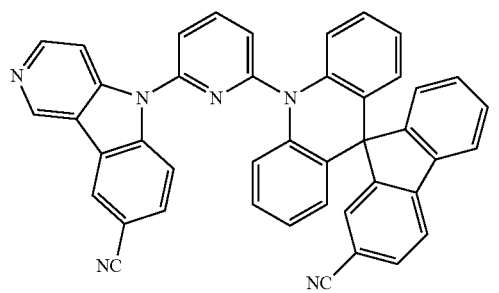
51
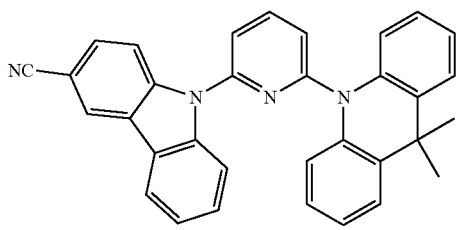
57
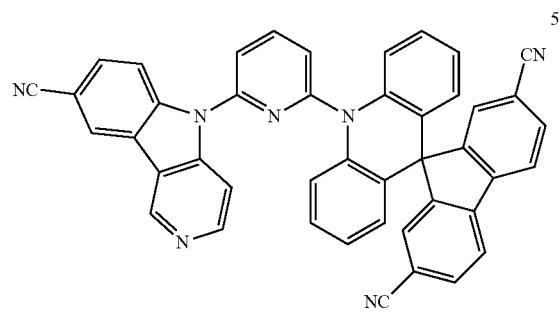
52
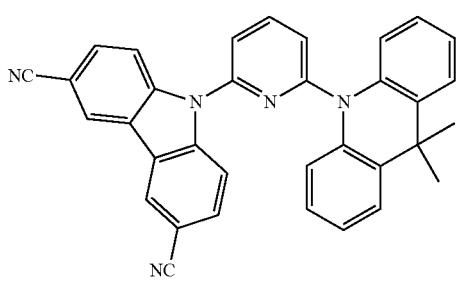
58
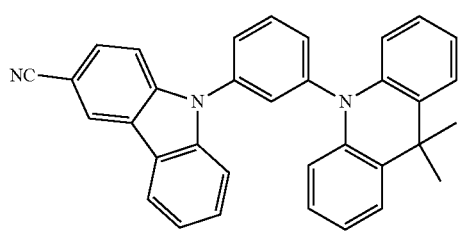
53
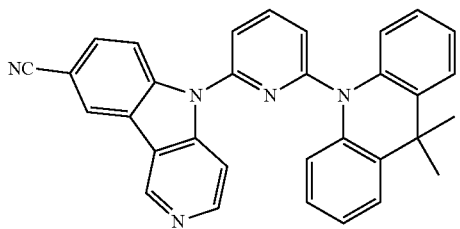
59
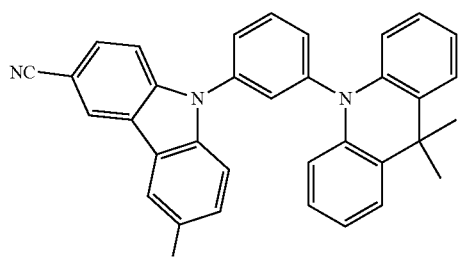
54
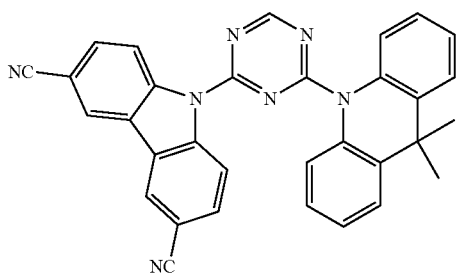
60
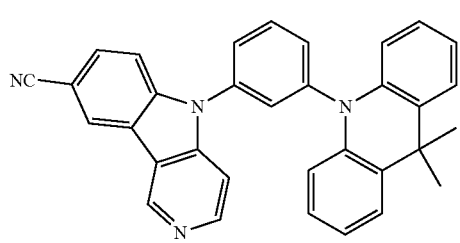
55
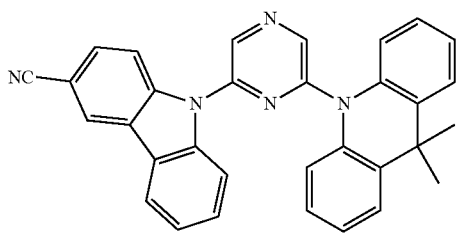
61
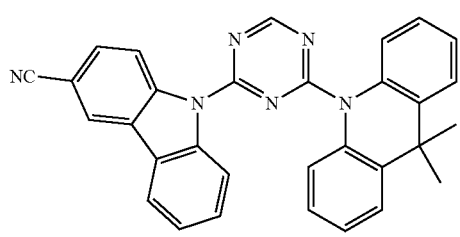
56
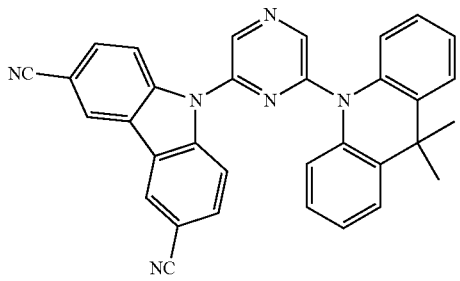
62

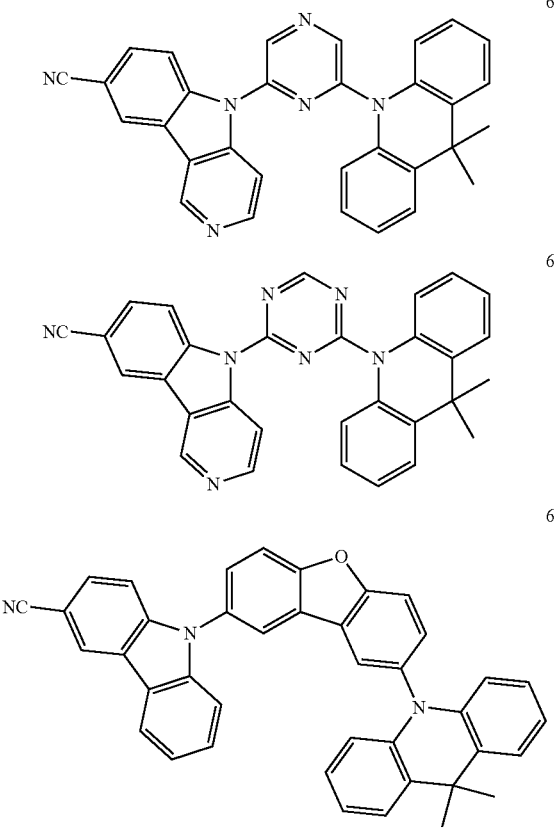
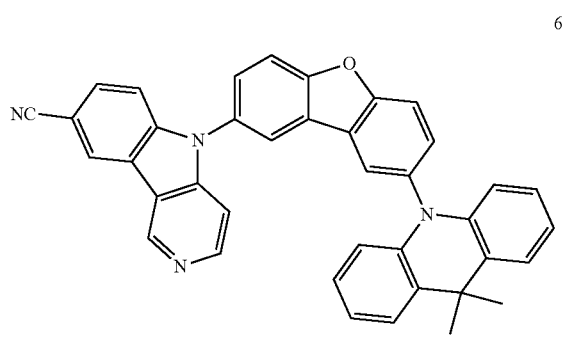
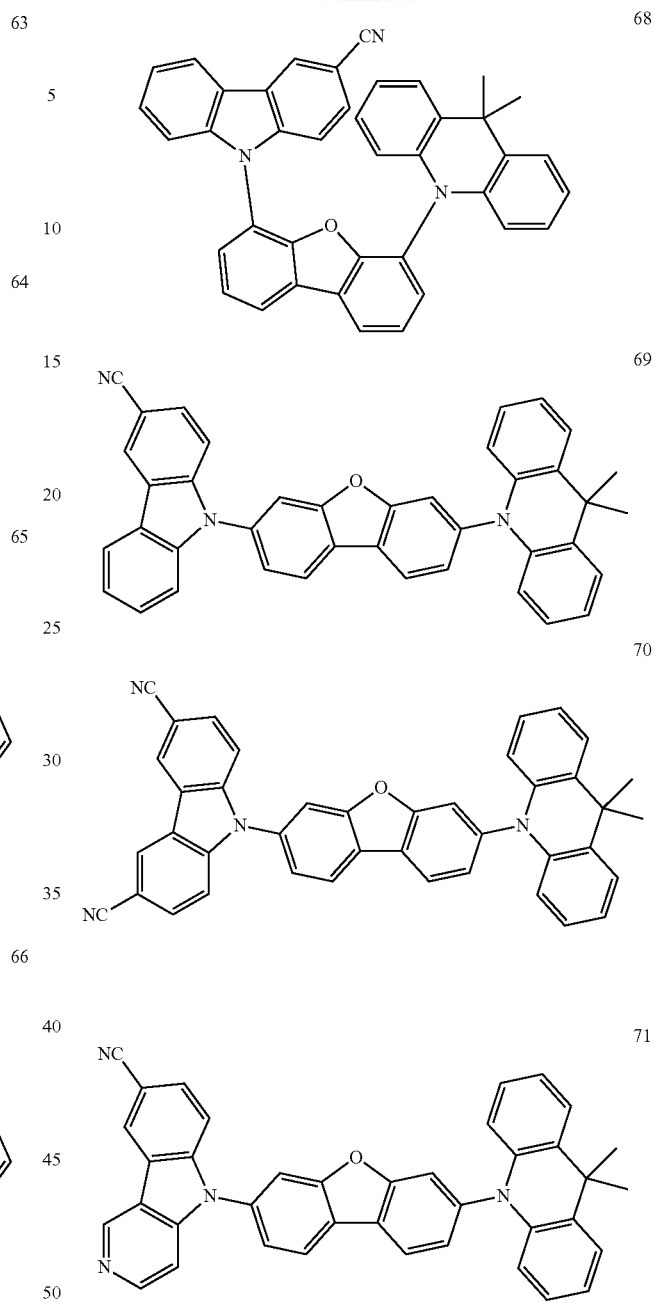

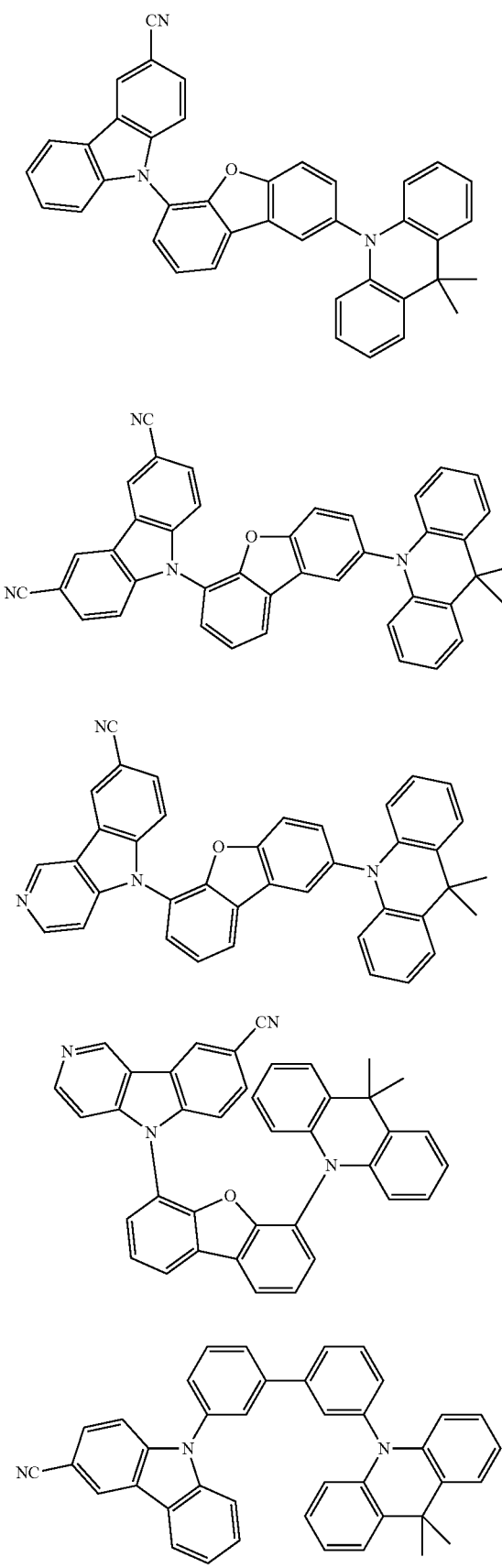
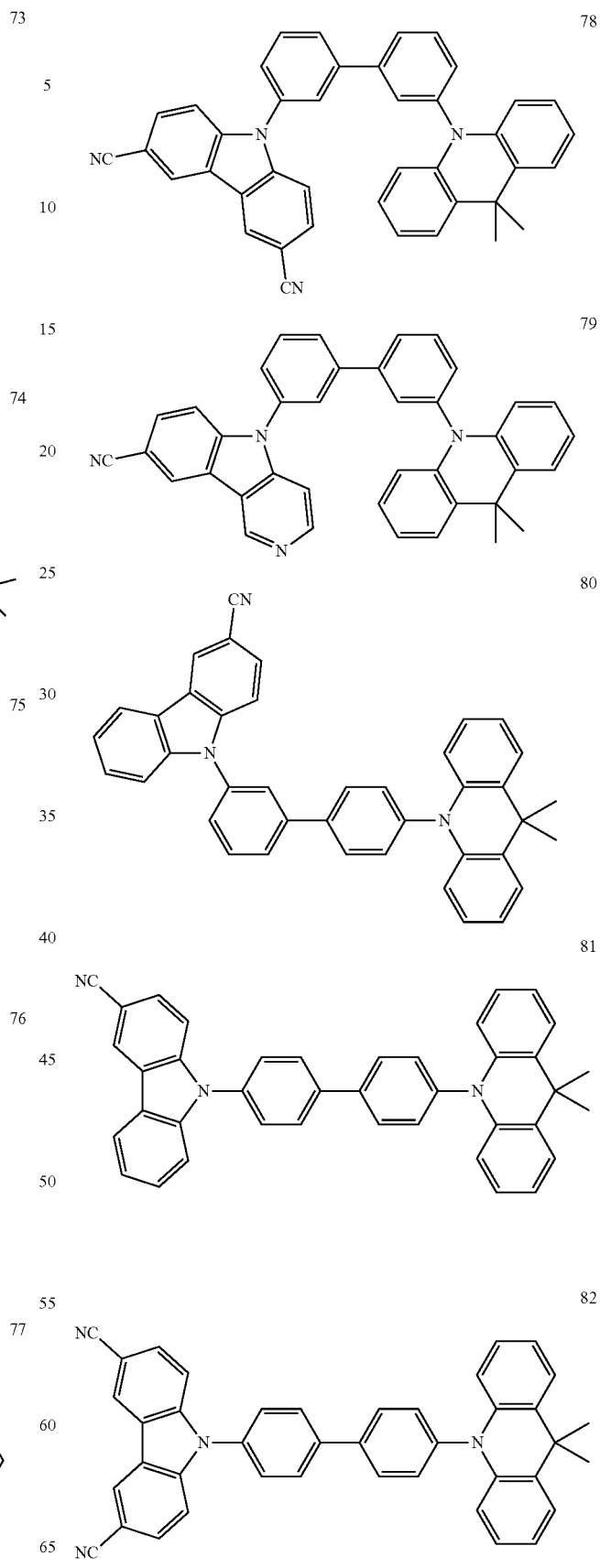

-continued
83
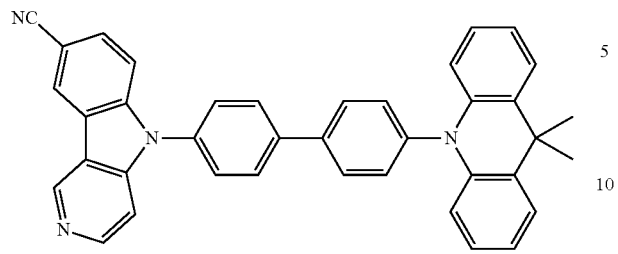
84
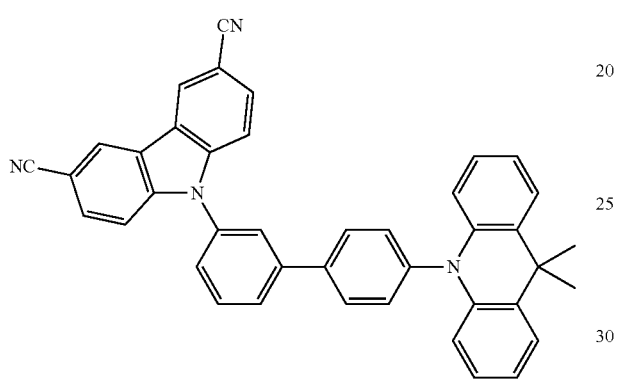
85
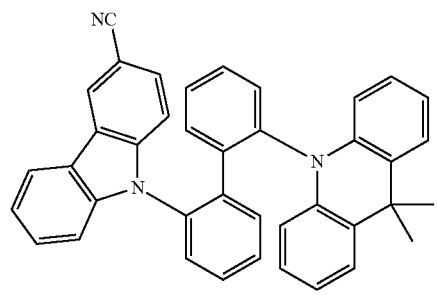
86
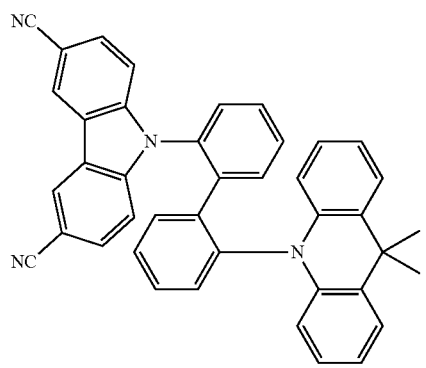
-continued
87
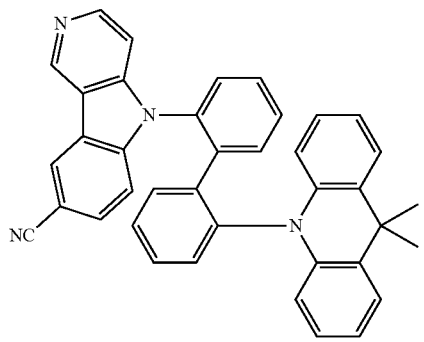
88
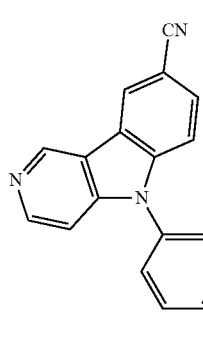
89
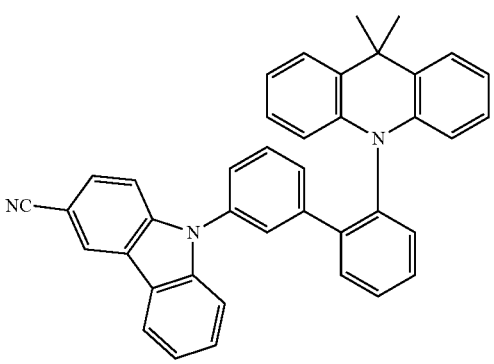
90
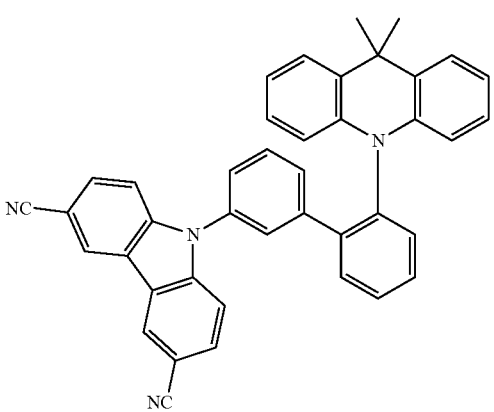

91
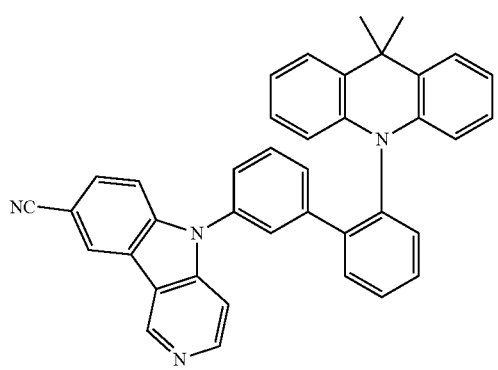
92
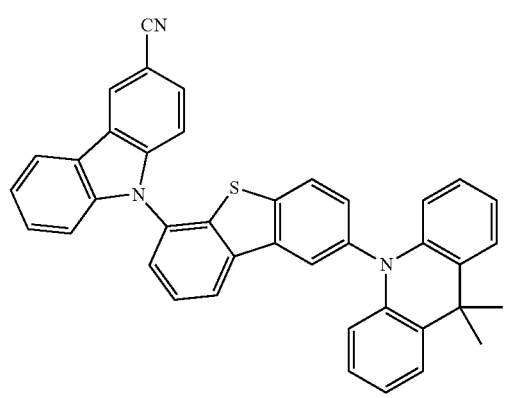
93
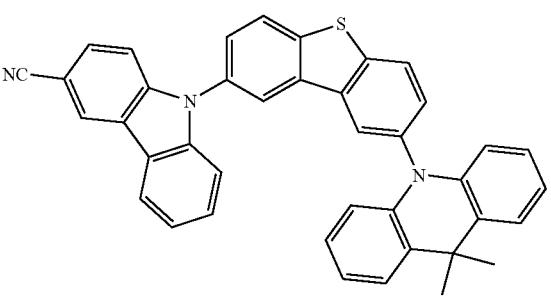
94
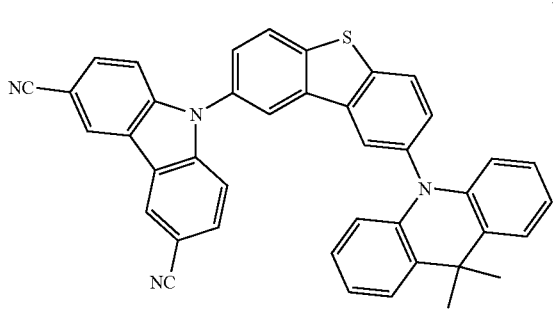
95
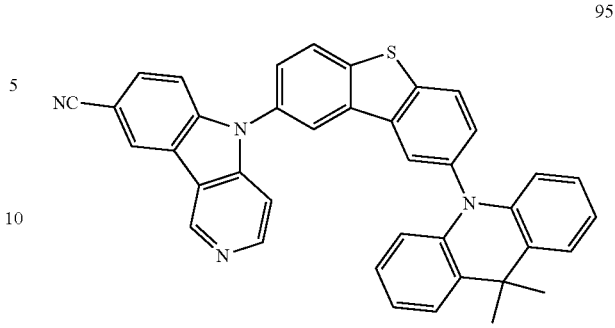
96
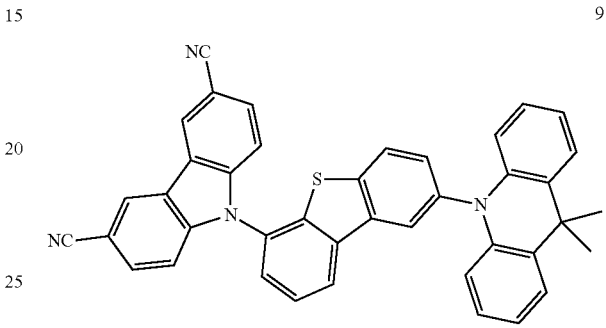
97
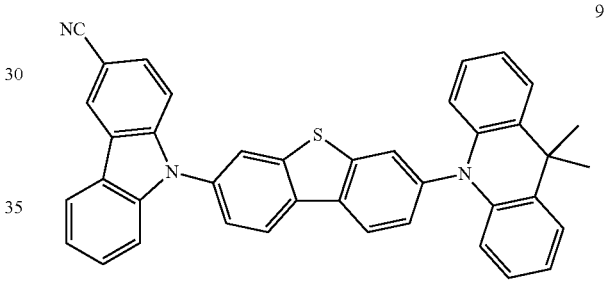
98
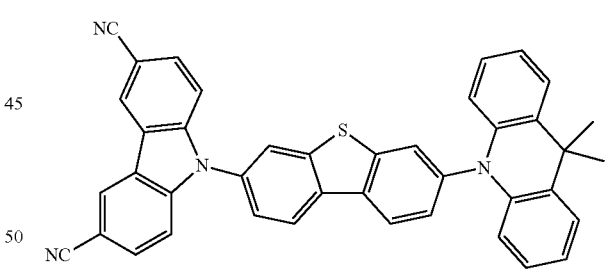
99
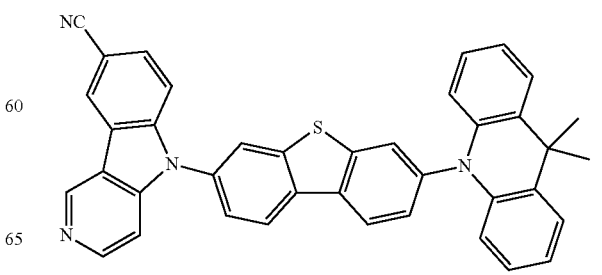

[Structures 100, 101, 102, 103]

Since the condensed cyclic compound of Formula 1 always includes at least one cyano (—CN) group, thermal stability and electric characteristics of the condensed cyclic compound of Formula 1 may be improved. Accordingly, an organic light-emitting device including the condensed cyclic compound of Formula 1 may also have improved lifespan and efficiency.

Since the condensed cyclic compound of Formula 1 includes a linking group represented by one of Formulae 2A to 2D, the condensed cyclic compound of Formula 1 may have triplet energy at a high level.

In addition, adjustment of the number of the cyano (—CN) group included in the condensed cyclic compound of Formula 1 may easily derive a desirable HOMO and LUMO energy level. In addition, adjustment of the number of the phenyl group included in the condensed cyclic compound of Formula 1 may facilitate migration of holes and electrons of the condensed cyclic compound of Formula 1.

A method of synthesizing the condensed cyclic compound of Formula 1 may be apparent to one of ordinary skill in the art based on the following description of Synthesis Examples.

That is, the condensed cyclic compound of Formula 1 may be suitable for use in an organic layer of an organic light-emitting device, for example, as a host included in an emission layer of an organic layer.

There is provided an organic light-emitting device including:

a first electrode;
a second electrode; and
an organic layer that is disposed between the first electrode and the second electrode, wherein the organic layer includes an emission layer and the condensed cyclic compound of Formula 1.

The organic light-emitting device includes the organic layer including the condensed cyclic compound of Formula 1, and thus may exhibit low driving voltage, high efficiency, high brightness, and high quantum emission efficiency and have long lifespan characteristics.

The condensed cyclic compound of Formula 1 may be used between a pair of electrodes of the organic light-emitting device. For example, the emission layer may include the condensed cyclic compound of Formula 1, and in this embodiment, the condensed cyclic compound may act as a host while the emission layer may further include a dopant.

As used herein, the expression "(an organic layer) includes a condensed cyclic compound" may be construed as meaning "(an organic layer) may include one of the condensed cyclic compound within the scope of Formula 1 or at least two different condensed cyclic compounds within the scope of Formula 1".

For example, the organic layer may include, as the condensed cyclic compound of Formula 1, Compound 1 only. Here, Compound 1 may be included in the emission layer of the organic light-emitting device. Alternatively, the organic layer may include, as the condensed cyclic compound of Formula 1, Compound 1 and Compound 2. Here, Compound 1 and Compound 2 may be both included in a same layer (for example, in an exemplary embodiment, Compound 1 and Compound 2 are both included in the emission layer).

The first electrode may be an anode, which is a hole injection electrode, and the second electrode may be a cathode, which is an electron injection electrode. Alternatively, the first electrode may be a cathode, which is an electron injection electrode, and the second electrode may be an anode, which is a hole injection electrode.

For example, the first electrode may be an anode, the second electrode may be a cathode, and the organic layer may include:

i) a hole transport region disposed between the first electrode and the emission layer and including at least one of a hole injection layer (HIL), a hole transport layer (HTL), and an electron blocking layer (EBL) and
ii) an electron transport region disposed between the emission layer and the second electrode and including at least one of a hole blocking layer (HBL), an electron transport layer (ETL), and an electron injection layer (EIL).

As used herein, the term "organic layer" refers to a single and/or a plurality of layers disposed between the first electrode and the second electrode in the organic light-emitting device. A material included in the "organic layer" is not only an organic compound, but also a metal-containing organometallic complex.

FIG. 1 is a schematic cross-sectional view of a structure of an organic light-emitting device 10 according to an exemplary embodiment of the present inventive concept. Hereinafter, a structure of an organic light-emitting device according to an example embodiment and a method of manufacturing an organic light-emitting device according to an example embodiment will be described as follows in connection with FIG. 1. The organic light-emitting device 10 may have a stacked structure of a first electrode 11, an organic layer 15, and a second electrode 19.

A substrate may be additionally disposed under the first electrode 11 or on the second electrode 19 in the organic light-emitting device 10. Any substrate available in the art may be used, and for example, the substrate may be a glass substrate or transparent plastic substrate, each with each having excellent mechanical strength, thermal stability, transparency, surface smoothness, ease of handling, and water-resistance.

The first electrode 11 may be formed by, e.g., depositing or sputtering a material for forming the first electrode 11 on the substrate. When the first electrode 11 is an anode, the material for forming the first electrode 11 may be selected from materials having a high work function to facilitate hole injection. The first electrode 11 may be a reflective electrode, a semi-refractive electrode, a semi-transmissive electrode, or a transmissive electrode. The material for forming the first electrode 11 may be an indium tin oxide (ITO), indium zinc oxide (IZO), tin oxide ($SnO_2$), or zinc oxide (ZnO). Alternatively, the material for forming the first electrode 110 may be a metal, such as magnesium (Mg), aluminum (Al), aluminum-lithium (Al—Li), calcium (Ca), magnesium-indium (Mg—In), and magnesium-silver (Mg—Ag).

The first electrode 11 may have a single-layer structure or a multi-layer structure including two or more layers. For example, the first electrode 11 may have a triple-layer structure of ITO/Ag/ITO, but the structure of the first electrode 11 is not limited thereto.

The organic layer 14 is disposed on the first electrode 11.

The organic layer 15 may include the hole transport region, the emission layer, and the electron transport region.

The hole transport region may be disposed between the first electrode 11 and the emission layer.

The hole transport region may include at least one of an HIL, an HTL, an EBL, and a buffer layer.

The hole transport region may include an HIL only or an HTL only. Alternatively, the hole transport region may have a structure of HIL/HTL or a structure of HIL/HTL/EBL, wherein layers of each structure are sequentially stacked from the first electrode 11.

When the hole transport region include an HIL, the HIL may be formed on the first electrode 11 by using various suitable methods, such as vacuum deposition, spin coating, casting, or a Langmuir-Blodgett (LB) method.

When the HIL is formed by vacuum deposition, the vacuum deposition may be performed, e.g., at a deposition temperature in a range of about 100° C. to about 500° C., at a vacuum degree in a range of about $10^{-8}$ to about $10^{-3}$ torr, and at a deposition rate in a range of about 0.01 to about 100 Angstroms per second (Å/sec), depending upon a compound for forming the HIL to be deposited, a structure of the HIL to be formed, and thermal characteristics of the HIL to be formed, but the deposition conditions are not limited thereto.

When the HIL is formed by spin coating, the spin coating may be performed, e.g., at a coating speed of about 2,000 revolutions per minute (rpm) to about 5,000 rpm and at a temperature of about 80° C. to 200° C. for removing solvents after the spin coating, depending upon a material for forming the HIL to be deposited, a structure of the HIL to be formed, and thermal characteristics of the HIL to be formed, but the coating conditions are not limited thereto.

Conditions for forming an HTL and an EBL included in the hole transport region include may be inferred based on the deposition conditions or the coating conditions for forming the HIL.

The hole transport region may include, for example, at least one of m-MTDATA, TDATA, 2-TNATA, NPB, β-NPB, TPD, Spiro-TPD, Spiro-NPB, methylated NPB, TAPC, HMTPD, 4,4',4"-tris(N-carbazolyl)triphenylamine (TCTA), polyaniline/dodecylbenzene sulfonic acid (Pani/DBSA), poly(3,4-ethylenedioxythiophene)/poly(4-styrenesulfonate) (PEDOT/PSS), polyaniline/camphor sulfonic acid (Pani/CSA), polyaniline/poly(4-styrenesulfonate) (PANI/PSS), a compound represented by Formula 201, and a compound represented by Formula 202:

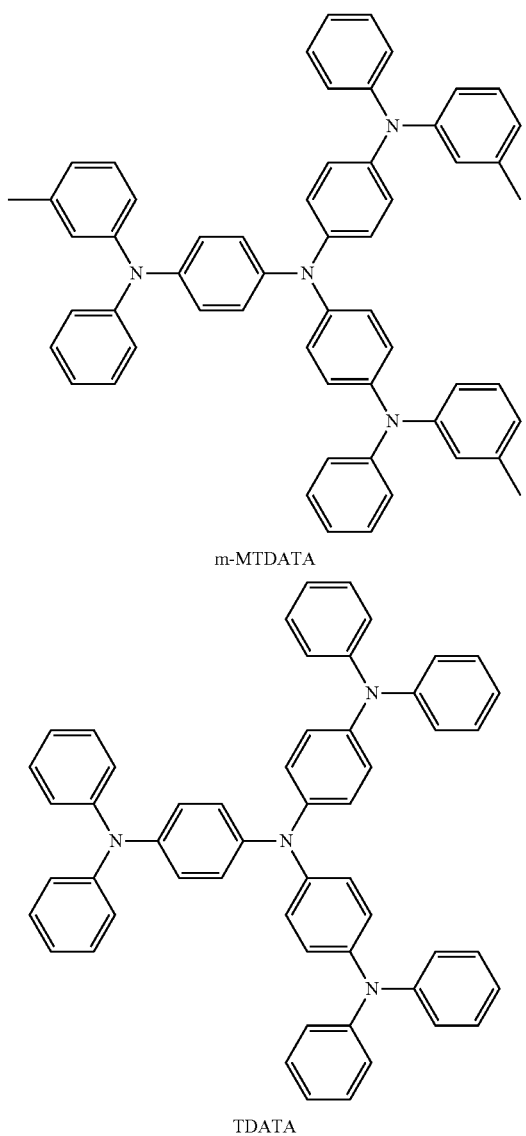

m-MTDATA

TDATA

-continued
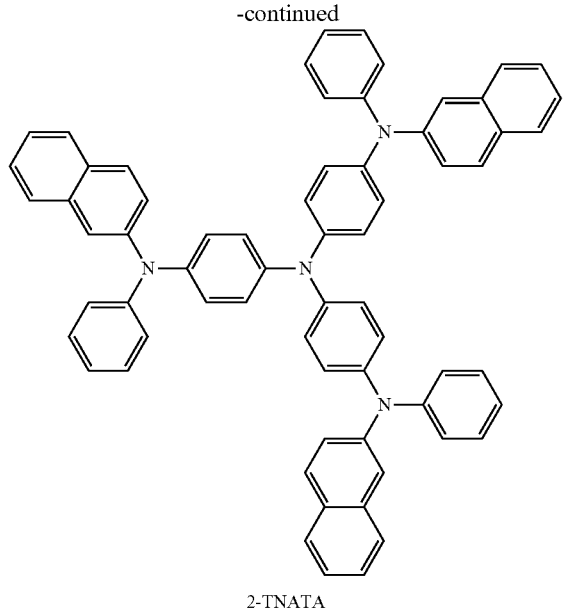
2-TNATA
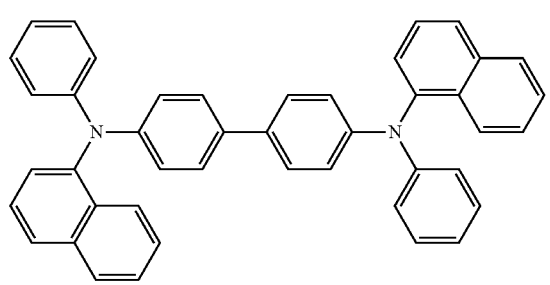
NPB
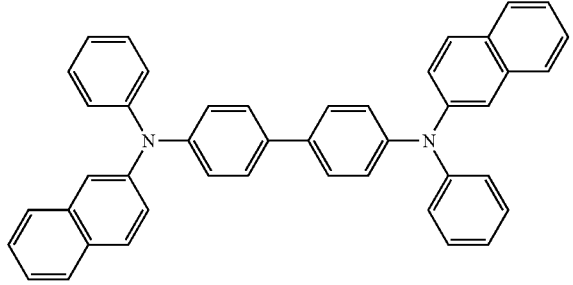
β-NPB
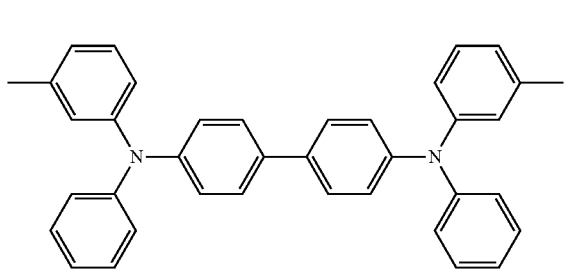
TPD
-continued
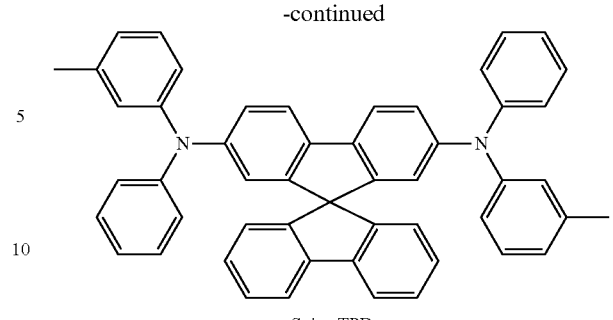
Spiro-TPD
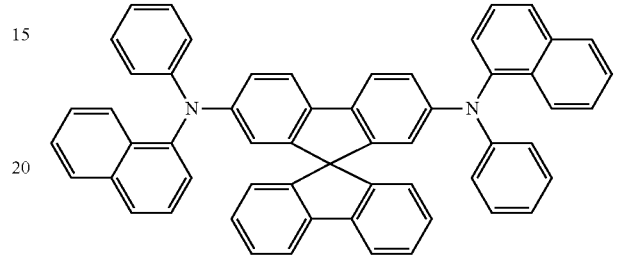
Spiro-NPB
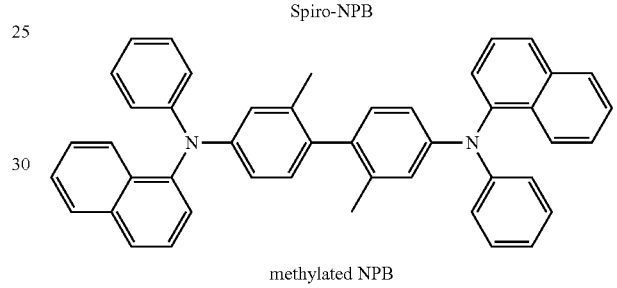
methylated NPB
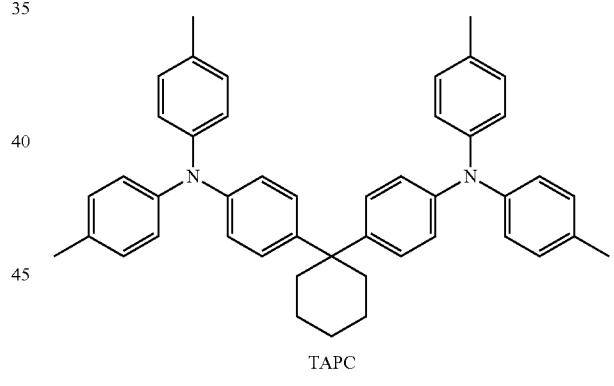
TAPC
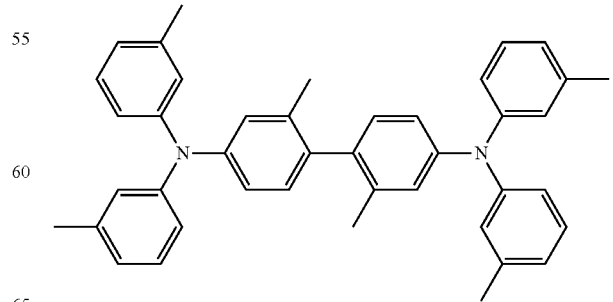
HMTPD -continued Formula 201

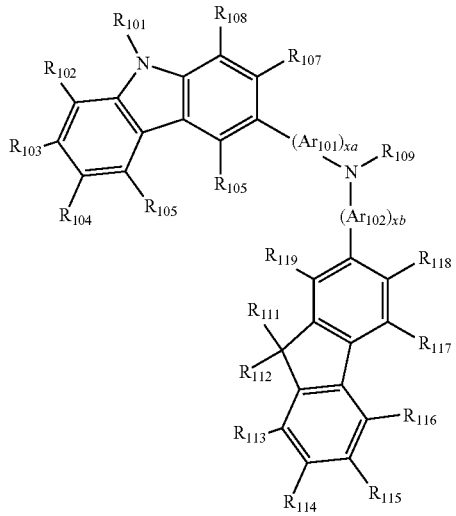

Formula 202

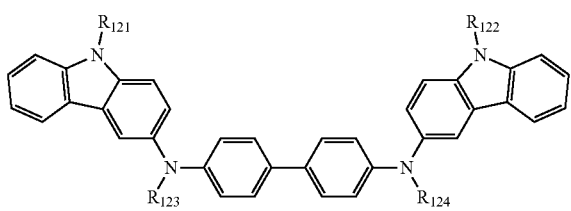

In Formula 201, $Ar_{101}$ and $Ar_{102}$ may each be independently selected from:
- a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and
- a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one of a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group.

In Formula 201, xa and xb may each be independently an integer of 0 to 5, or may be 0, 1, or 2. For example, in Formula 201, xa may be 1 and xb may be 0, but xa and xb are not limited thereto.

In Formulae 201 and 202, $R_{101}$ to $R_{108}$, $R_{111}$ to $R_{119}$, and $R_{121}$ to $R_{124}$ may each be independently selected from:
- a hydrogen, a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (e.g., a methyl group, an ethyl group, a propyl group, a butyl group, pentyl group, or a hexyl group), and a $C_1$-$C_{10}$ alkoxy group (e.g., a methoxy group, an ethoxy group, a propoxy group, a butoxy group, or a pentoxy group);
- a $C_1$-$C_{10}$ alkyl group and a $C_1$-$C_{10}$ alkoxy group, each substituted with at least one of a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, and a phosphoric acid group or a salt thereof;
- a phenyl group, a naphthyl group, an anthracenyl group, a fluorenyl group, and a pyrenyl group; and
- a phenyl group, a naphthyl group, an anthracenyl group, a fluorenyl group, and a pyrenyl group, each substituted with at least one of a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but $R_{101}$ to $R_{138}$, $R_{111}$ to $R_{119}$, and $R_{121}$ to $R_{124}$ are not limited thereto.

In Formula 201, $R_{109}$ may be selected from:
- a phenyl group, a naphthyl group, an anthracenyl group, and a pyridinyl group; and
- a phenyl group, a naphthyl group, an anthracenyl group, and a pyridinyl group, each substituted with at least one of a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{23}$ alkoxy group, a phenyl group, a naphthyl group, an anthracenyl group, and a pyridinyl group.

In an exemplary embodiment, the compound of Formula 201 may be represented by Formula 201A, but embodiments are not limited thereto:

Formula 201A
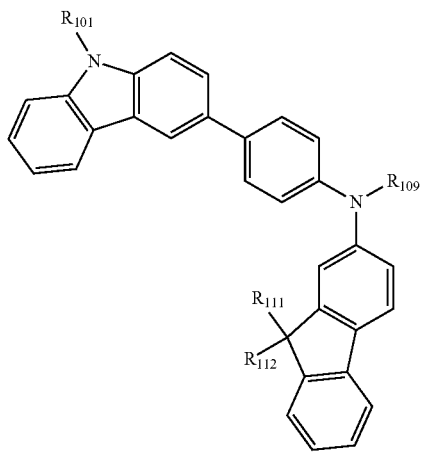
In Formula 201A, descriptions of $R_{101}$, $R_{111}$, $R_{112}$, and $R_{109}$ are the same as defined in the present specification.
For example, the compound of Formula 201 and the compound of Formula 202 may include Compounds HT1 to HT20, but the compound of Formula 201 and the compound of Formula 202 are not limited thereto:
HT1
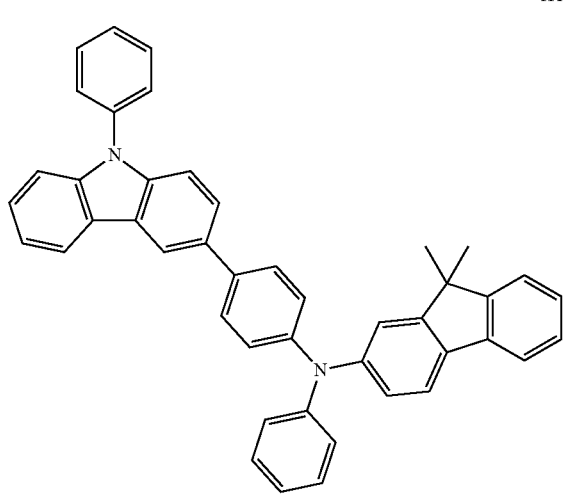
HT2
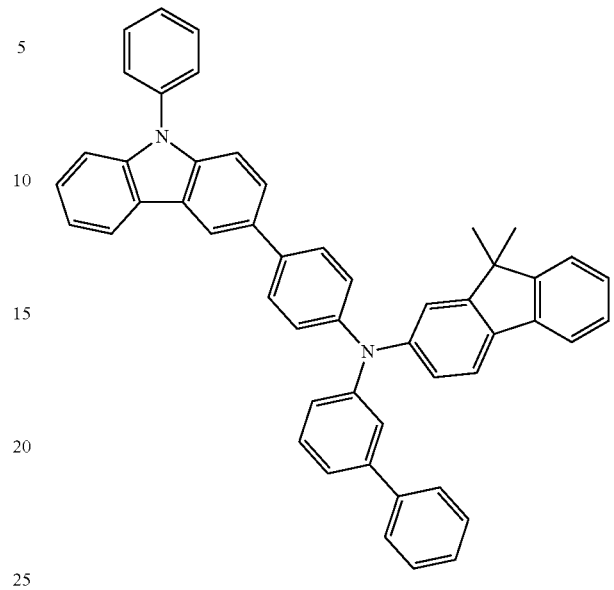
HT3
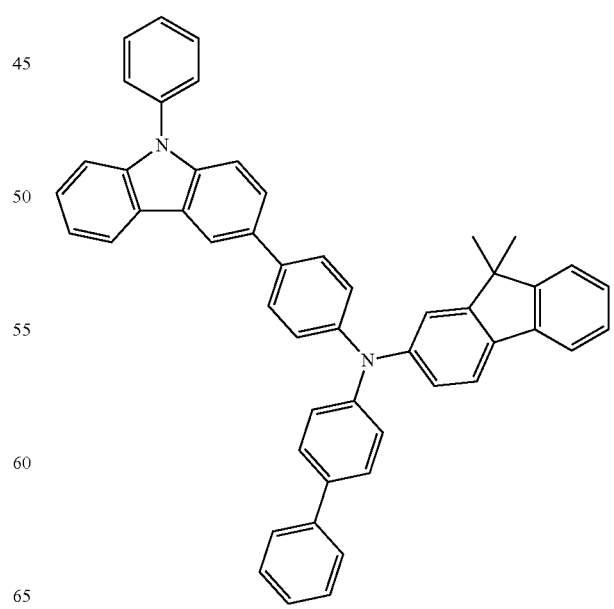

HT4
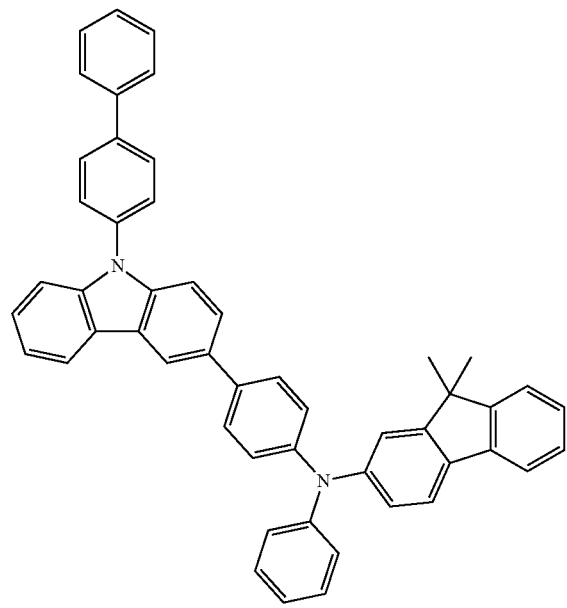
HT6
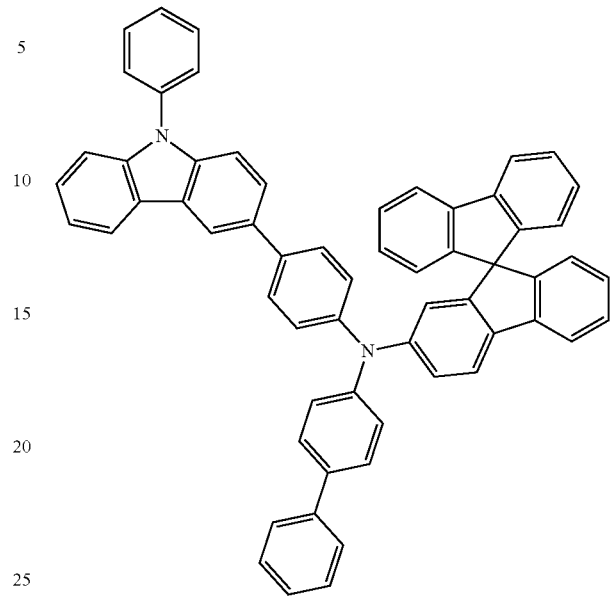
HT5
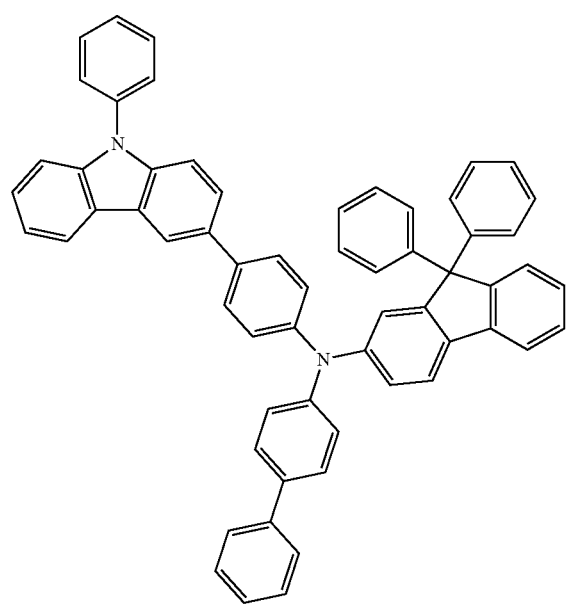
HT7
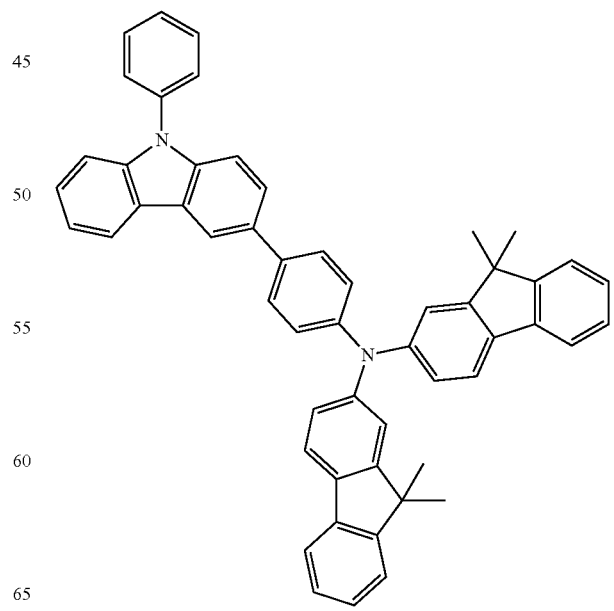

HT8
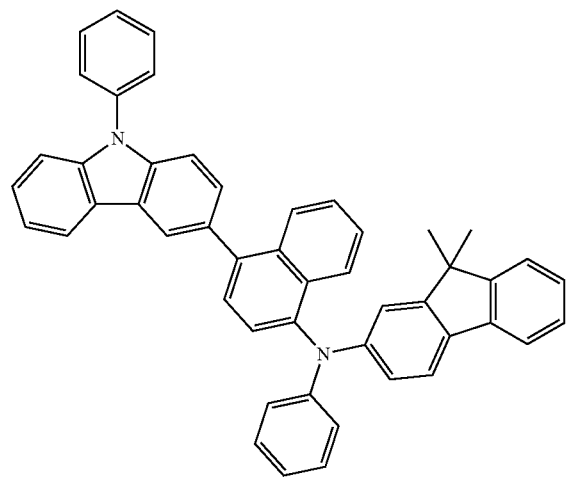
HT9
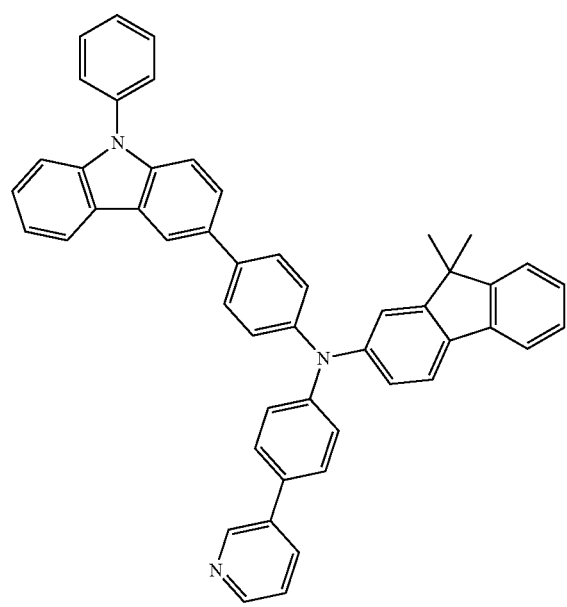
HT10
HT11
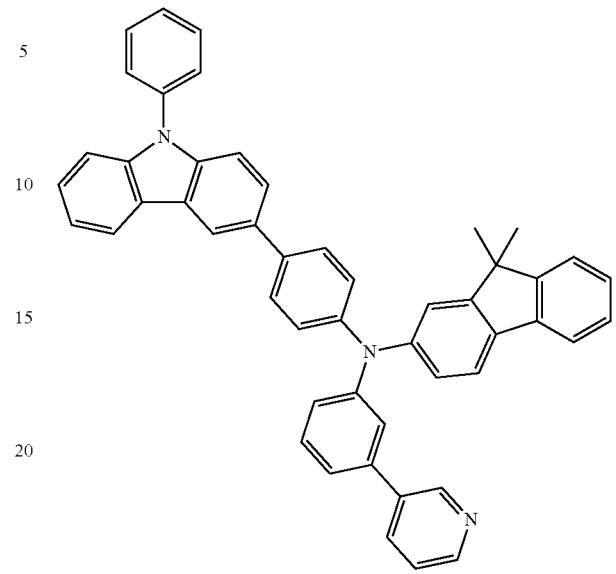
HT12
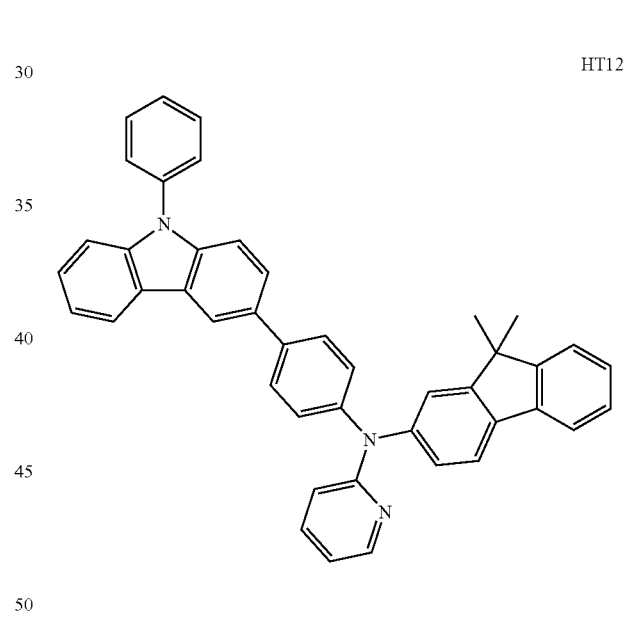
HT13
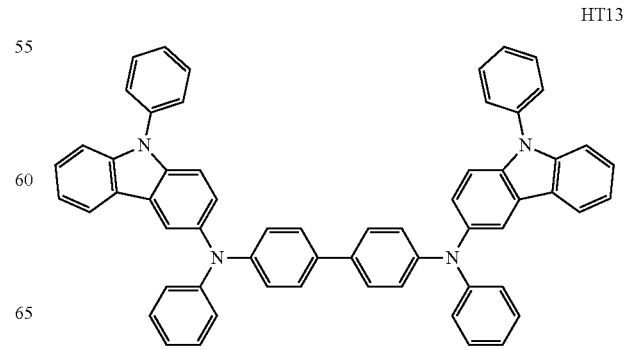

HT14

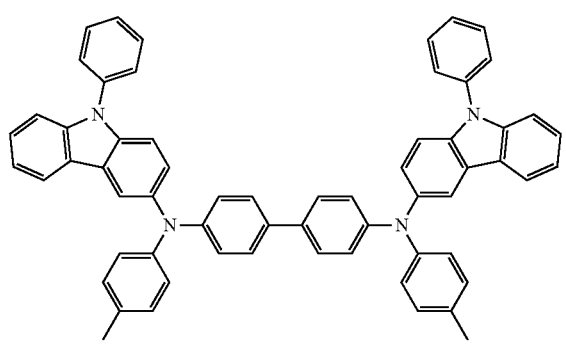

HT15

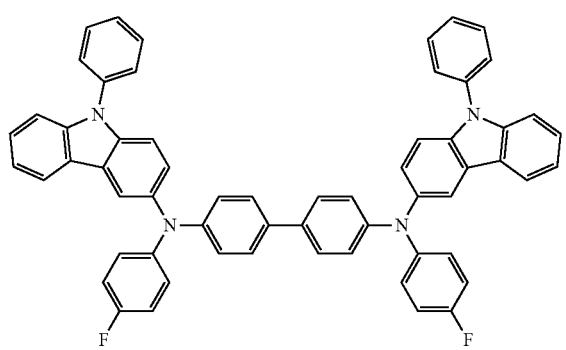

HT16

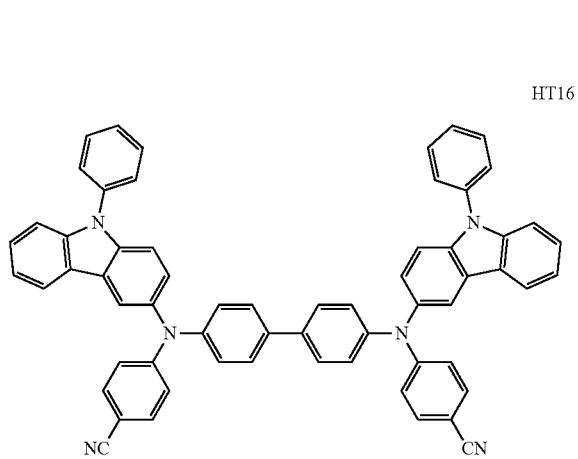

HT17

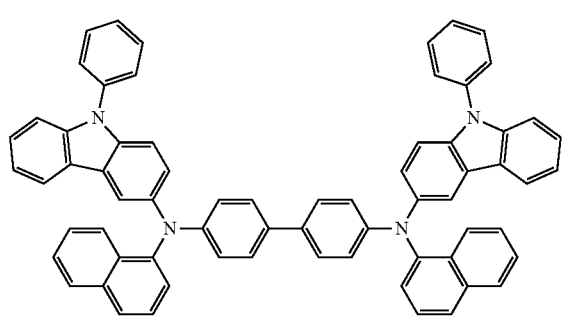

HT18

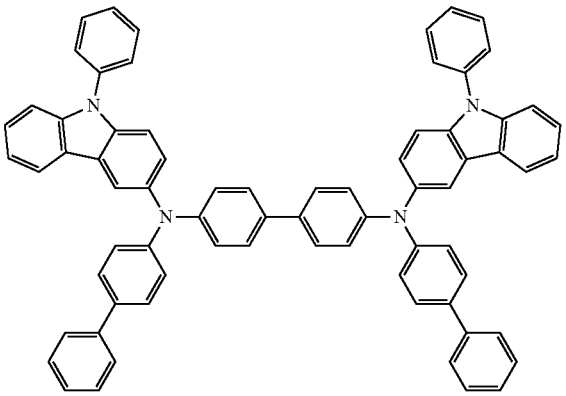

HT19

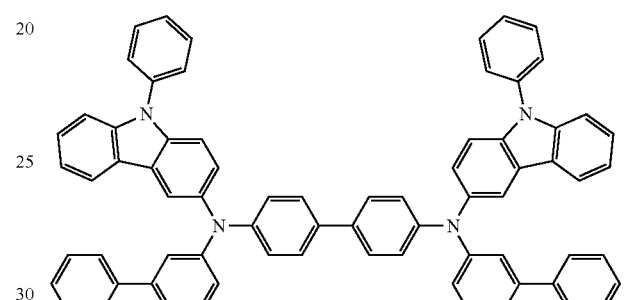

HT20

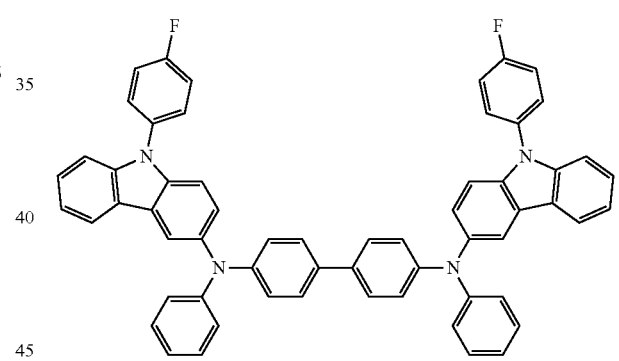

A thickness of the hole transport region may be in a range of about 100 Å to about 10,000 Å, for example, about 100 Å to about 1,000 Å. While not wishing to be bound by a theory, it is understood that when the hole transport region includes both an HIL and an HTL, a thickness of the HIL may be in a range of about 100 Å to about 10,000 Å, and, for example, about 100 Å to about 1,000 Å, and a thickness of the HTL may be in a range of about 50 Å to about 2,000 Å and, for example, about 100 Å to about 1,500 Å. While not wishing to be bound by a theory, it is understood that when thicknesses of the hole transport region, the HIL, and the HTL are within these ranges described above, hole transporting properties may be suitable or satisfactory without a substantial increase in driving voltage.

The hole transport region may further include, in addition to the materials described above, a charge-generating material to improve conductive properties. The charge-generating material may be homogeneously or non-homogeneously dispersed throughout the hole transport region.

The charge-generating material may be, for example, a p-dopant. The p-dopant may be one of a quinone derivative, a metal oxide, and a cyano (—CN) group-containing compound, but embodiments are not limited thereto. For example, non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a cyano (—CN) group-containing group, such as Compounds HT-D1 and HT-D2, but embodiments are not limited thereto.

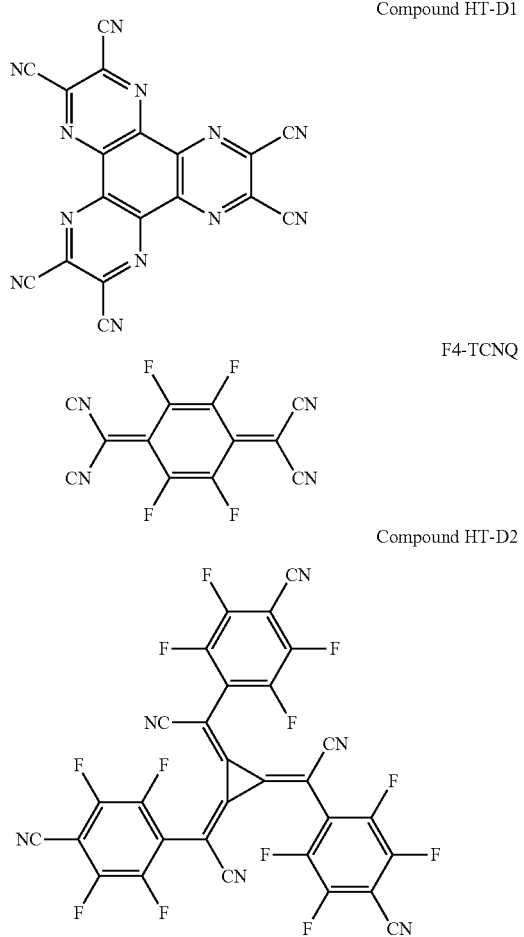

Compound HT-D1

F4-TCNQ

Compound HT-D2

The hole transport region may further include a buffer layer.

The buffer layer may compensate for an optical resonance distance of light according to a wavelength of the light emitted from the emission layer.

The emission layer may be formed on the hole transport region by using various suitable methods, such as vacuum deposition, spin coating, or a LB method. When the emission layer is formed by vacuum deposition or by spin coating, the deposition conditions or the coating conditions may be varied according to compounds used as the material for forming the HIL, but may be the same or substantially the same as the deposition conditions or the coating conditions for forming the HIL.

The hole transport region may further include an EBL. The EBL may include a known material, e.g., mCP, but embodiments are not limited thereto.

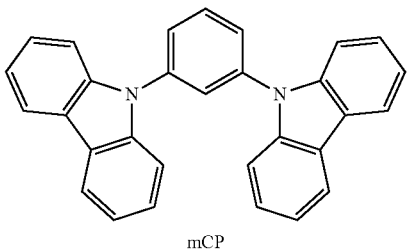 [SMILES: c1cc(-n2c3ccccc3c3ccccc32)cc(-n2c3ccccc3c3ccccc32)c1]

mCP

When the organic light-emitting device 10 is a full-color organic light-emitting device, the emission layer may be patterned into a red emission layer, a green emission layer, and a blue emission layer. Alternatively, the emission layer may have a stacked structure of a red emission layer, a green emission layer, and/or a blue emission layer, to thereby emit white light.

The emission layer may include the condensed cyclic compound of Formula 1, and may further include a dopant. The dopant may include at least one of a phosphorescent dopant and a fluorescent dopant.

For example, the host included in the emission layer may include the condensed cyclic compound of Formula 1.

The dopant included in the emission layer may include a fluorescent dopant that emits light according to a fluorescent emission mechanism or a phosphorescent dopant that emits light according to a phosphorescent emission mechanism.

In an exemplary embodiment, the dopant included in the emission layer may include a phosphorescent dopant, and the phosphorescent dopant may include an organometallic compound represented by Formula 81:

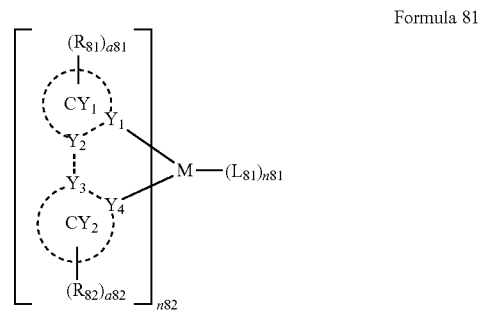

Formula 81

In Formula 81,

M may be iridium (Ir), platinum (Pt), osmium (Os), titanium (Ti), zirconium (Zr), hafnium (Hf), europium (Eu), terbium (Tb), or thulium (Tm), $Y_1$ to $Y_4$ may each be independently C or N, $Y_1$ and $Y_2$ may be linked to each other via a single bond or a double bond, and $Y_3$ and $Y_4$ may be linked to each other via a single bond or a double bond, $CY_1$ and $CY_2$ may each be independently a benzene, a naphthalene, a fluorene, a spiro-fluorene, an indene, a pyrrole, a thiophene, a furan, an imidazole, a pyrazole, a thiazole, an isothiazole, an oxazole, an isoxazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiophene, an isobenzothiophene, a benzoxazole, an isobenzoxazole, a triazole, a tetrazole, an oxadiazole, a triazine, a dibenzofuran, or a dibenzothiophene, wherein $CY_1$ and $CY_2$ may be optionally linked to each other via a single bond or an organic linking group, $R_{81}$ and $R_{82}$ may each be independently a hydrogen, a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$) or —B(Q$_6$)(Q$_7$), a81 and a82 may each be independently selected from integers of 1 to 5, n81 may be selected from integers of 0 to 4, n82 may be 1, 2, or 3, and $L_{81}$ may be a monovalent organic ligand, a divalent organic ligand, or a trivalent organic ligand.

Descriptions of $R_{81}$ and $R_{82}$ may be each independently as referred to in the description provided in connection with $R_{41}$ above.

The phosphorescent dopant may include at least one of Compounds PD1 to PD78 and FIr6, but the phosphorescent dopant is not limited thereto:

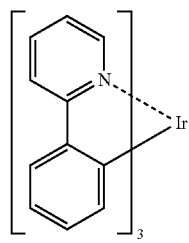

PD1

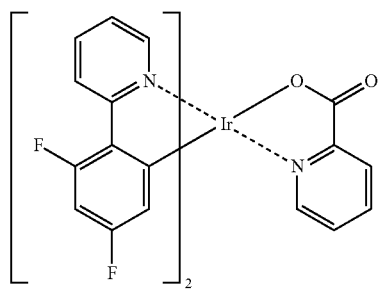

PD2

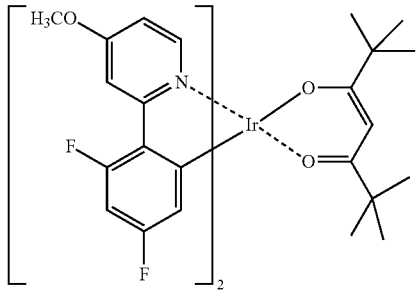

PD3

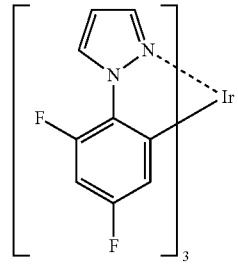

PD4

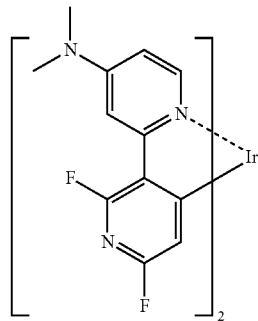

PD5

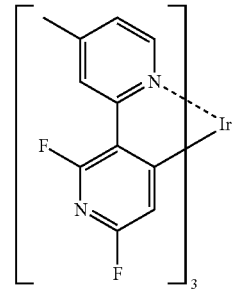

PD6

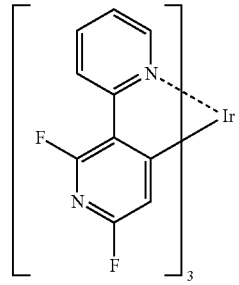

PD7

-continued
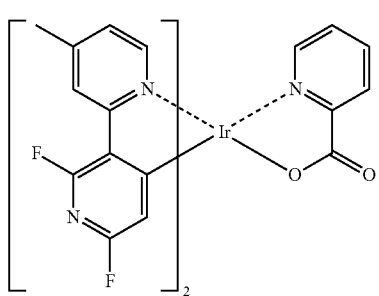
PD8
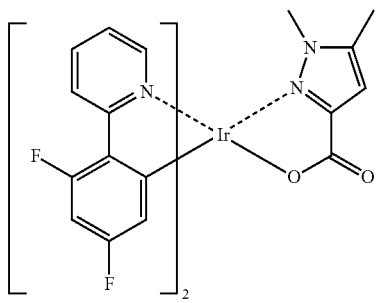
PD13
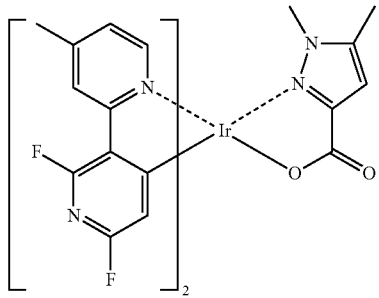
PD9
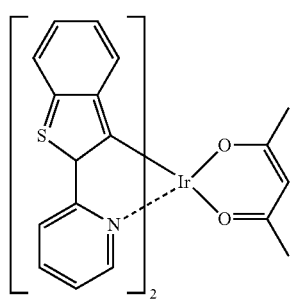
PD14
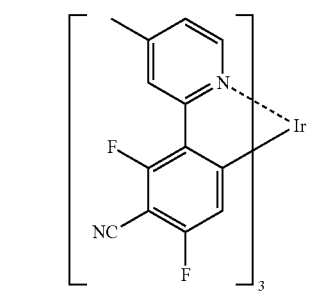
PD10
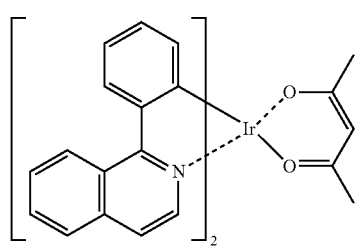
PD15
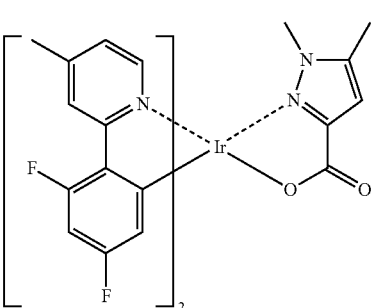
PD11
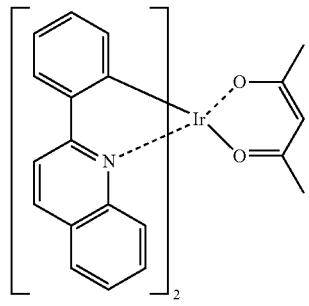
PD16
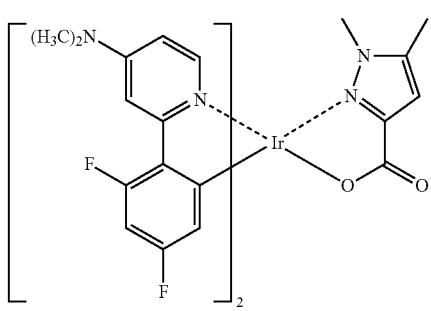
PD12
PD17

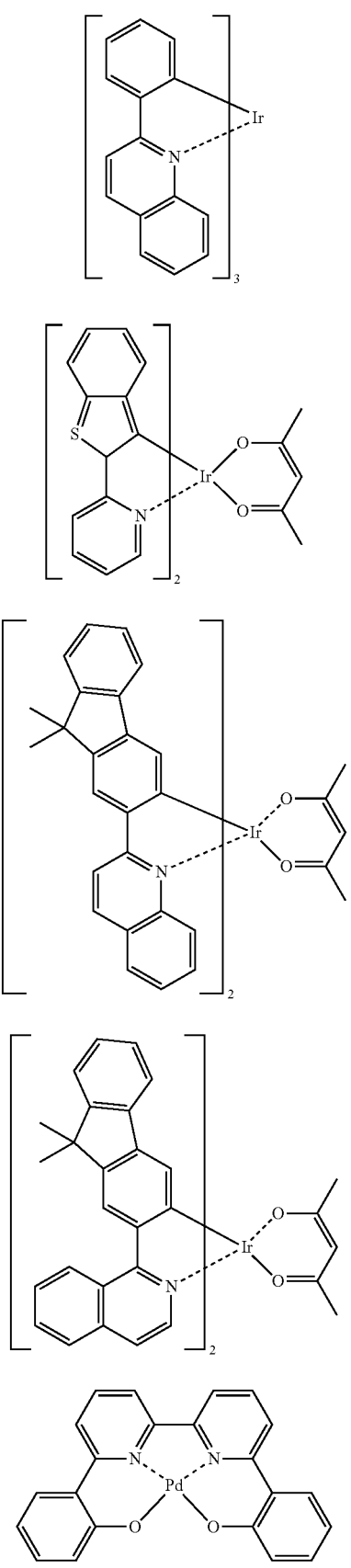

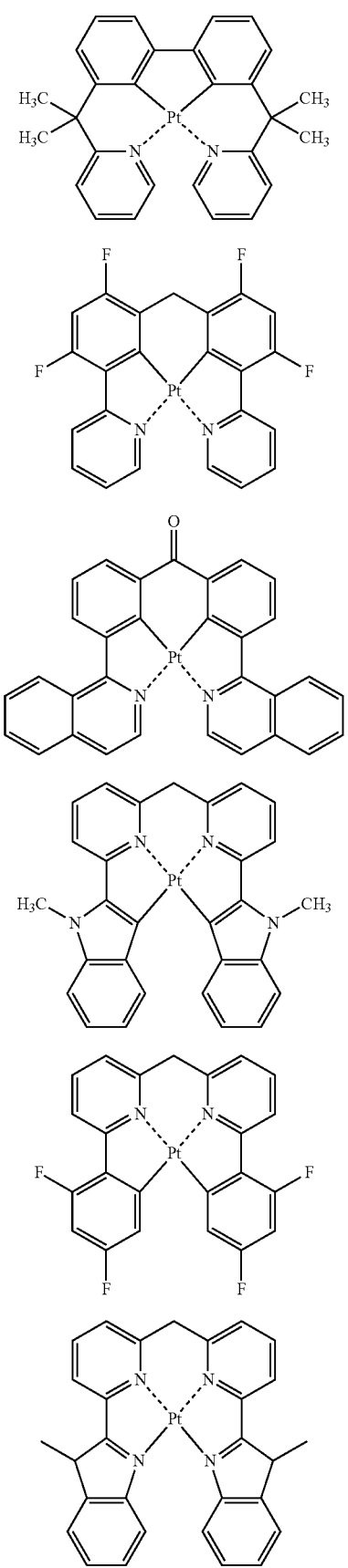
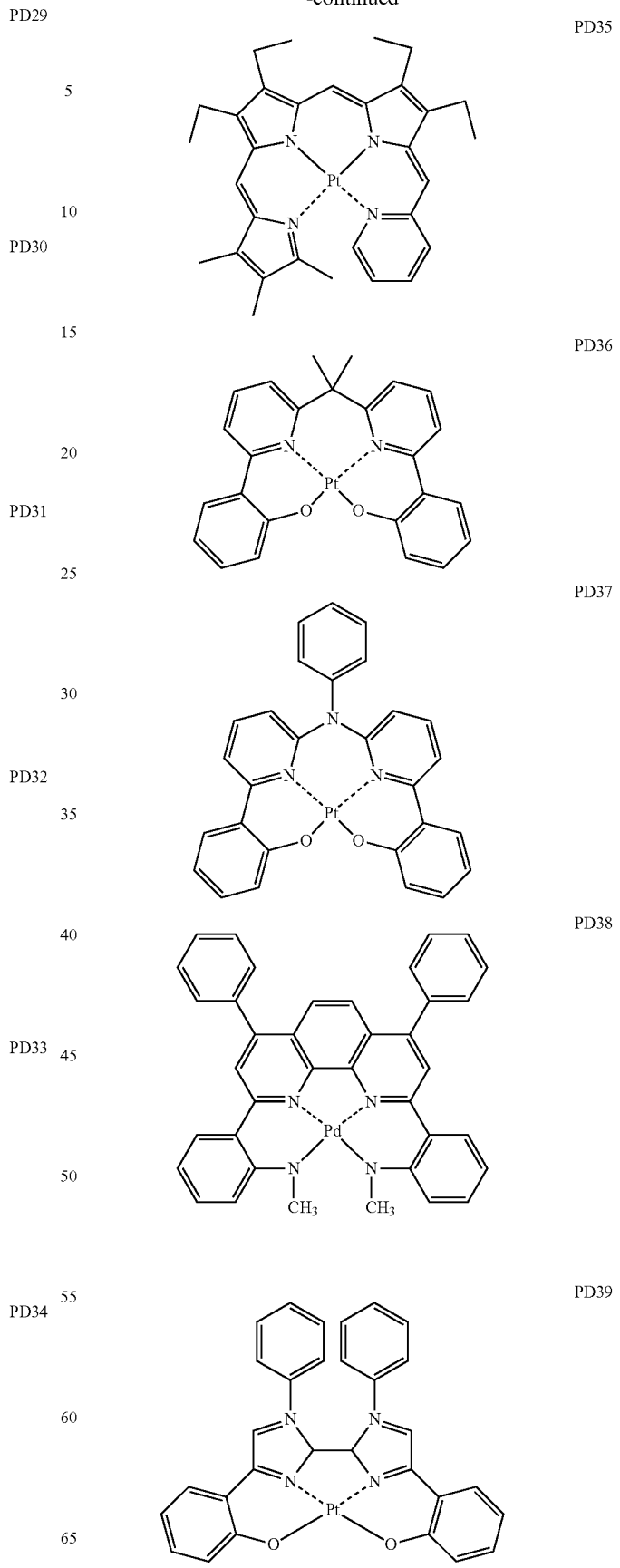

PD40 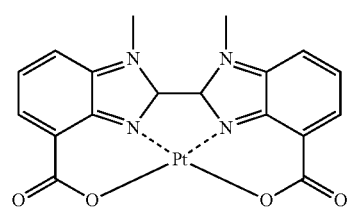
PD41 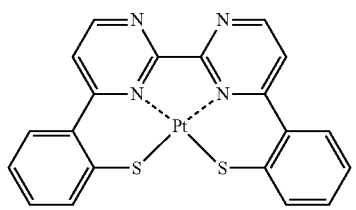
PD42 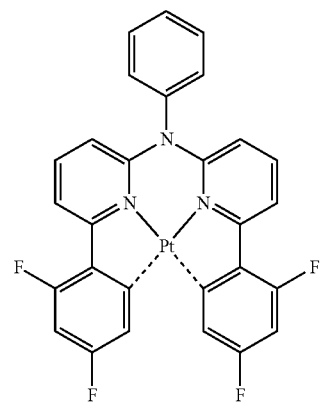
PD43 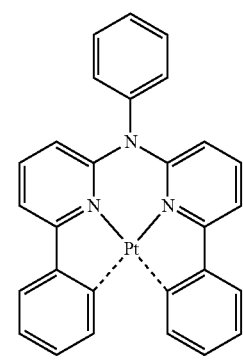
PD44 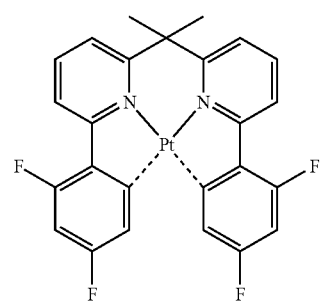
PD45 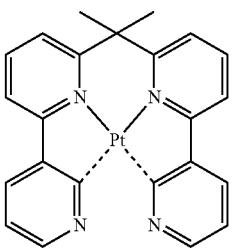
PD46 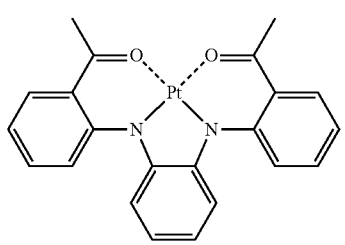
PD47 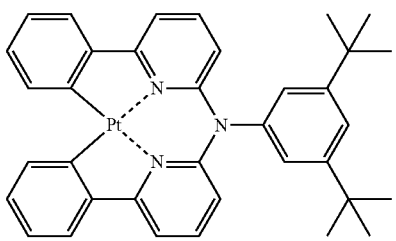
PD48 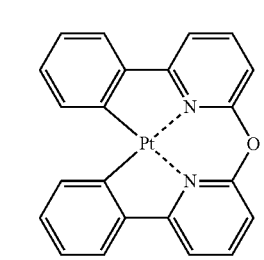
PD49 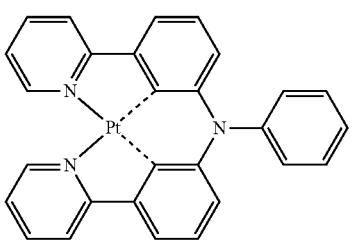
PD50 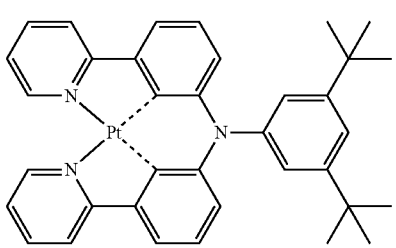

PD51 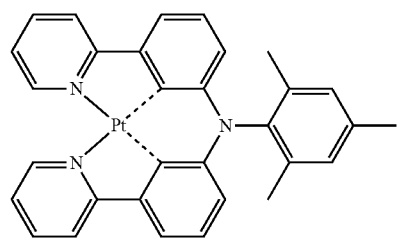
PD52 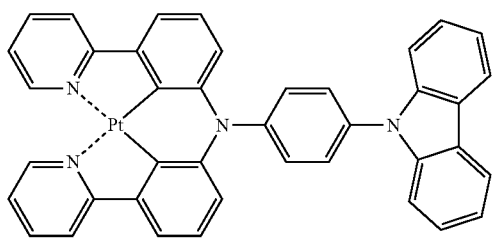
PD53 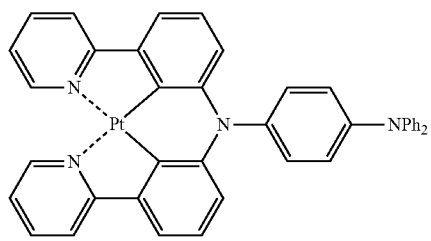
PD54 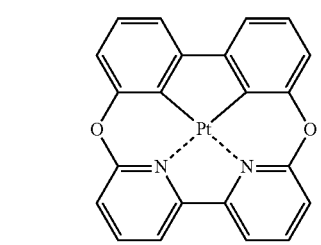
PD55 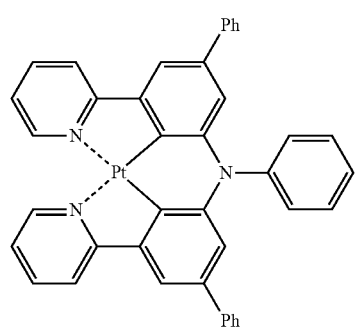
PD56 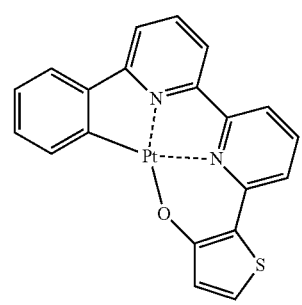
PD57 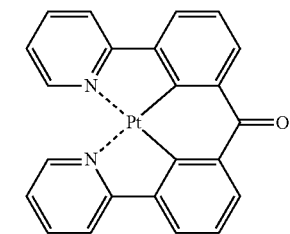
PD58 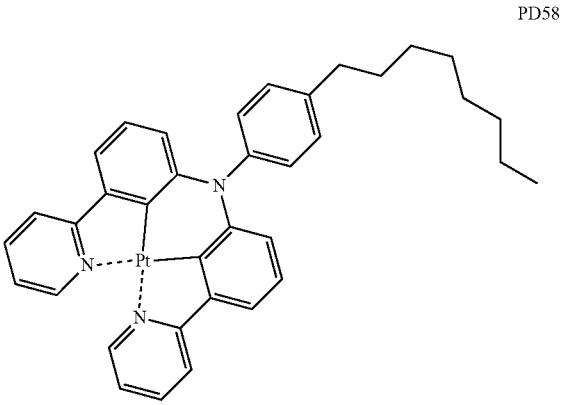
PD59 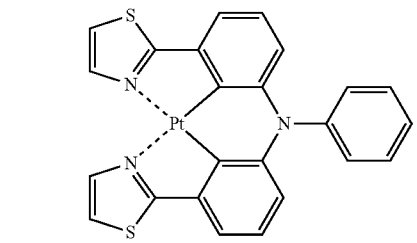
PD60 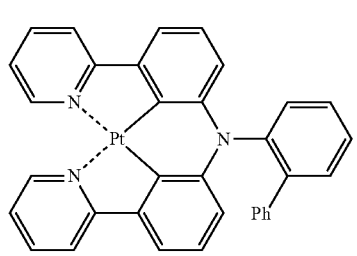
PD61 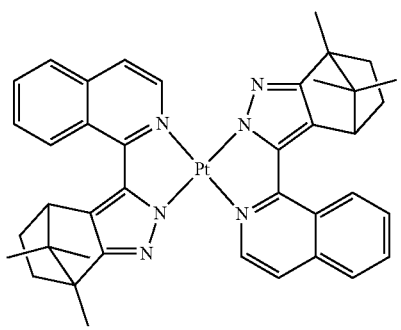

PD62 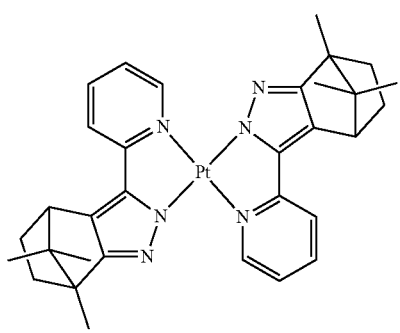
PD63 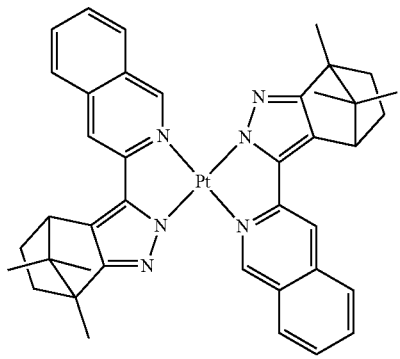
PD64 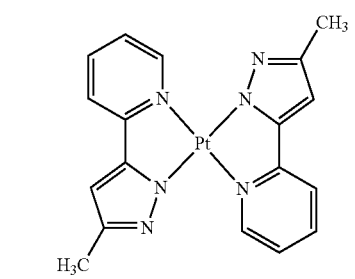
PD65 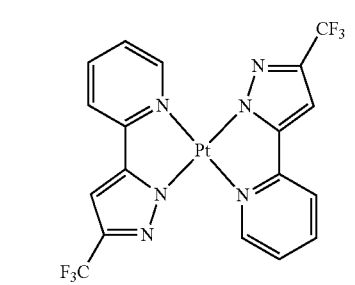
PD66 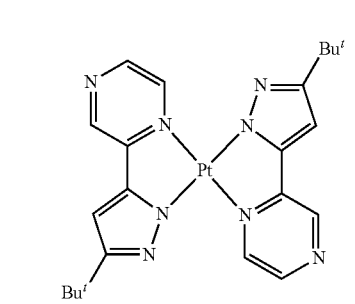
PD67 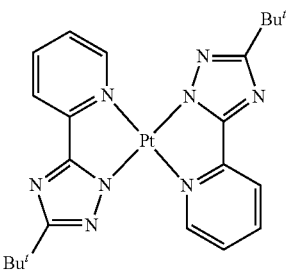
PD68 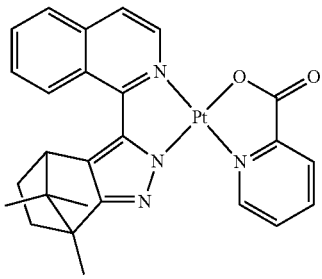
PD69 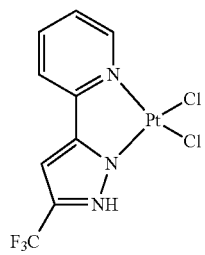
PD70 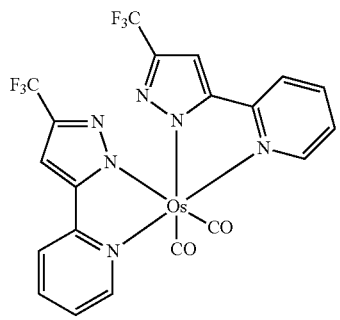
PD71 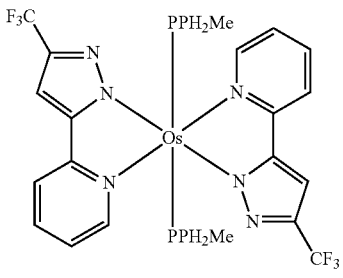

PD72 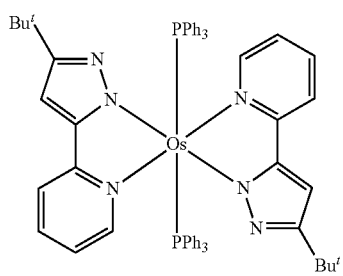

PD73 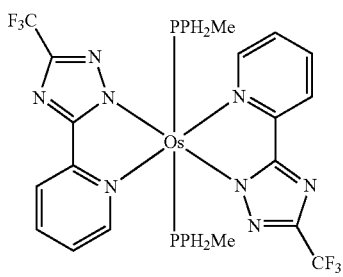

PD74 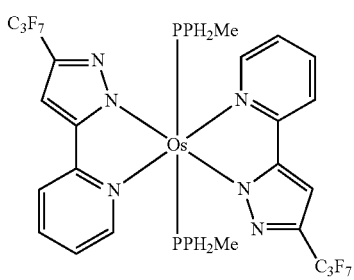

PD75 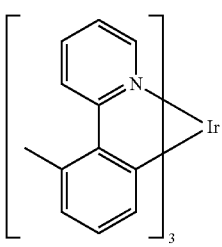

PD76 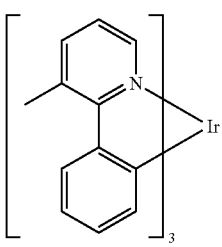

PD77 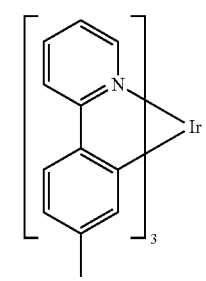

PD78 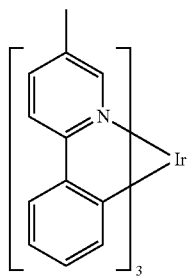

FIr6 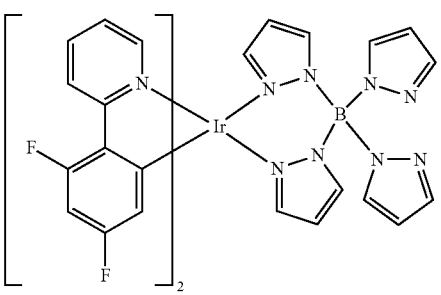

Alternatively, the phosphorescent dopant may include PtOEP:

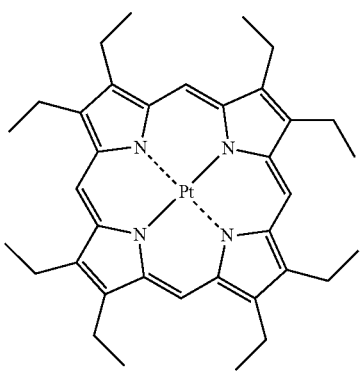

PtOEP

When the emission layer includes a host and a dopant, an amount of the dopant may be in a range of about 0.01 to about 20 parts by weight based on 100 parts by weight of the host, but the amount of the dopant is not limited thereto.

A thickness of the emission layer may be in a range of about 100 Å to about 1,000 Å, e.g., about 200 Å to about 600 Å. While not wishing to be bound by a theory, it is understood that when the thickness of the emission layer is within these ranges, excellent emission characteristics may be obtained without a substantial increase in driving voltage.

Next, the electron transport region may be disposed on the emission layer.

The electron transport region may include at least one of an HBL, an ETL, and an EIL.

For example, the electron transport region may have a structure of HBL/ETL/EIL or a structure of ETL/EIL, but the structure of the electron transport region is not limited thereto. The electron transport layer may have a single-layer structure of a multi-layer structure including two or more materials that are different from each other.

Conditions for forming an HBL, an ETL, and an EIL included in the electron transport region may be inferred based on the conditions for forming the HIL.

When the electron transport region includes an HBL, the HBL may include, for example, at least one of BCP and Bphen, but embodiments are not limited thereto.

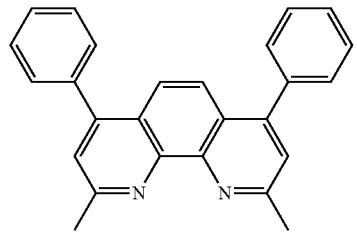

BCP

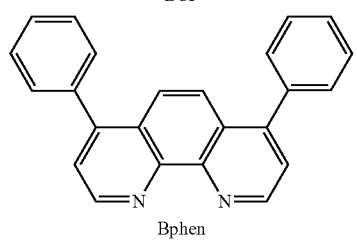

Bphen

A thickness of the HBL may be in a range of about 20 Å to about 1,000 Å, e.g., about 30 Å to about 300 Å. While not wishing to be bound by a theory, it is understood that when the thickness of the HBL is within these ranges, excellent hole blocking characteristics may be obtained without a substantial increase in driving voltage.

The ETL may further include at least one of BCP and Bphen above and Alq$_3$, Balq, TAZ, and NTAZ:

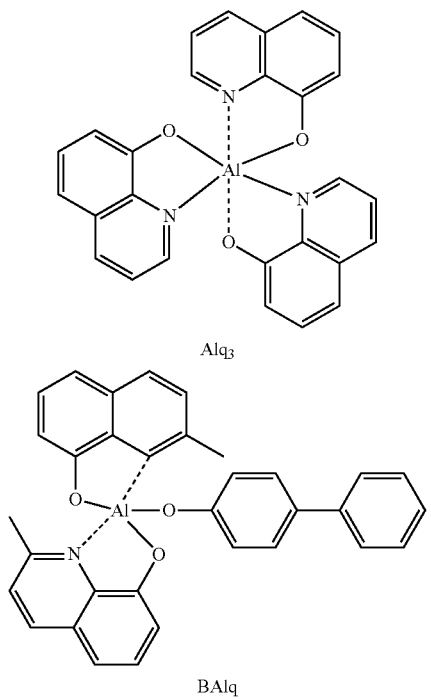

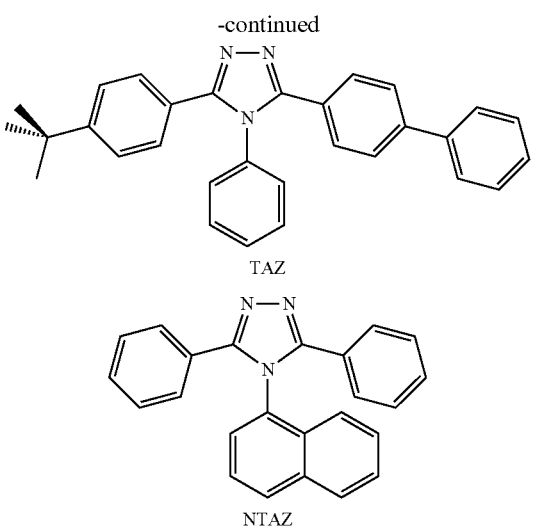

TAZ

NTAZ

Alternatively, the ETL may include at least one of Compounds ET1 to ET19, but embodiments are not limited thereto.

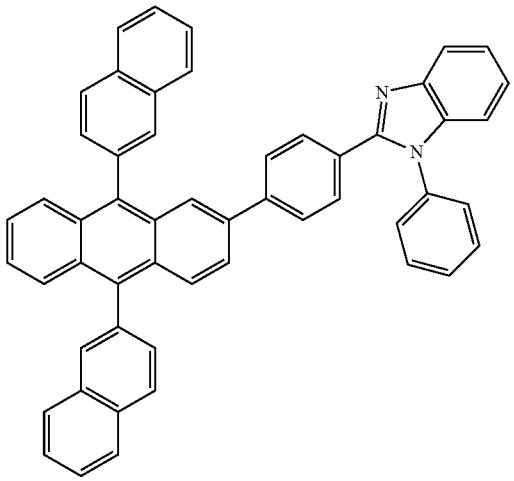

ET1

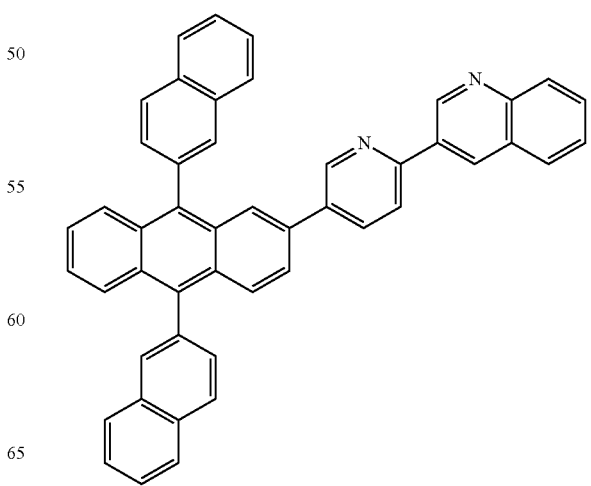

ET2

-continued
ET3
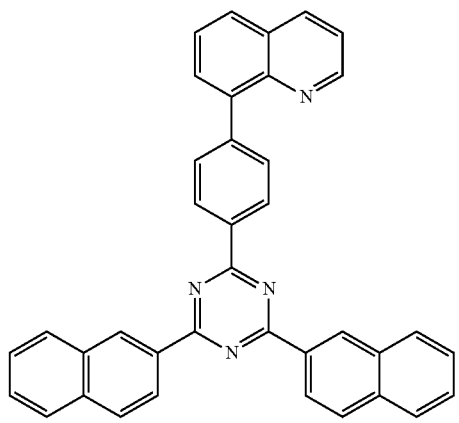
ET4
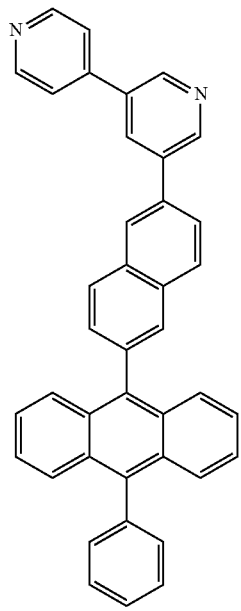
ET5
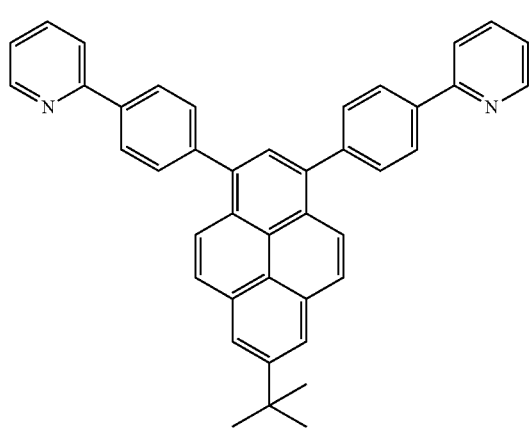
-continued
ET6
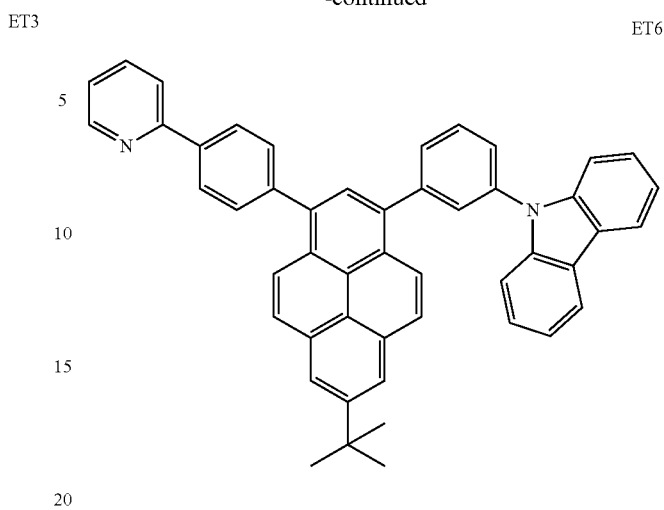
ET7
ET8
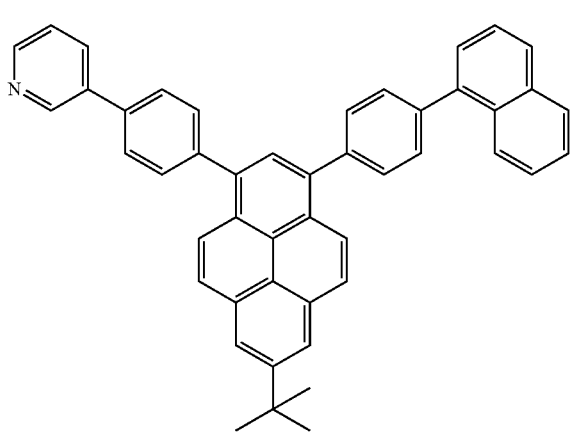

-continued
ET9
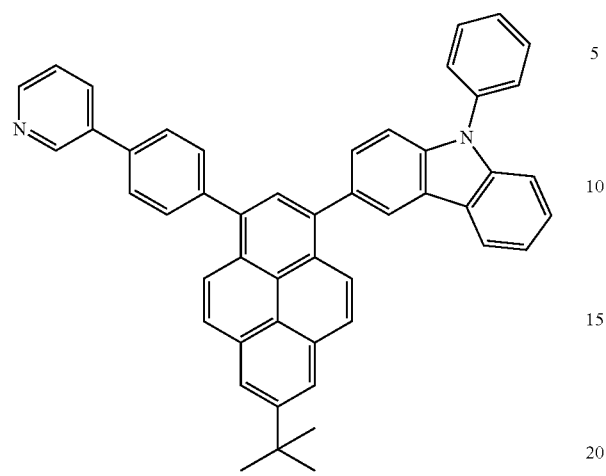
ET10
ET11
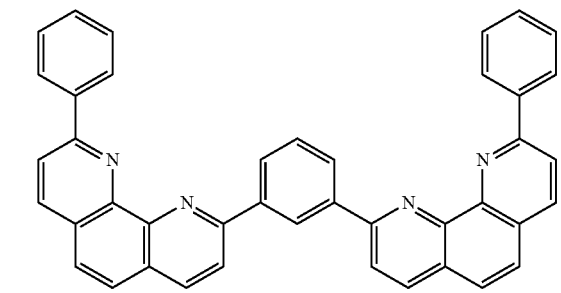
ET12
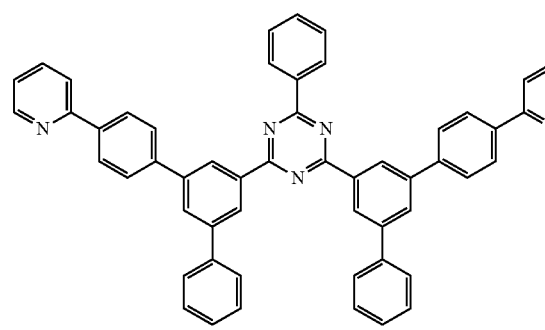
ET13
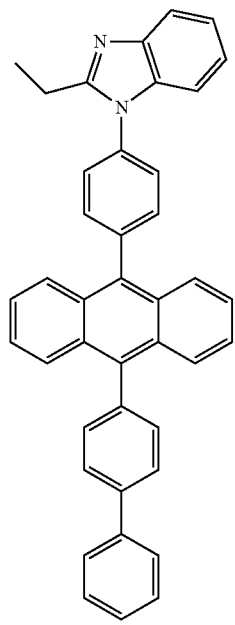
ET14
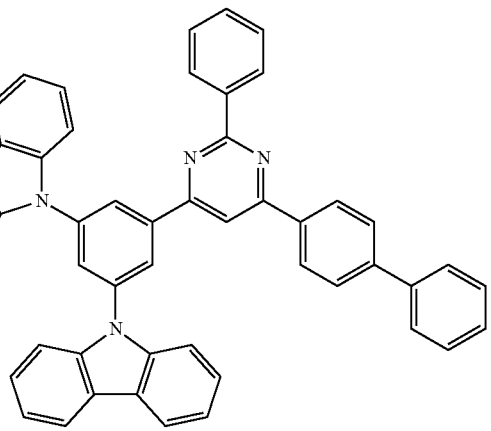
ET15
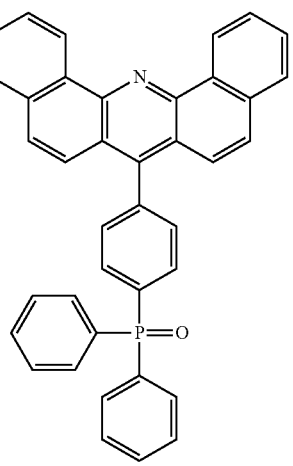

ET16
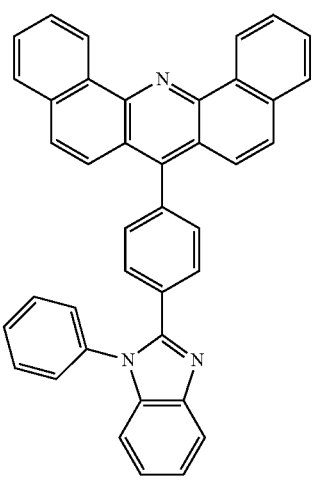

ET17
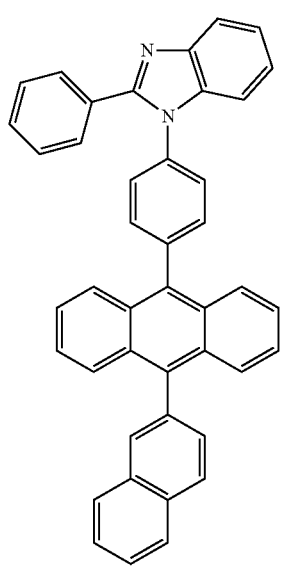

ET18
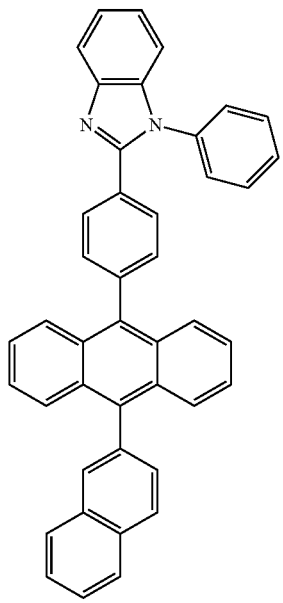

ET19
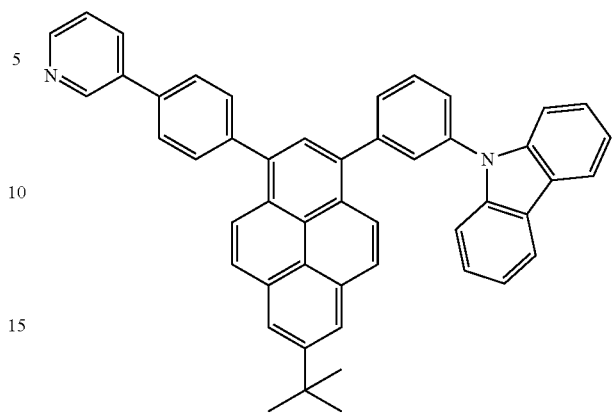

A thickness of the ETL may be in a range of about 100 Å to about 1,000 Å, e.g., about 150 Å to about 500 Å. When the thickness of the ETL is within these ranges, excellent electron transporting characteristics may be obtained without a substantial increase in driving voltage.

The ETL may include, in addition to the materials described above, a metal-containing material.

The metal-containing material may include a Li complex. The Li complex may include, for example, Compound ET-D1 (e.g., lithium quinolate (LiQ)) or Compound ET-D2:

ET-D1
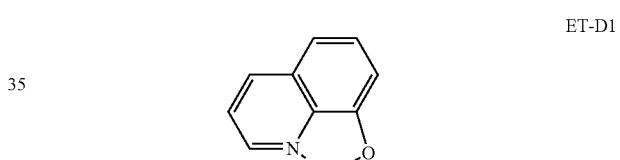

ET-D2
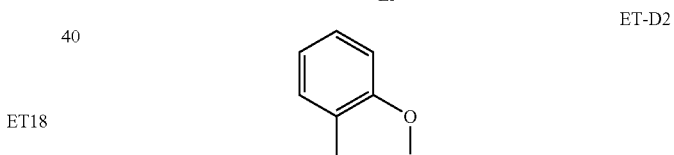

In addition, the electron transport region may include an EIL that facilitates electron injection from the second electrode 19.

The EIL may include at least one selected from LiF, NaCl, CsF, $Li_2O$, and BaO.

A thickness of the EIL may be in a range of about 1 Å to about 100 Å, e.g., about 3 Å to about 90 Å. When the thickness of the EIL is within these ranges, suitable or satisfactory electron injecting characteristics may be obtained without a substantial increase in driving voltage.

The second electrode 19 may be disposed on the organic layer 15. When the second electrode 19 is a cathode, a material for forming the second electrode 19 may be a material having a relatively low work function, such as a metal, an alloy, an electrically conductive compound, or a mixture thereof. Detailed examples of the material for forming the second electrode 10 may include Li, Mg, Al, Al—Li, Ca, Mg—In, and Mg—Ag. Alternatively, the material for forming the second electrode 19 may include ITO or IZO to manufacture a top-emission organic light-emitting device.

Hereinbefore, the organic light-emitting device 10 is described in connection with FIG. 1, but embodiments are not limited thereto.

A $C_1$-$C_{60}$ alkyl group as used herein refers to a linear or branched aliphatic hydrocarbon monovalent group having 1 to 60 carbon atoms. Detailed examples thereof include a methyl group, an ethyl group, a propyl group, an isobutyl group, a sec-butyl group, a tert-butyl group, a pentyl group, an iso-amyl group, and a hexyl group. A $C_1$-$C_{60}$ alkylene group as used herein refers to a divalent group having the same structure as the $C_1$-$C_{60}$ alkyl group.

A $C_1$-$C_{60}$ alkoxy group as used herein refers to a monovalent group represented by —$OA_{101}$ (wherein $A_{101}$ is the $C_1$-$C_{60}$ alkyl group). Detailed examples thereof include a methoxy group, an ethoxy group, and an isopropyloxy group.

A $C_2$-$C_{60}$ alkenyl group as used herein refers to a hydrocarbon group formed by placing at least one carbon double bond in a middle or terminal end of the $C_2$-$C_{60}$ alkyl group. Detailed examples thereof include an ethenyl group, a propenyl group, and a butenyl group. A $C_2$-$C_{60}$ alkenylene group as used herein refers to a divalent group having the same structure as the $C_2$-$C_{60}$ alkenyl group.

A $C_2$-$C_{60}$ alkynyl group as used herein refers to a hydrocarbon group formed by placing at least one carbon triple bond in a middle or terminal end of the $C_2$-$C_{60}$ alkyl group. Detailed examples thereof are an ethynyl group and a propynyl group. A $C_2$-$C_{60}$ alkynylene group as used herein refers to a divalent group having the same structure as the $C_2$-$C_{60}$ alkynyl group.

A $C_3$-$C_{10}$ cycloalkyl group as used herein refers to a monovalent hydrocarbon monocyclic group having 3 to 10 carbon atoms. Detailed examples thereof include cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as the $C_3$-$C_{10}$ cycloalkyl group.

A $C_1$-$C_{10}$ heterocycloalkyl group as used herein refers to a N monovalent monocyclic group having at least one heteroatom selected from N, O, P, and S as a ring-forming atom and 1 to 10 carbon atoms. Detailed examples thereof include a tetrahydrofuranyl group and a tetrahydrothiophenyl group. A $C_1$-$C_{10}$ heterocycloalkylene group as used herein refers to a divalent group having the same structure as the $C_1$-$C_{10}$ heterocycloalkyl group.

A $C_3$-$C_{10}$ cycloalkenyl group as used herein refers to a monovalent monocyclic group that has 3 to 10 carbon atoms and at least one double bond in the ring thereof, and which is not aromatic. Detailed examples thereof include a cyclopentenyl group, a cyclohexenyl group, and a cycloheptenyl group. A $C_3$-$C_{10}$ cycloalkenylene group as used herein refers to a divalent group having the same structure as the $C_3$-$C_{10}$ cycloalkenyl group.

A $C_1$-$C_{10}$ heterocycloalkenyl group as used herein refers to N a monovalent monocyclic group that has at least one heteroatom selected from N, O, P, and S as a ring-forming atom, 1 to 10 carbon atoms, and at least one double bond in the ring. Detailed examples of the $C_1$-$C_{10}$ heterocycloalkenyl group include 2,3-dihydrofuranyl group and 2,3-dihydrothiophenyl group. A $C_1$-$C_{10}$ heterocycloalkenylene group as used herein refers to a divalent group having the same structure as the $C_1$-$C_{10}$ heterocycloalkenyl group.

A $C_6$-$C_{60}$ aryl group as used herein refers to a monovalent group having a carbocyclic aromatic system having 6 to 60 carbon atoms, and a $C_6$-$C_{60}$ arylene group as used herein refers to a divalent group having a carbocyclic aromatic system having 6 to 60 carbon atoms. Detailed examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, these rings may be fused to each other.

A $C_1$-$C_{60}$ heteroaryl group as used herein refers to a monovalent group having a carbocyclic aromatic system that has at least one heteroatom selected from N, O, P, and S as a ring-forming atom, and 1 to 60 carbon atoms. A $C_1$-$C_{60}$ heteroarylene group as used herein refers to a divalent group having a carbocyclic aromatic system that has at least one heteroatom selected from N, O, P, and S as a ring-forming atom, and 1 to 60 carbon atoms. Detailed examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, these rings may be fused to each other.

A $C_6$-$C_{60}$ aryloxy group as used herein indicates —$OA_{102}$ (wherein $A_{102}$ is the $C_6$-$C_{60}$ aryl group), and a $C_6$-$C_{60}$ arylthio group as used herein indicates —$SA_{103}$ (wherein $A_{103}$ is the $C_6$-$C_{60}$ aryl group).

A monovalent non-aromatic condensed polycyclic group (e.g., a group having 8 to 60 carbon atoms) as used herein refers to a monovalent group that has two or more rings condensed to each other, has carbon atoms only as a ring-forming atom, and which is non-aromatic in the entire molecular structure. A detailed example of the non-aromatic condensed polycyclic group includes a fluorenyl group. A divalent non-aromatic condensed polycyclic group as used herein refers to a divalent group having the same structure as the monovalent non-aromatic condensed polycyclic group.

A monovalent non-aromatic condensed heteropolycyclic group (e.g., a group having 1 to 60 carbon atoms) as used herein refers to a monovalent group that has two or more rings condensed to each other, has heteroatoms as a ring-forming atom selected from N, O, P, and S, in addition to C, and which is non-aromatic in the entire molecular structure. A detailed example of the monovalent non-aromatic condensed heteropolycyclic group includes a carbazolyl group. A divalent non-aromatic condensed heteropolycyclic group as used herein refers to a divalent group having the same structure as the monovalent non-aromatic condensed heteropolycyclic group.

At least one of substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, a substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

a deuterium, —F, —Cl, —Br, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{31}$)($Q_{32}$)($Q_{33}$), wherein $Q_1$ to $Q_3$, $Q_{11}$ to $Q_{13}$, $Q_{21}$ to $Q_{23}$, and $Q_{31}$ to $Q_{33}$ may each be independently selected from a hydrogen, a $C_1$-$C_{60}$ alkyl group, a $C_1$-$C_{60}$ alkoxy group, a $C_3$-$C_{13}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

When a group containing a specified number of carbon atoms is substituted with any of the substituents listed above, the number of carbon atoms in the resulting "substituted" group may be the number of atoms contained in the original (base) group plus the number of carbon atoms (if any) contained in the substituent. For example, the "substituted $C_1$-$C_{30}$ alkyl" may refer to a $C_1$-$C_{30}$ alkyl group substituted with $C_{6-60}$ aryl group, in which the total number of carbon atoms may be $C_7$-$C_{90}$.

As used herein, the term "biphenyl group" refers to "a phenyl group substituted with a phenyl group".

Hereinafter, a compound and an organic light-emitting device according to an embodiment will be described in detail with reference to Synthesis Examples and Examples. However, these examples are only for illustrative purposes and are not intended to limit the scope of the one or more embodiments of the present inventive concept. In the following synthesis examples, the expression "'B' instead of 'A' was used" or "'B' instead of 'A' was included" indicates that 'B' and 'A' were included in equivalent amounts.

EXAMPLES

Synthesis Example 1: Synthesis of Compound 3

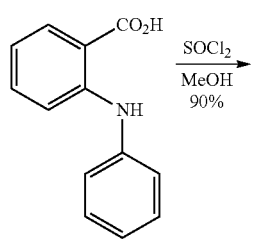

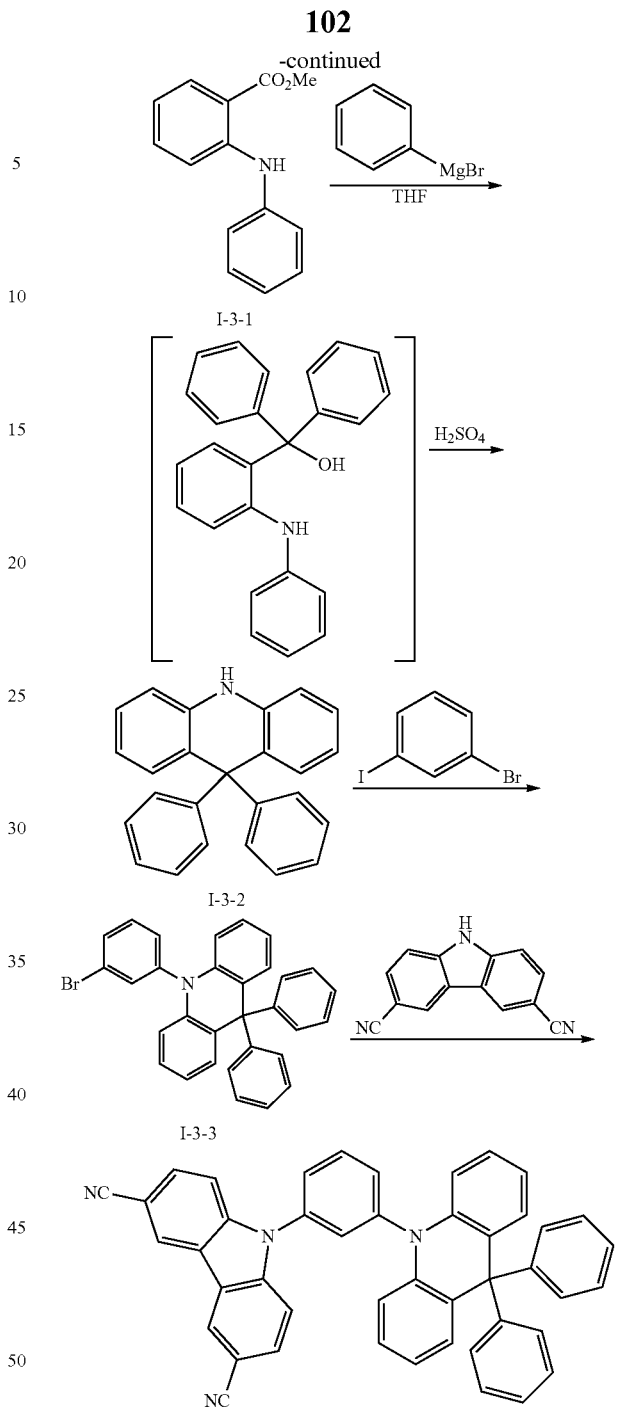

1) Synthesis of Intermediate I-3-1

2.5 grams (g) (0.12 moles (mol)) of 2-(phenylamino)benzoic acid, 1.39 g (0.13 mol) of thionyl chloride, and 50 milliliters (ml) of methanol were added to a flask, and these reactants were allowed to react for 5 hours. After the reaction was completed, the reaction mixture was filtered to obtain solid products. Then, the solid products were washed out with water, thereby obtaining 2.4 g (yield: 90%) of Intermediate I-3-1.

2) Synthesis of Intermediate I-3-2

A Grignard reaction was prepared by using 2 g (0.009 mol) of Intermediate I-3-1 and 2.07 g (0.012 mol) of phenyl magnesium bromide, to obtain diphenyl(2-(phenylamino)phenyl)methanol. 30 ml of sulfuric acid was added thereto without separation of diphenyl(2-(phenylamino)phenyl)methanol, thereby obtaining 1.6 g (yield: 56%) of Intermediate I-3-2.

3) Synthesis of Intermediate I-3-3

24 g (72 mmol) of Intermediate I-3-2, 24 g (86 mmol) of 1-bromo-3-iodobenzene, 0.685 g (3.6 mmol) of copper iodide, 13.83 g (143.96 mmol) of sodium tert-butoxide, 1,644 g (14.40 mmol) of trans-1,2-diaminocyclohexane, and 150 ml of 1,4-dioxane were allowed to react at a temperature of 100° C. for 12 hours. After the reaction mixture was cooled to room temperature, methanol was added thereto to produce precipitates that were subsequently separated by a filter. The separated precipitates were purified using column chromatography, thereby obtaining 20.2 g (yield: 58%) of Intermediate I-3-3.

4) Synthesis of Compound 3

5 g (23 mmol) of 3,6-dicyano-9H-carbazole, 13.4 g (27.62 mmol) of Intermediate I-3-3, 2,192 g (11.51 mmol) of copper iodide, 6.362 g (46 mmol) of potassium carbonate, 4.148 g (23 mmol) of 1,10-phenanthroline, and 120 ml of dimethylformamide were allowed to react for 24 hours. The crude products obtained therefrom were purified using column chromatography using dichloromethane:n-hexane (primary purification). The purified products obtained from the primary purification were recrystallized with ethylacetate and ethanol, thereby obtaining 3.74 g (yield: 26%) of a final purified product, i.e., Compound 3. This compound was identified using LC-Mass.

LC-Mass (calculated: 624.23 g/mol. found: M+H=625 grams per mole (g/mol)).

Synthesis Example 2: Synthesis of Compound 4

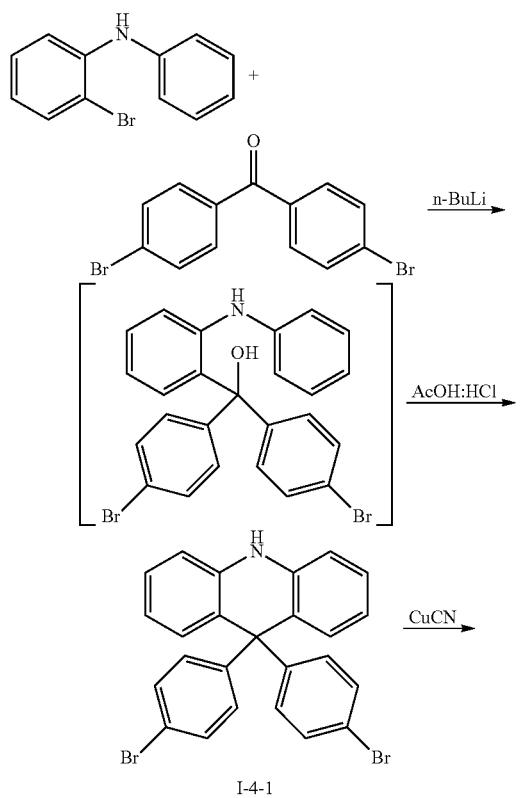

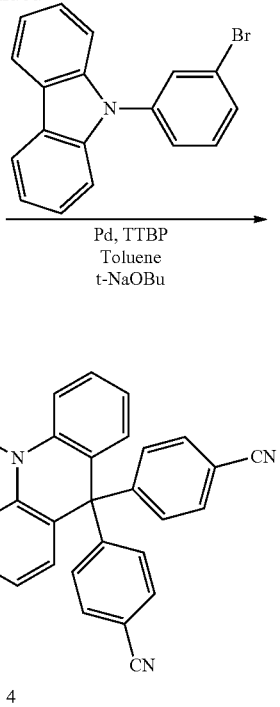

1) Synthesis of Intermediate I-4-1

10 g (42 mmol) of 2-bromo-N-phenylaniline and 150 ml of tetrahydrofuran were added to a reaction container, and the mixture was cooled to −78'C using dry ice. After 3.323 g (52 mmol) of n-butyllithium was slowly dropwise added thereto, the resulting solution was stirred for 1 hour. 17.6 g (52 mmol) of bis(4-bromophenyl)methanone was dissolved in 50 ml of tetrahydrofuran, and slowly dropwise added to the reaction container. After the reaction was completed, the solvent was evaporated and the resulting residue was thoroughly dried. 100 ml of acetic acid:hydrochloric acid (1:10 volume by volume (v/v)) was added thereto, thereby obtaining 15.2 g (yield: 77%) of Intermediate I-4-1.

2) Synthesis of Intermediate I-4-2

10 g (20 mmol) of Intermediate I-4-1, 7.3 g (81 mmol) of cyano copper, and 50 ml of dimethylformamide were allowed to react for 12 hours at a temperature of 150° C. After the reaction was completed, dichloromethane and water were added thereto, followed by extraction. An organic layer was collected therefrom, and the solvent was evaporated. The resulting residue was purified using column chromatography, thereby obtaining 2.82 g (yield: 36%) of Intermediate I-4-2.

3) Synthesis of Compound 4

5 g (13 mmol) of Intermediate I-4-2, 5.04 g (15.6 mmol) of 9-(3-bromophenyl)-9H-carbazole, 1.24 g (6.52 mmol) of copper iodide, 3.604 g (26 mmol) of potassium carbonate, and 2.35 g (13 mmol) of 1,10-phenanthroline were allowed to react. After the reaction was completed, methanol was added thereto to produce precipitates that were subsequently separated by filtration. The separated precipitates were recrystallized with toluene, thereby obtaining 4.1 g (yield: 51%) of Compound 4. This compound was identified using LC-Mass.

LC-Mass (calculated: 624.23 g/mol. found: MA-H=625 g/mol).

Synthesis Example 3: Synthesis of Compound 16

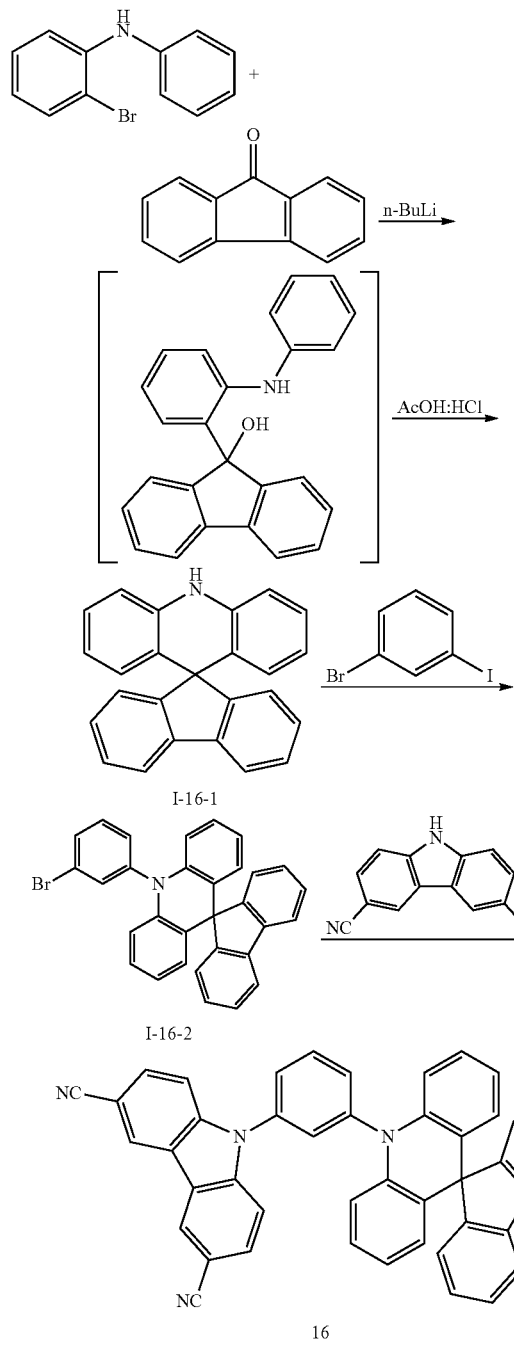

1) Synthesis of Intermediate I-16-1

10 g (42 mmol) of 2-bromo-N-phenylaniline and 150 ml of tetrahydrofuran were added to a reaction container, and the mixture was cooled to −78° C. using dry ice. After 3.323 g (52 mmol) of n-butyllithium was slowly dropwise added thereto, the resulting solution was stirred for 1 hour. 9.4 g (52 mmol) of 9H-fluorene-9-one was dissolved in 50 ml of tetrahydrofuran, and slowly dropwise added to the reaction container. After the reaction was completed, the solvent was evaporated and the resulting residue was thoroughly dried. 100 ml of acetic acid:hydrochloric acid (1:10 v/v) was added thereto, thereby obtaining 11.9 g (89%) of Intermediate I-16-1.

2) Synthesis of Intermediate I-16-2

24 g (72 mmol) of Intermediate I-16-1, 24 g (86 mmol) of 1-bromo-3-iodobenzene, 0.685 g (3.6 mmol) of copper iodide, 13.83 g (143.96 mmol) of sodium tert-butoxide, 1.644 g (14.40 mmol) of trans-1,2-diaminocyclohexane, and 150 ml of dioxane were allowed to react at a temperature of 100° C. for 12 hours. After the reaction mixture was cooled to room temperature, ethanol was added thereto to produce precipitates that were subsequently separated by filtration. The separated precipitates were purified using column chromatography, thereby obtaining 26.4 g (yield: 75%) of Intermediate I-16-2.

3) Synthesis of Compound 16

5 g (23 mmol) of 3,6-dicyano-9H-carbazole, 13.4 g (27.62 mmol) of Intermediate I-16-2, 2.192 g (11.51 mmol) of copper iodide, 6.362 g (46 mmol) of potassium carbonate, 4.148 g (23 mmol) of 1,10-phenanthroline, and 120 ml of dimethylformamide were allowed to react for 24 hours. The crude products obtained therefrom were purified by column chromatography using dichloromethane:n-hexane, thereby obtaining 2.11 g (yield: 33%) of Compound 16. This compound was identified using LC-Mass.

LC-Mass (calculated: 622.73 g/mol. found: M+H=623 g/mol).

Comparative Synthesis Example 1: Synthesis of Compound A

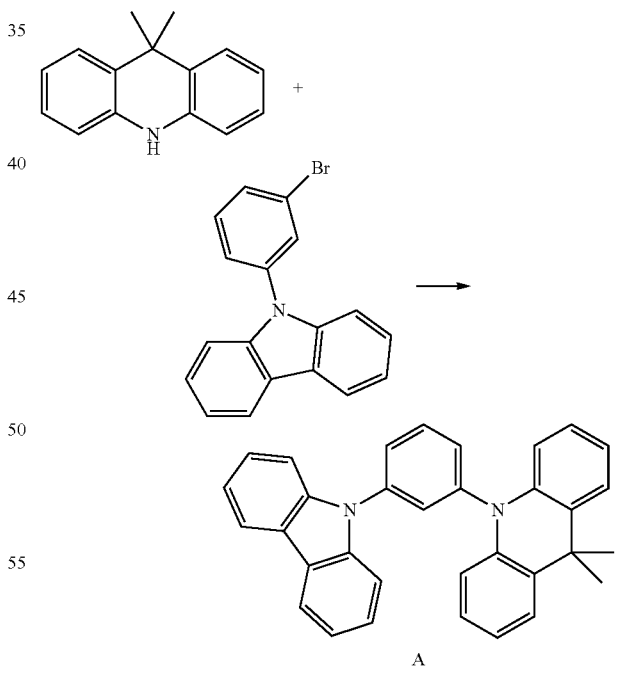

10 g (4718 mmol) of acridine, 18.4 g (57.34 mmol) of 9-(3-bromophenyl)-9H-carbazole, 8 g (71.67 mmol) of potassium tert-butoxide, 0.536 g (2.39 mmol) of palladium acetate, 0.774 ml (1.91 mmol) of tri-tert-butylphosphine (50 percent by weight (wt %) toluene), and 60 ml of toluene were allowed to react at a temperature of 110° C. for 24 hours. After the reaction was completed, the resulting product was filtered to produce crude products. The crude products obtained therefrom were recrystallized twice, each using toluene:methanol, thereby obtaining 14.6 g (68%) of Compound A. This compound was identified using LC-Mass.

LC-Mass (calculated: 450.59 g/mol. found: MA-H=451 g/mol).

Comparative Synthesis Example 2: Synthesis of Compound B

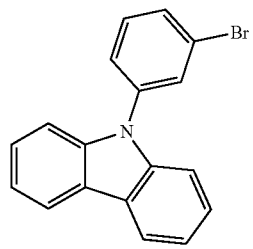

+

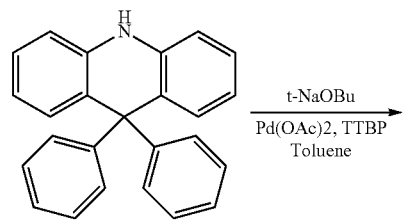

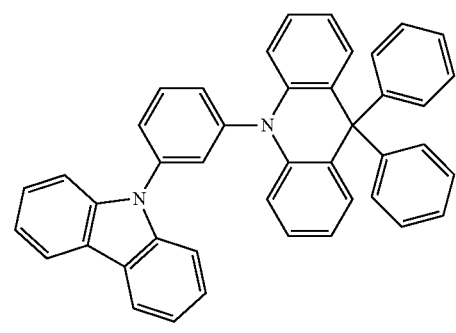

10 g (30 mmol) of 9,9-diphenyl-9,10-dihydroacridine, 11.6 g (36 mmol) of 9-(3-bromophenyl)-9H-carbazole, 4.324 g (45 mmol) of sodium tert-butoxide, 0.337 g (1.5 mmol) of palladium acetate, 0.6 ml (1.5 mmol) of tri-tert-butylphosphine, and 60 ml of toluene were allowed to react at a temperature of 110° C. for 24 hours. After the reaction was completed, the resulting product was filtered to produce crude products. The crude products obtained therefrom were recrystallized twice, each using dichloromethane:n-hexane, thereby obtaining 4.44 g (yield: 26%) of Compound B. This compound was identified using LC-Mass.

LC-Mass (calculated: 574.73 g/mol. found: M+H=575 g/mol).

Comparative Synthesis Example 3: Synthesis of Compound C

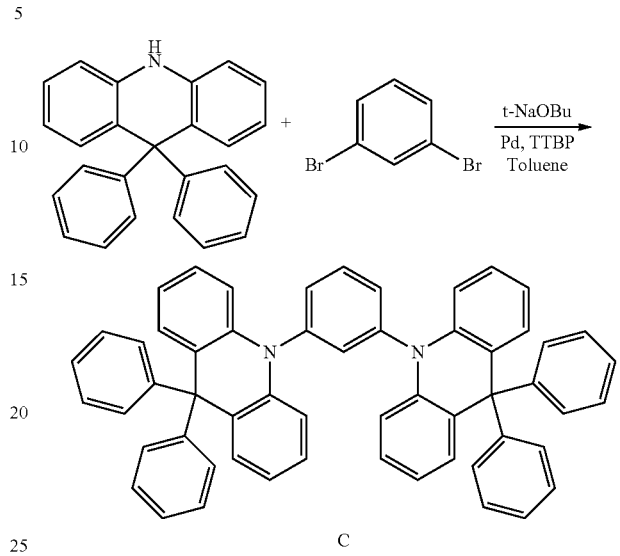

10 g (30 mmol) of 9,9-diphenyl-9,10-dihydroacridine, 15.4 g (66 mmol) of 1,3-dibromobenzene, 4.324 g (45 mmol) of sodium tert-butoxide, 0,337 g (1.5 mmol) of palladium acetate, 1.2 ml (3 mmol) of tri-tert-butylphosphine, and 60 ml of toluene were allowed to react at a temperature of 110° C. for 24 hours. After the reaction was completed, the resulting product was filtered to produce crude products. The crude products obtained therefrom were purified using column chromatography, thereby obtaining 11.5 g (yield: 52%) of Compound C. This compound was identified using LC-Mass.

LC-Mass (calculated: 740.95 g/mol. found: M+H=742 g/mol).

Comparative Synthesis Example 4: Synthesis of Compound D

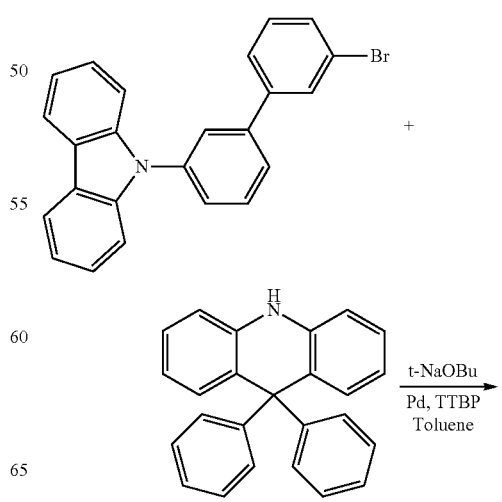

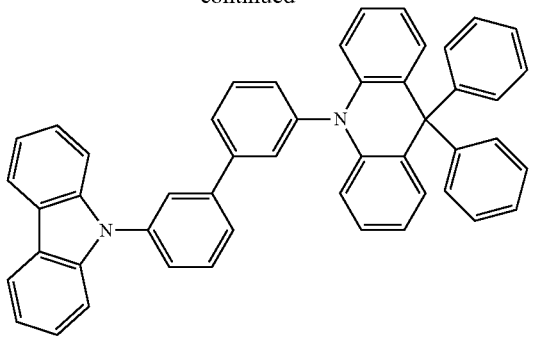

D 10 g (30 mmol) of 9,9-diphenyl-9,10-dihydroacridine, 14.3 g (36 mmol) of 9-(3'-bromo-[1,1'-biphenyl]-3-yl)-9H-carbazole, 4,324 g (45 mmol) of sodium tert-butoxide, 0.337 g (1.5 mmol) of palladium acetate, 0.6 ml (1.5 mmol) of tri-tert-butylphosphine, and 60 ml of toluene were allowed to react at a temperature of 110° C. for 24 hours. After the reaction was completed, the resulting product was filtered to produce crude products. The crude products obtained therefrom were purified using column chromatography, thereby obtaining 16 g (yield: 84%) of Compound D. This compound was identified using LC-Mass.

LC-Mass (calculated: 650.83 g/mol. found: MA-H=652 g/mol).

Evaluation Example 1: Evaluation of HOMO, LUMO, and Triplet (T1) Energy Levels

HOMO, LUMO, and T1 energy levels of Compounds 3 and A to D were evaluated as described in Table 1, and the results are shown in Table 2.

TABLE 1

| | |
|---|---|
| Evaluation of HOMO energy level | Voltage (V)-current (A) graphs for each compound were obtained according to a cyclic voltammetry (CV) (using 0.1 molar (M) $Bu_4NClO_4$ as an electrolyte, $CH_2Cl_2$ as a solvent for the electrode: 3-electrode system (using a glassy carbon (GC) working electrode, an Ag/AgCl reference electrode, and a Pt auxiliary electrode). The HOMO energy levels of each compound were calculated using a reduction onset in the graphs. |
| Evaluation of LUMO energy level | Each compound was diluted in $CHCl_3$ at a concentration of $1 \times 10^{-5}$M, and UV absorption spectra thereof were measured at room temperature using a Chimadzu UV-350 spectrometer. Then, LUMO energy levels of each compound were calculated using an optical band gap (Eg) based on the UV absorption edge. |
| Evaluation of T1 energy level | Toluene and mixtures of each compound (wherein 1 milligram (mg) of each compound was dissolved in 3 cubic centimeters (cc) of toluene) were contained in a quartz cell, placed in liquid nitrogen (77 Kelvins (K)), and subjected to measure photoluminescence spectra using a photoluminescence measuring device. Then, T1 energy levels were measured by analyzing only low-temperature peaks compared to typical photoluminescence spectra at room temperature |

TABLE 2

| | Compound No. | HOMO | LUMO | T1 |
|---|---|---|---|---|
| Example 1 | Compound 3 | −5.47 | −1.93 | 3.06 |
| Comparative Example 1 | Compound A | −5.39 | −1.80 | 3.02 |
| Comparative Example 2 | Compound B | −5.47 | −1.89 | 3.01 |
| Comparative Example 3 | Compound C | −5.42 | −1.91 | 3.07 |

TABLE 2-continued

| | Compound No. | HOMO | LUMO | T1 |
|---|---|---|---|---|
| Comparative Example 4 | Compound D | −5.46 | −1.91 | 3.04 |

Referring to Table 2, it was confirmed that Compound 3 had suitable electric characteristics as a material for forming an organic light-emitting device.

Evaluation Example 2: Evaluation of Thermal Stability Characteristics

Thermal stabilities of Compound 3 and Compounds A to C were measured according to Thermo Gravimetric Analysis (TGA) and Differential Scanning calorimetry (DSC). Glass transition temperature (Tg) and decomposition temperature (Td) of each compound were measured by heat analysis ($N_2$ atmosphere, temperature range: from room temperature to 800° C. (10° C./min)-TGA, from room temperature to 400° C.-DSC, Pan Type: Pt Pan in disposal Al Pan (TGA), disposal Al pan (DSC)), and the results are shown in Table 3. Referring to Table 3, it was confirmed that Compound 3 had excellent thermal stability.

TABLE 3

| | Tg (° C.) | Td (° C., 0.1%) |
|---|---|---|
| Compound 3 | 153 | 366 |
| Compound A | — | 282 |
| Compound B | 108 | 297 |
| Compound C | 133 | 301 |
| Compound D | 127 | 245 |

Example 1

To manufacture a first electrode (i.e., an anode), an indium tin oxide (ITO) glass substrate (having a thickness of 1,500 Angstroms (Å)) was ultrasonically washed with distilled water. Afterwards, the substrate was ultrasonically washed with a solvent, such as isopropyl alcohol, acetone, and methanol, and dried. After the substrate was placed in a plasma cleaner, the substrate was cleaned for 5 minutes using oxygen plasma, and transferred to a vacuum depositor.

Compound HT3 and Compound HT-D2 were co-deposited on the ITO glass substrate to form a hole injection layer having a thickness of 100 Å. Next, Compound HT3 was deposited on the hole injection layer to form a hole transport layer having a thickness of 1,300 Å, and mCP was deposited on the hole transport layer to form an electron blocking layer having a thickness of 150 Å, thereby forming a hole transport region.

Compound 3 as a host and FIr6 (10 wt %) as a dopant were co-deposited on the hole transport region to form an emission layer having a thickness of 300 Å.

BCP was vacuum-deposited on the emission layer to form a hole blocking layer having a thickness of 100 Å, and Compound ET3 and Liq were co-deposited on the hole blocking layer to form an electron transport layer having a thickness of 250 Å. Next, Liq was deposited on the electron transport layer to form an electron injection layer having a thickness of 5 Å, and Al was deposited on the electron injection layer to form a second electrode (i.e., a cathode) having a thickness of 1,000 Å, thereby manufacturing an organic light-emitting device.

Comparative Examples 1 to 4

Organic light-emitting devices were manufactured in the same manner as in Example 1, except that in forming the emission layer, Compounds as shown in Table 4 were used instead of Compound 3 (i.e., the host).

Evaluation Example 4: Evaluation of Characteristics of Organic Light-Emitting Devices The driving voltage, current efficiency and quantum yield of the organic light-emitting devices of Example 1 and Comparative Examples 1 to 4 were measured by using a current-voltage meter (Keithley 2400) and a luminance meter (Minolta Cs-1000A), and the results are summarized in Table 4. In Table 4, the driving voltage, current efficiency, and quantum yield of the organic light-emitting devices of Example 1 and Comparative Examples 2 to 4 were each represented as relative values based on those of the organic light-emitting device of Comparative Example 1. In addition, graphs showing a relationship between luminance and efficiency, a relationship between luminance and external quantum efficiency, and electroluminance spectra of the organic light-emitting devices of Example 1 and Comparative Examples 1 to 4 are shown in FIGS. 3, 4, and 5, respectively.

TABLE 4

| Host | | Driving voltage (relative value) | Current efficiency (relative value) | Quantum yield (relative value) | Emission color |
|---|---|---|---|---|---|
| Example 1 | Compound 3 | 85 | 424 | 390 | Blue |
| Comparative Example 1 | Compound A | 100 | 100 | 100 | Blue |
| Comparative Example 2 | Compound B | 112 | 79 | 81 | Blue |
| Comparative Example 3 | Compound C | 96 | 58 | 56 | Blue |
| Comparative Example 4 | Compound D | 114 | 134 | 100 | Blue |

Figure 2:
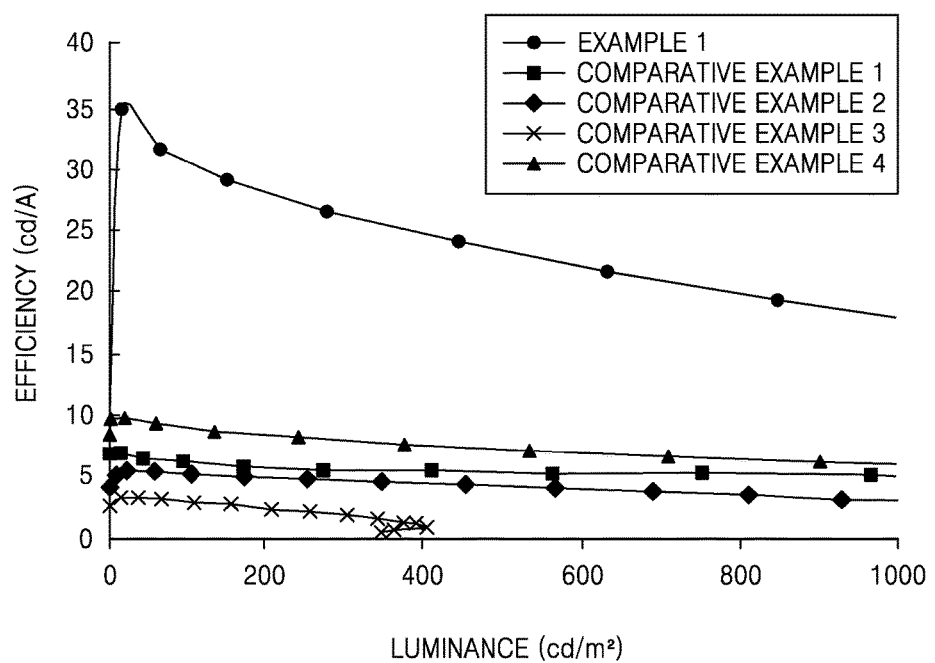
FIG. 2 is a graph of efficiency (candelas per ampere, cd/A) versus luminance (candelas per square meter, $cd/m^2$) showing a relationship between brightness and efficiency of organic light-emitting devices prepared according to Example 1 and Comparative Examples 1 to 4, respectively.
Figure 3:
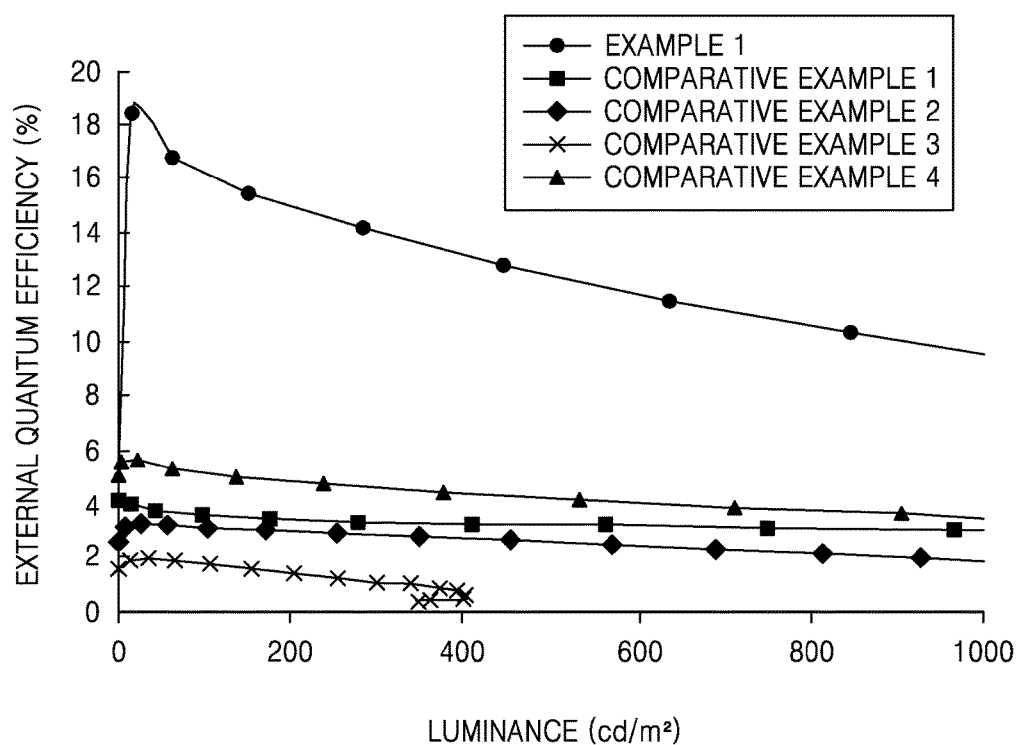
FIG. 3 is a graph of external quantum efficiency (%, percent) versus luminance (candelas per square meter, $cd/m^2$) showing a relationship between brightness and external quantum efficiency of organic light-emitting devices prepared according to Example 1 and Comparative Examples 1 to 4, respectively.
Figure 4:
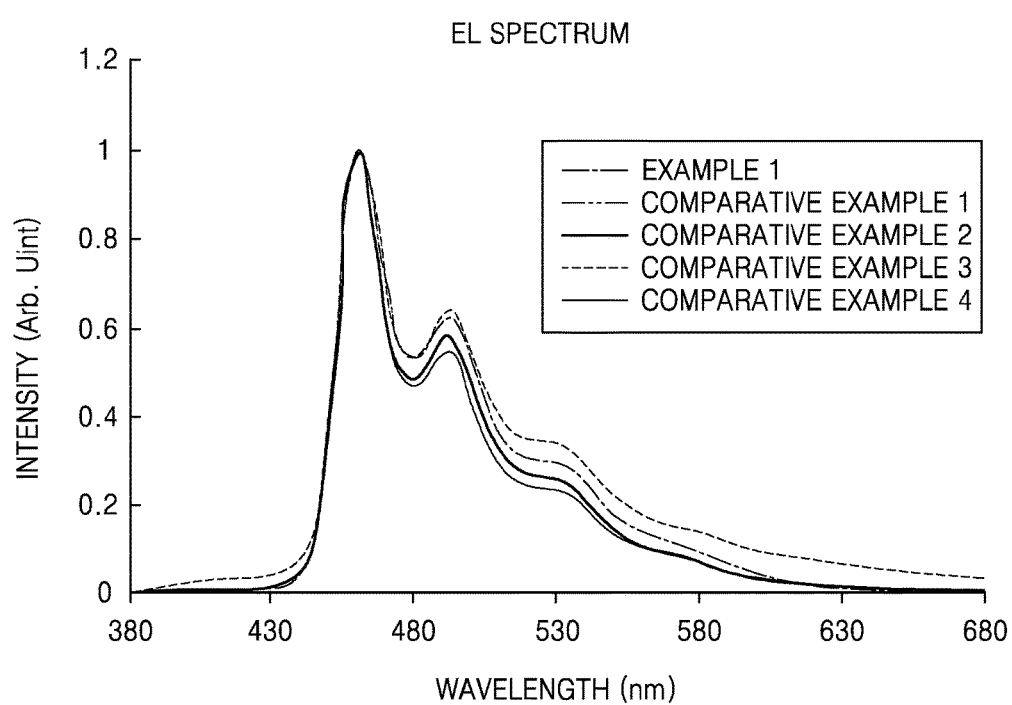
FIG. 4 is a graph of intensity (arbitrary units, arb, unit) versus wavelength (nanometers, nm) showing electroluminescence spectra of organic light-emitting devices prepared according to Example 1 and Comparative Examples 1 to 4, respectively.

Referring to Table 4 and FIGS. 2 to 4, it was confirmed that the organic light-emitting device of Example 1 had a lower driving voltage and a higher efficiency than those of the organic light-emitting devices of Comparative Examples 1 to 4.

According to one or more embodiments of the present inventive concept, a condensed cyclic compound has excellent electric characteristics and thermal stability, and thus an organic light-emitting device including the condensed cyclic compound may have a low driving voltage, high efficiency, high currency, high quantum yield, and long lifespan characteristics.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the present disclosure as defined by the following claims.

What is claimed is:

1. A condensed cyclic compound represented by Formula 1:

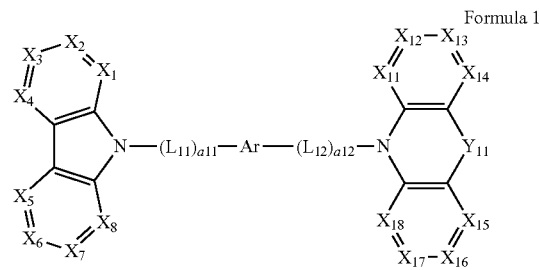

Formula 1 wherein, in Formula 1,
$X_1$ is N or $C(R_1)$, $X_2$ is N or $C(R_2)$, $X_3$ is N or $C(R_3)$, $X_4$ is N or $C(R_4)$, $X_5$ is N or $C(R_5)$, $X_6$ is N or $C(R_6)$, $X_7$ is N or $C(R_7)$, $X_8$ is N or $C(R_8)$, $X_{11}$ is N or $C(R_{11})$, $X_{12}$ is N or $C(R_{12})$, $X_{13}$ is N or $C(R_{13})$, $X_{14}$ is N or $C(R_{14})$, $X_{15}$ is N or $C(R_{15})$, $X_{16}$ is N or $C(R_{16})$, $X_{17}$ is N or $C(R_{17})$, and $X_{18}$ is N or $C(R_{18})$,
$Y_{11}$ is O, S, $C(R_{101})(R_{102})$, or $Si(R_{101})(R_{102})$,
$R_1$ to $R_8$ are independently selected from
a hydrogen, a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group,
a $C_1$-$C_{20}$ alkyl group and a $C_1$-$C_{20}$ alkoxy group, each substituted with at least one of a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, a pyrimidinyl group, a pyrazinyl group, a pyridazinyl group, and a triazinyl group;
a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group, and an imidazopyridinyl group;

a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group, and an imidazopyridinyl group, each substituted with at least one of a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, and —Si($Q_{31}$)($Q_{32}$)($Q_{33}$); and —Si($Q_1$)($Q_2$)($Q_3$), $R_{11}$ to $R_{18}$, $R_{101}$, and $R_{102}$ each are independently selected from:

a hydrogen, a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$), wherein the substituted or unsubstituted monovalent non-aromatic condensed heteropolycyclic group does not comprise a substituted or an unsubstituted carbazolyl group, and $R_{101}$ and $R_{102}$ are optionally linked to each other to form a saturated or unsaturated ring, Ar is a group represented by one of Formulae 2A to 2D:

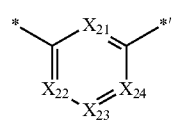

Formula 2A

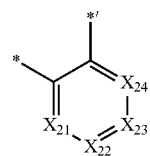

Formula 2B

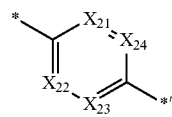

Formula 2C

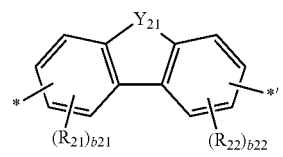

Formula 2D wherein, in Formulae 2A to 2D,

* and *' each independently indicate a binding site to a neighboring atom, $X_{21}$ is N or C($R_{21}$), $X_{22}$ is N or C($R_{22}$), $X_{23}$ is N or C($R_{23}$), and $X_{24}$ is N or C($R_{24}$), $Y_{21}$ is O, S, P(=O)$_2$, Se, C($R_{25}$)($R_{26}$), or Si($R_{25}$)($R_{26}$), $R_{21}$ to $R_{26}$ each are independently selected from a hydrogen, a deuterium, a $C_1$-$C_4$ alkyl group, a $C_6$-$C_{20}$ aryl group, a $C_1$-$C_{20}$ heteroaryl group, and —Si($Q_{11}$)($Q_{12}$)($Q_{13}$), b21 and b22 each are independently selected from integers of 1 to 3, provided that when b21 is 2 or more, groups $R_{21}$ are identical to or different from each other, and provided that when b22 is 2 or more, groups $R_{22}$ are identical to or different from each other, $L_{11}$ and $L_{12}$ each are independently selected from:
a phenylene group, a pyridinylene group, a pyrimidinylene group, a pyrazinylene group, a pyridazinylene group, a triazinylene group, a dibenzofuranylene group, a dibenzothiophenylene group, and a dibenzosilolylene group; and
a phenylene group, a pyridinylene group, a pyrimidinylene group, a pyrazinylene group, a pyridazinylene group, a triazinylene group, a dibenzofuranylene group, a dibenzothiophenylene group, and a dibenzosilolylene group, each substituted with at least one of a deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —Si($Q_{21}$)($Q_{22}$)($Q_{23}$), a11 and a12 each are independently selected from 0, 1, 2, 3, 4, and 5, provided that when a11 is 2 or more, groups $L_{11}$ are identical to or different from each other, and provided that when a12 is 2 or more, groups $L_{12}$ are identical to or different from each other, and $Q_1$ to $Q_3$, $Q_{11}$ to $Q_{13}$, $Q_{21}$ to $Q_{23}$, and $Q_{31}$ to $Q_{33}$ each are independently selected from a hydrogen, a $C_1$-$C_{60}$ alkyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic condensed heteropolycyclic group, provided that the monovalent non-aromatic condensed heteropolycyclic group does not comprise a carbazolyl group,
wherein the condensed cyclic compound represented by Formula 1 comprises at least one cyano (—CN) group.

2. The condensed cyclic compound of claim 1, wherein at least one of a group represented by

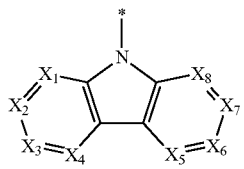

and a group represented by

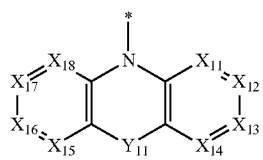

comprises at least one cyano (—CN) group.

3. The condensed cyclic compound of claim 1, wherein
$X_1$ is N, $X_2$ is C($R_2$), $X_3$ is C($R_3$), $X_4$ is C($R_4$), $X_5$ is C($R_5$), $X_6$ is C($R_6$), $X_7$ is C($R_7$), $X_8$ is C($R_8$), $X_{11}$ is C($R_{11}$), $X_{12}$ is C($R_{12}$), $X_{13}$ is C($R_{13}$), $X_{14}$ is C($R_{14}$), $X_{15}$ is C($R_{15}$), $X_{16}$ is C($R_{16}$), $X_{17}$ is C($R_{17}$), and $X_{18}$ is C($R_{18}$),
$X_1$ is C($R_1$), $X_2$ is N, $X_3$ is C($R_3$), $X_4$ is C($R_4$), $X_5$ is C($R_5$), $X_6$ is C($R_6$), $X_7$ is C($R_7$), $X_8$ is C($R_8$), $X_{11}$ is C($R_{11}$), $X_{12}$ is C($R_{12}$), $X_{13}$ is C($R_{13}$), $X_{14}$ is C($R_{14}$), $X_{15}$ is C($R_{15}$), $X_{16}$ is C($R_{16}$), $X_{17}$ is C($R_{17}$), and $X_{18}$ is C($R_{18}$),
$X_1$ is C($R_1$), $X_2$ is C($R_2$), $X_3$ is N, $X_4$ is C($R_4$), $X_5$ is C($R_5$), $X_6$ is C($R_6$), $X_7$ is C($R_7$), $X_8$ is C($R_8$), $X_{11}$ is C($R_{11}$), $X_{12}$ is C($R_{12}$), $X_{13}$ is C($R_{13}$), $X_{14}$ is C($R_{14}$), $X_{15}$ is C($R_{15}$), $X_{16}$ is C($R_{16}$), $X_{17}$ is C($R_{17}$), and $X_{18}$ is C($R_{18}$),
$X_1$ is C($R_1$), $X_2$ is C($R_2$), $X_3$ is C($R_3$), $X_4$ is N, $X_5$ is C($R_5$), $X_6$ is C($R_6$), $X_7$ is C($R_7$), $X_8$ is C($R_8$), $X_{11}$ is C($R_{11}$), $X_{12}$ is C($R_{12}$), $X_{13}$ is C($R_{13}$), $X_{14}$ is C($R_{14}$), $X_{15}$ is C($R_{15}$), $X_{16}$ is C($R_{16}$), $X_{17}$ is C($R_{17}$), and $X_{18}$ is C($R_{18}$),
$X_1$ is C($R_1$), $X_2$ is C($R_2$), $X_3$ is C($R_3$), $X_4$ is C($R_4$), $X_5$ is N, $X_6$ is C($R_6$), $X_7$ is C($R_7$), $X_8$ is C($R_8$), $X_{11}$ is C($R_{11}$), $X_{12}$ is C($R_{12}$), $X_{13}$ is C($R_{13}$), $X_{14}$ is C($R_{14}$), $X_{15}$ is C($R_{15}$), $X_{16}$ is C($R_{16}$), $X_{17}$ is C($R_{17}$), and $X_{18}$ is C($R_{18}$),
$X_1$ is C($R_1$), $X_2$ is C($R_2$), $X_3$ is C($R_3$), $X_4$ is C($R_4$), $X_5$ is C($R_5$), $X_6$ is N, $X_7$ is C($R_7$), $X_8$ is C($R_8$), $X_{11}$ is C($R_{11}$), $X_{12}$ is C($R_{12}$), $X_{13}$ is C($R_{13}$), $X_{14}$ is C($R_{14}$), $X_{15}$ is C($R_{15}$), $X_{16}$ is C($R_{16}$), $X_{17}$ is C($R_{17}$), and $X_{18}$ is C($R_{18}$),
$X_1$ is C($R_1$), $X_2$ is C($R_2$), $X_3$ is C($R_3$), $X_4$ is C($R_4$), $X_5$ is C($R_5$), $X_6$ is C($R_6$), $X_7$ is N, $X_8$ is C($R_8$), $X_{11}$ is C($R_{11}$), $X_{12}$ is C($R_{12}$), $X_{13}$ is C($R_{13}$), $X_{14}$ is C($R_{14}$), $X_{15}$ is C($R_{15}$), $X_{16}$ is C($R_{16}$), $X_{17}$ is C($R_{17}$), and $X_{18}$ is C($R_{18}$),
$X_1$ is C($R_1$), $X_2$ is C($R_2$), $X_3$ is C($R_3$), $X_4$ is C($R_4$), $X_5$ is C($R_5$), $X_6$ is C($R_6$), $X_7$ is C($R_7$), $X_8$ is N, $X_{11}$ is C($R_{11}$), $X_{12}$ is C($R_{12}$), $X_{13}$ is C($R_{13}$), $X_{14}$ is C($R_{14}$), $X_{15}$ is C($R_{15}$), $X_{16}$ is C($R_{16}$), $X_{17}$ is C($R_{17}$), and $X_{18}$ is C($R_{18}$), or
$X_1$ is C($R_1$), $X_2$ is C($R_2$), $X_3$ is C($R_3$), $X_4$ is C($R_4$), $X_5$ is C($R_5$), $X_6$ is C($R_6$), $X_7$ is C($R_7$), $X_8$ is C($R_8$), $X_{11}$ is C($R_{11}$), $X_{12}$ is C($R_{12}$), $X_{13}$ is C($R_{13}$), $X_{14}$ is C($R_{14}$), $X_{15}$ is C($R_{15}$), $X_{16}$ is C($R_{16}$), $X_{17}$ is C($R_{17}$), and $X_{18}$ is C($R_{18}$).

4. The condensed cyclic compound of claim 1, wherein $R_{11}$ to $R_{18}$, $R_{101}$, and $R_{102}$ each are independently selected from:
a hydrogen, a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;
a $C_1$-$C_{20}$ alkyl group and a $C_1$-$C_{20}$ alkoxy group, each substituted with at least one of a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, a pyrimidinyl group, a pyrazinyl group, a pyridazinyl group, and a triazinyl group;
a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group, and an imidazopyridinyl group;

a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group, and an imidazopyridinyl group, each substituted with at least one of a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, and —Si($Q_{31}$)($Q_{32}$)($Q_{33}$); and —Si($Q_1$)($Q_2$)($Q_3$), $R_{101}$ and $R_{102}$ are optionally linked to each other to form a saturated or unsaturated ring, and $Q_1$ to $Q_3$ and $Q_{31}$ to $Q_{33}$ each are independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cinnolinyl group, and a quinazolinyl group.

5. The condensed cyclic compound of claim 1, wherein $R_1$ to $R_8$, $R_{11}$ to $R_{18}$, $R_{101}$, and $R_{102}$ each are independently selected from:

a hydrogen, a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a methyl group, an ethyl group, an n-propyl group, an iso-propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a phenyl group, a naphthyl group, a pyridinyl group, a pyrimidinyl group, and a triazinyl group;

a methyl group, an ethyl group, an n-propyl group, an iso-propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a phenyl group, a naphthyl group, a pyridinyl group, a pyrimidinyl group, and a triazinyl group, each substituted with at least one of a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, and a phosphoric acid group or a salt thereof; and —Si($Q_1$)($Q_2$)($Q_3$), $R_{101}$ and $R_{102}$ are optionally linked to each other to form a saturated or unsaturated ring, and $Q_1$ to $Q_3$ each are independently selected from a hydrogen, a $C_1$-$C_{10}$ alkyl group, a $C_1$-$C_{10}$ alkoxy group, and a phenyl group.

6. The condensed cyclic compound of claim 1, wherein $R_1$ to $R_8$ and $R_{11}$ to $R_{18}$ each are independently selected from a hydrogen, a deuterium, a cyano (—CN) group, a methyl group, an ethyl group, an n-propyl group, an iso-propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, and —Si(Q$_1$)(Q$_2$)(Q$_3$), and Q$_1$ to Q$_3$ each are independently selected from a hydrogen, a C$_1$-C$_{10}$ alkyl group, a C$_1$-C$_{10}$ alkoxy group, and a phenyl group.

7. The condensed cyclic compound of claim 1, wherein R$_{101}$ and R$_{102}$ each are independently selected from:

a methyl group, an ethyl group, an n-propyl group, an iso-propyl group, an n-butyl group, an isobutyl group, a sec-butyl group, a tert-butyl group, a phenyl group, and a naphthyl group; and a methyl group, an ethyl group, an n-propyl group, an iso-propyl group, an n-butyl group, an isobutyl group, a sec-butyl group, a tert-butyl group, a phenyl group, and a naphthyl group, each substituted with a cyano (—CN) group.

8. The condensed cyclic compound of claim 1, wherein Ar is a group represented by one of Formulae 2-1 to 2-28:

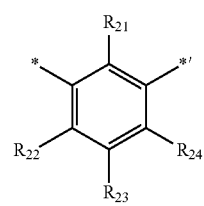
2-1

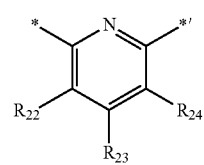
2-2

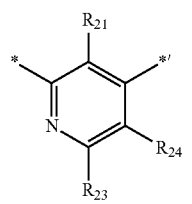
2-3

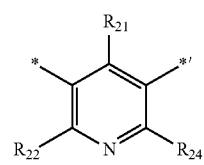
2-4

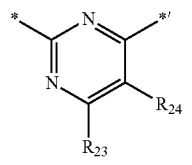
2-5

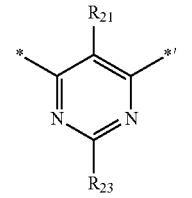
2-6

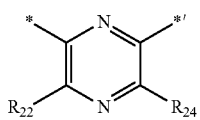
2-7

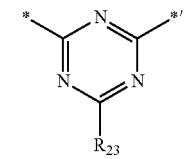
2-8

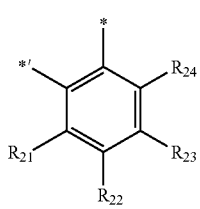
2-9

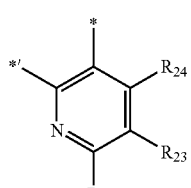
2-10

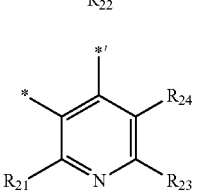
2-11

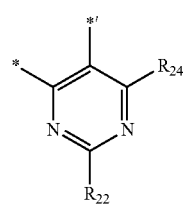
2-12

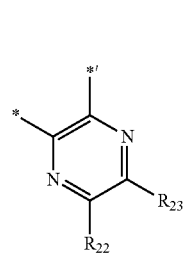
2-13

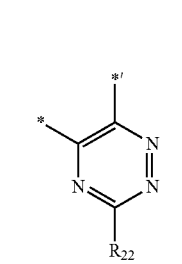
2-14

121

-continued 2-15
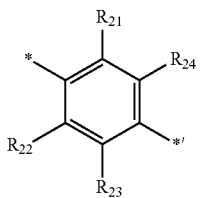

2-16
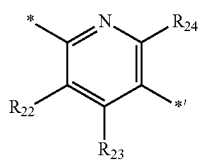

2-17
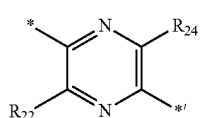

2-18
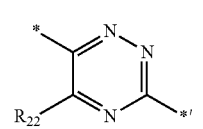

2-19
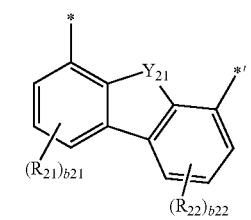

2-20
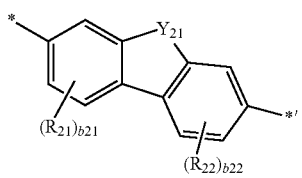

2-21
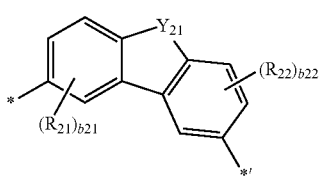

2-22
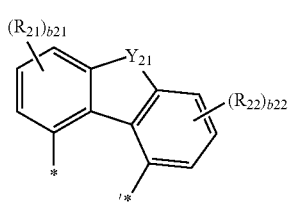

2-23
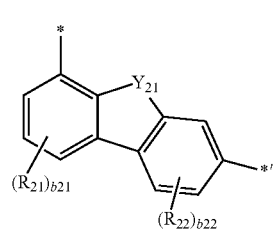

122

-continued 2-24
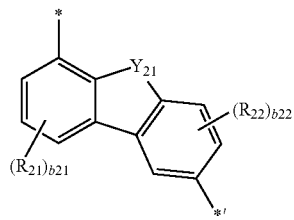

2-25
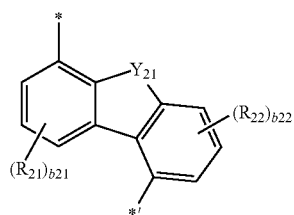

2-26
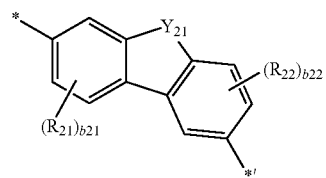

2-27
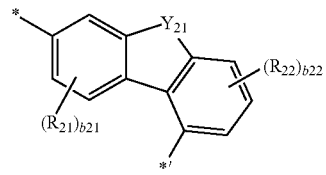

2-28
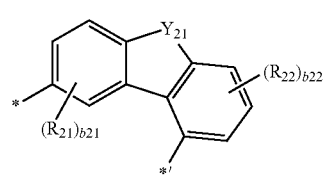

wherein, in Formulae 2-1 to 2-28, $Y_{21}$ is O or S, $R_{21}$ to $R_{24}$ each are independently selected from a hydrogen, a deuterium, a methyl group, an ethyl group, an n-propyl group, an iso-propyl group, an n-butyl group, an isobutyl group, a sec-butyl group, a tert-butyl group, a phenyl group, a pyridinyl group, a pyrimidinyl group, a pyrazinyl group, a pyridazinyl group, a triazinyl group, and $-Si(Q_{11})(Q_{12})(Q_{13})$, $Q_{11}$ to $Q_{13}$ each are independently selected from a hydrogen, a $C_1$-$C_{10}$ alkyl group, a $C_1$-$C_{10}$ alkoxy group, and a phenyl group, b21 and b22 each are independently selected from 1, 2, and 3, and

* and *' each indicate a binding site to a neighboring atom.

9. The condensed cyclic compound of claim 1, wherein *-$(L_{11})_{a11}$-Ar-$(L_{12})_{a12}$-* is a group represented by one of Formulae 4-1 to 4-19:

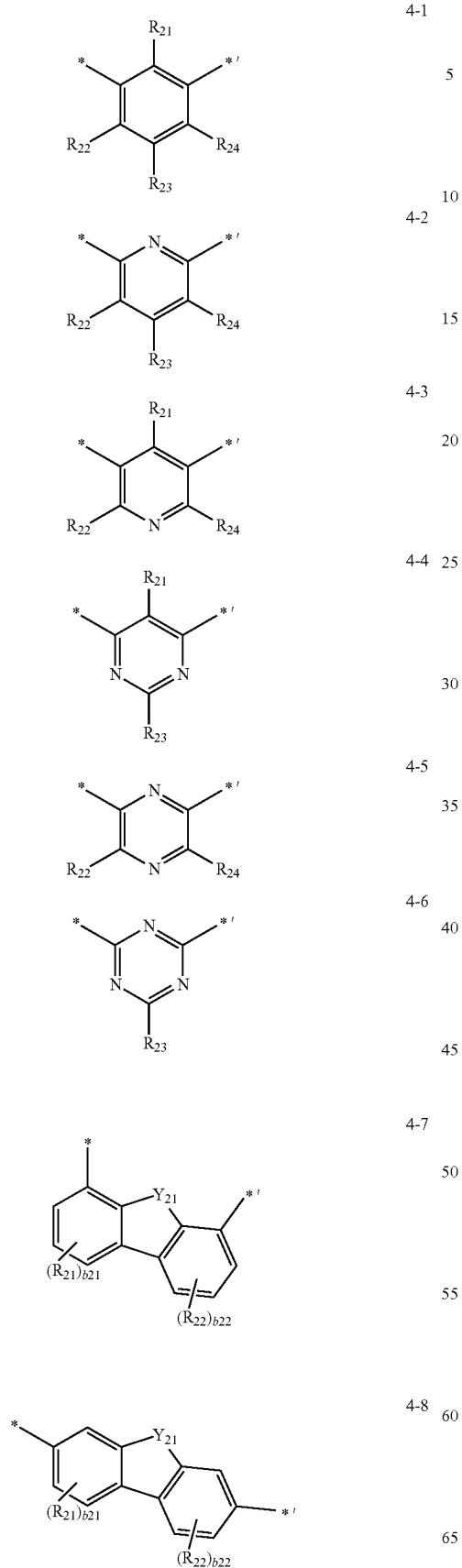
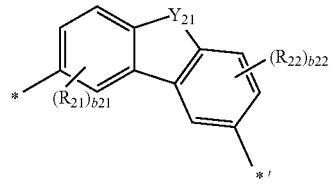
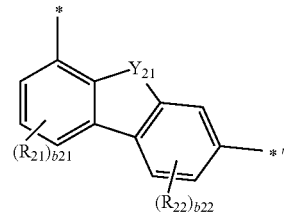
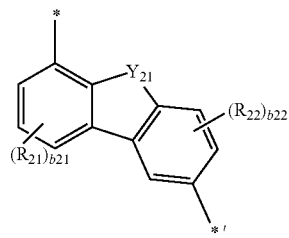
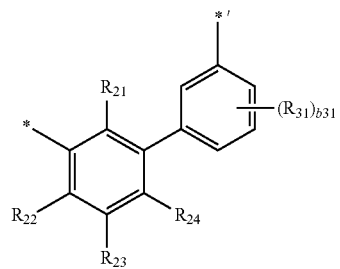
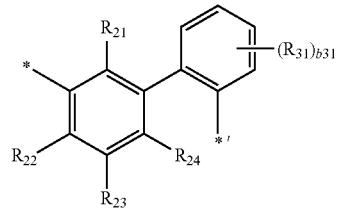
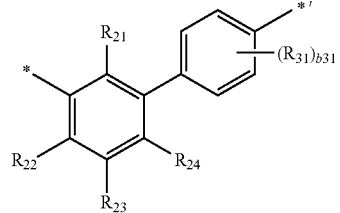

-continued

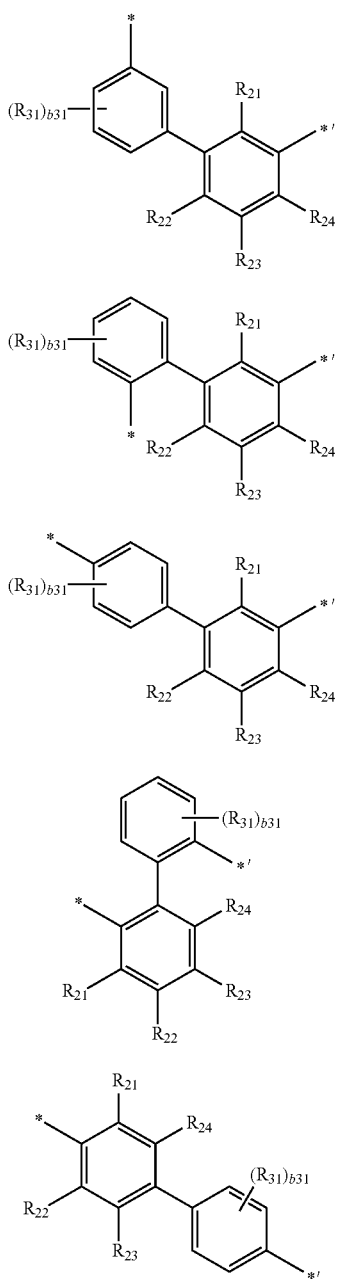

wherein, in Formulae 4-1 to 4-19,

Y$_{21}$ is O or S,

R$_{21}$ to R$_{24}$ and R$_{31}$ each are independently selected from a hydrogen, a deuterium, a methyl group, an ethyl group, an n-propyl group, an iso-propyl group, an n-butyl group, an isobutyl group, a sec-butyl group, a tert-butyl group, a phenyl group, a pyridinyl group, a pyrimidinyl group, a pyrazinyl group, a pyridazinyl group, a triazinyl group, and —Si(Q$_{21}$)(Q$_{22}$)(Q$_{23}$), Q$_{21}$ to Q$_{23}$ each are independently selected from a hydrogen, a C$_1$-C$_{10}$ alkyl group, a C$_1$-C$_{10}$ alkoxy group, and a phenyl group, b21 and b22 each are independently selected from 1, 2, and 3, b31 is selected from 1, 2, 3, and 4, and

* and *' each indicate a binding site to a neighboring atom.

10. The condensed cyclic compound of claim 1, wherein the condensed cyclic compound is represented by one of Formulae 1-1 to 1-15:

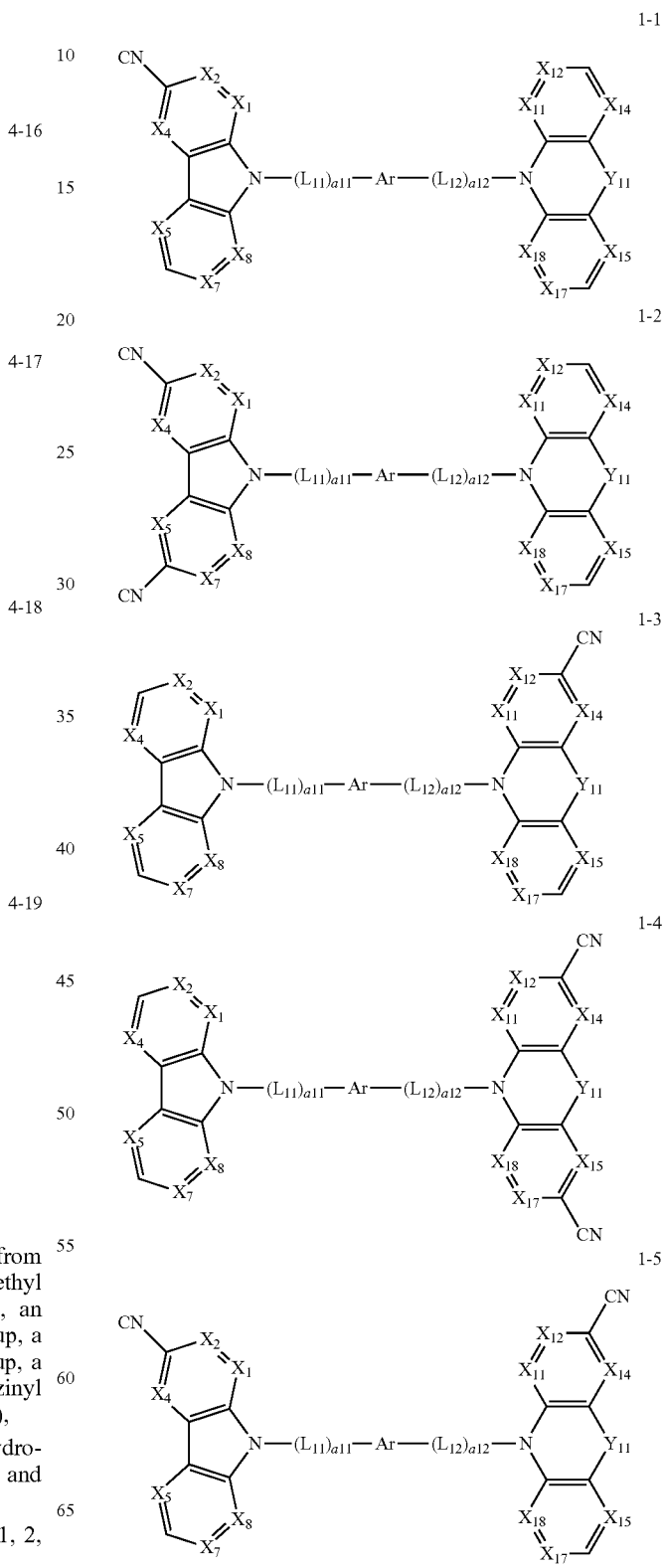

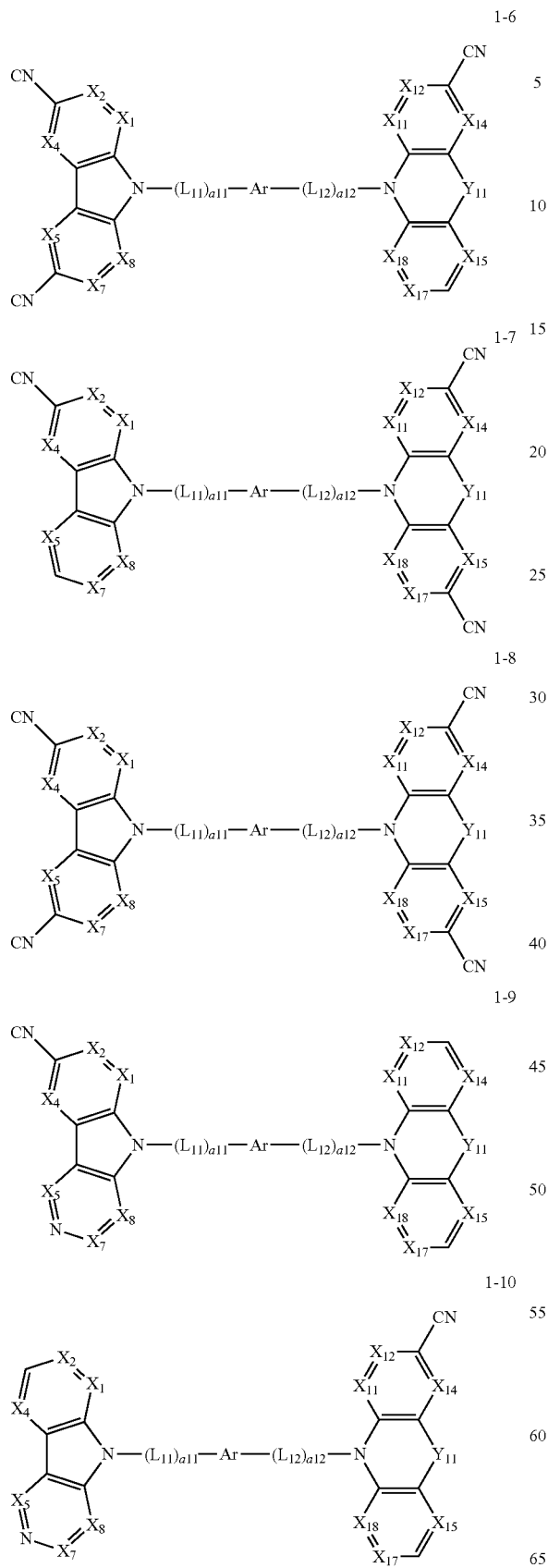
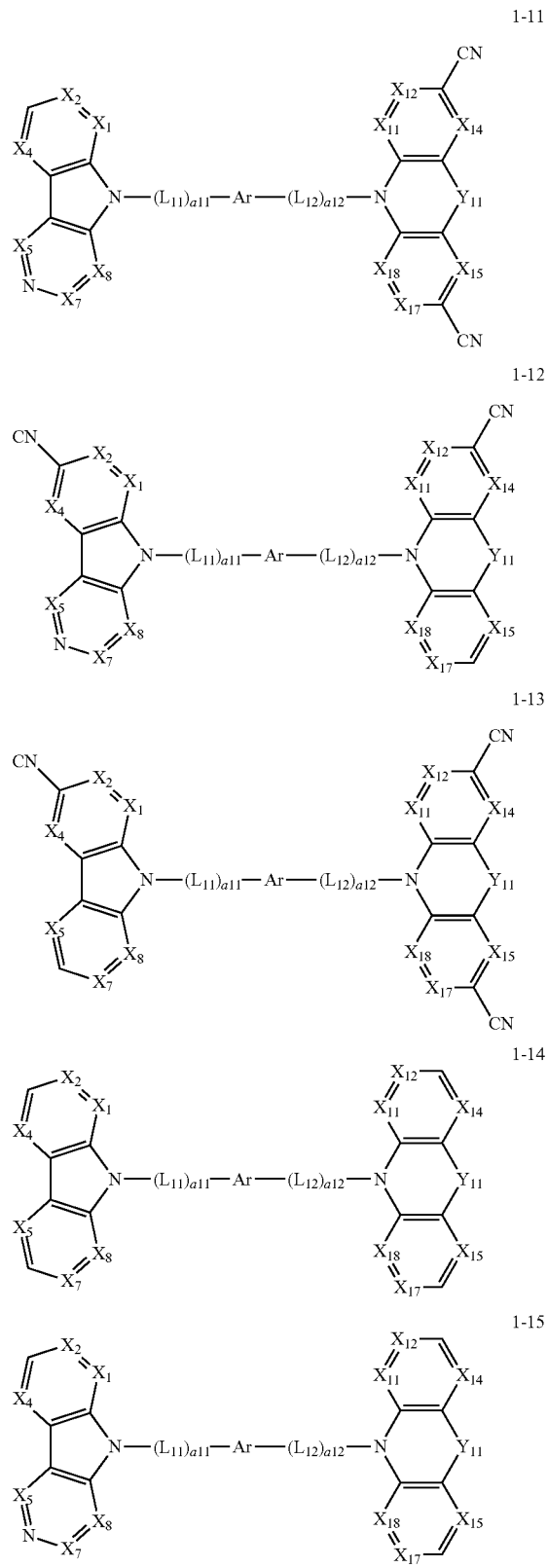
wherein, in Formulae 1-1 to 1-15,
$X_1$, $X_2$, $X_4$, $X_5$, $X_7$, $X_8$, $X_{11}$, $X_{12}$, $X_{14}$, $X_{15}$, $X_{17}$, $X_{17}$, $Y_{11}$, Ar, $L_{11}$, $L_{12}$, a11, and a12 are as defined in Formula 1.

11. The condensed cyclic compound of claim 1, wherein the condensed cyclic compound is selected from Compounds 1 to 103:
1
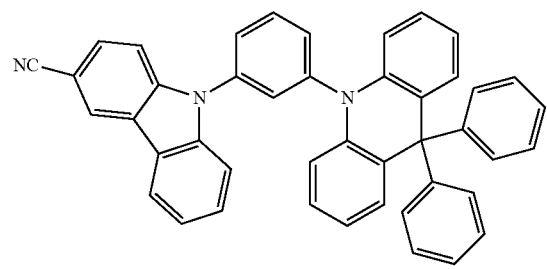
2
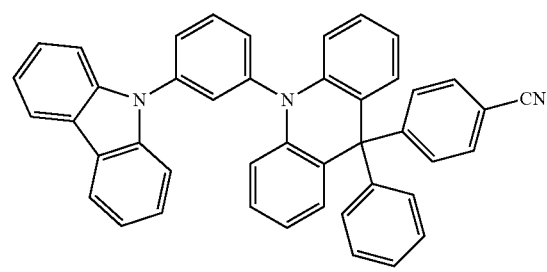
3
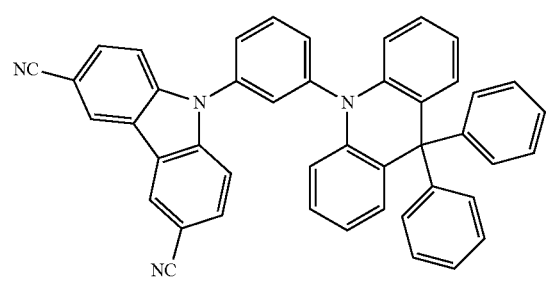
4
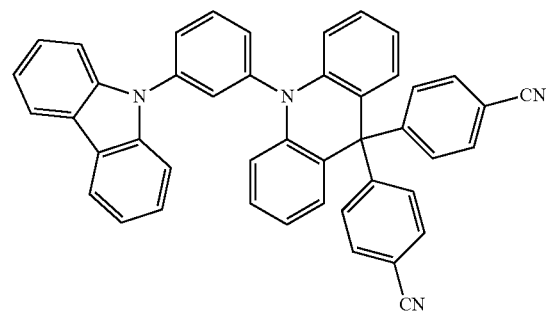
5
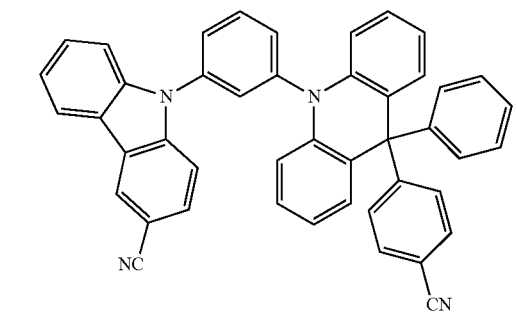
-continued
6
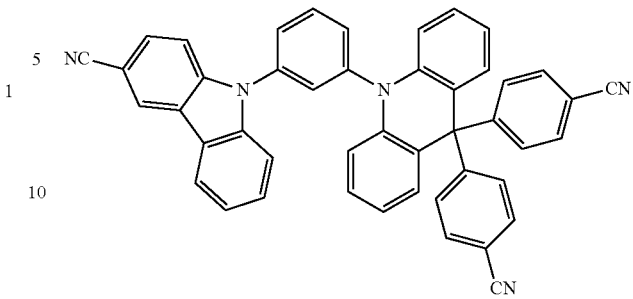
7
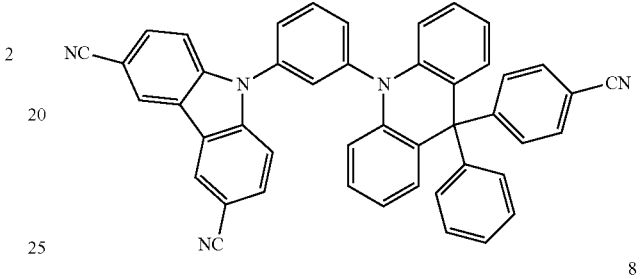
8
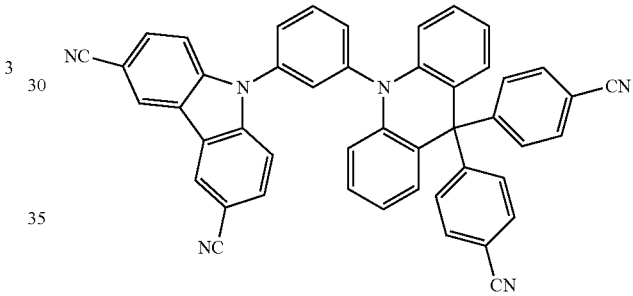
9
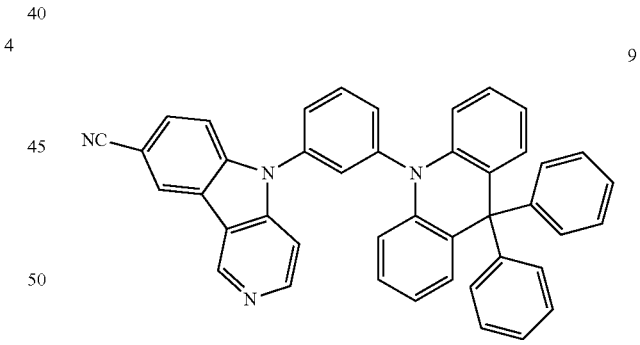
10
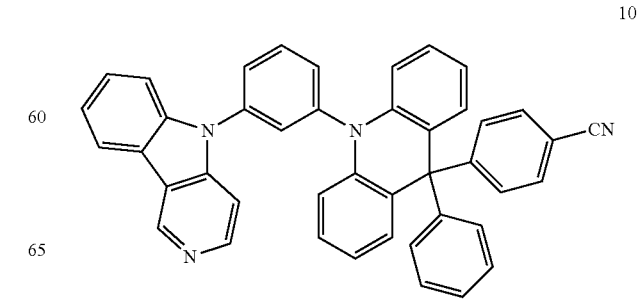

11
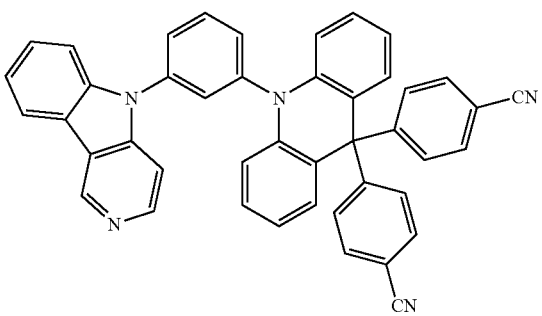
12
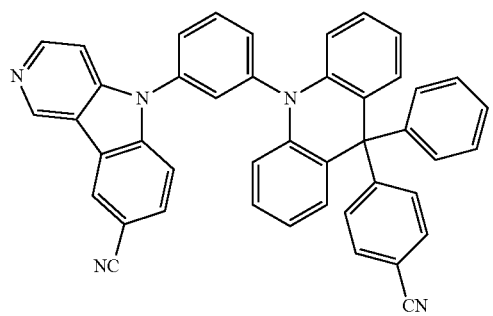
13
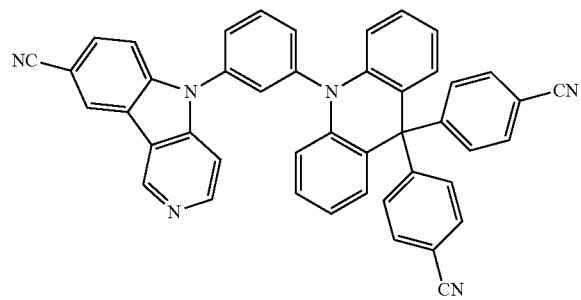
14
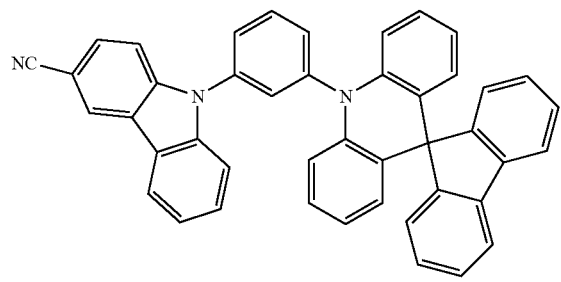
15
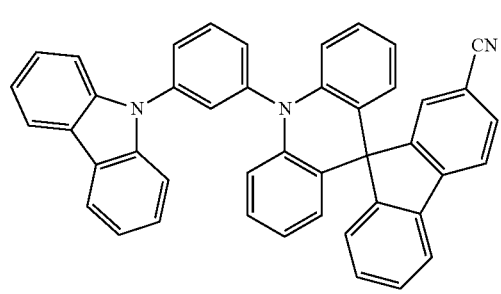
16
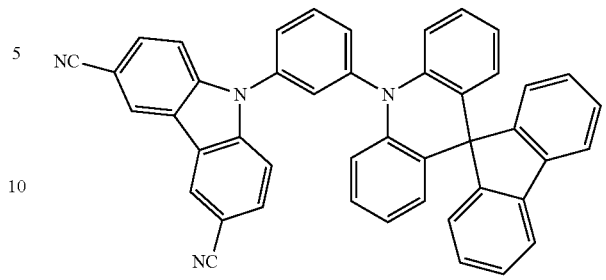
17
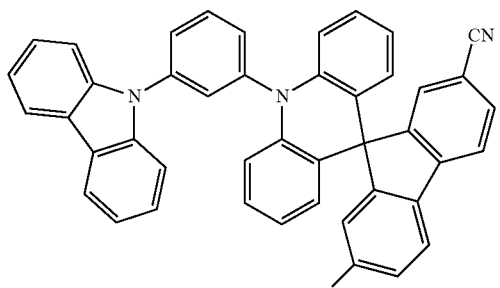
18
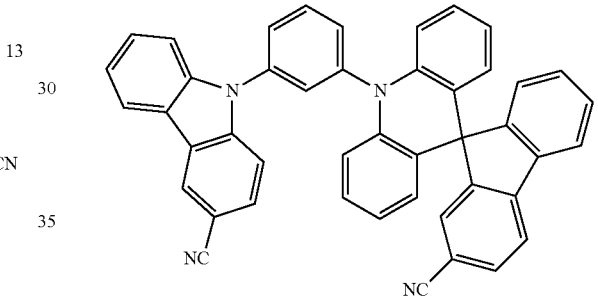
19
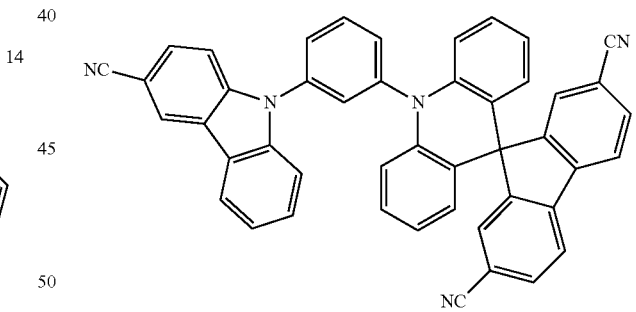
20
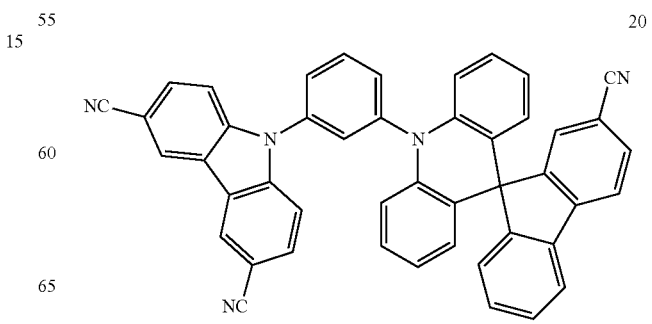

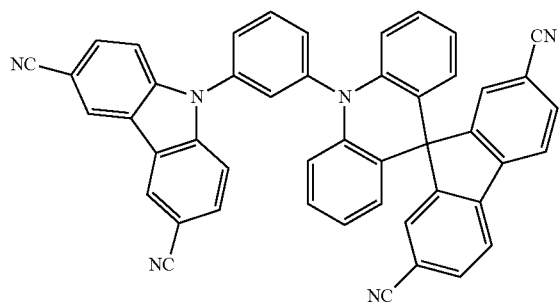
21
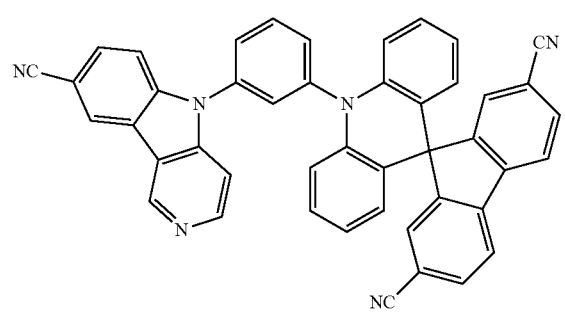
26
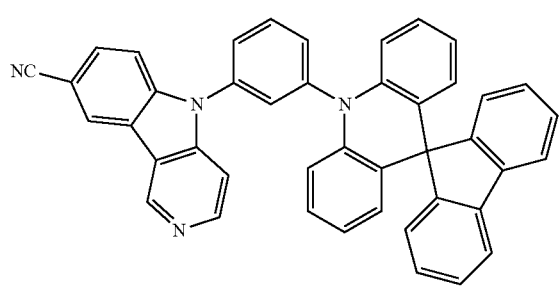
22
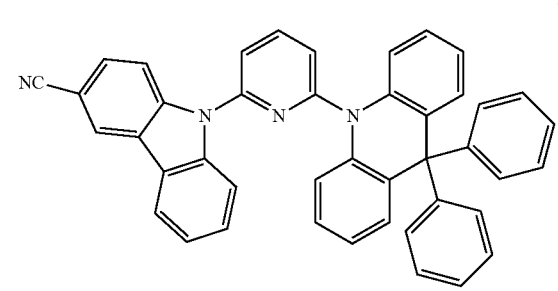
27
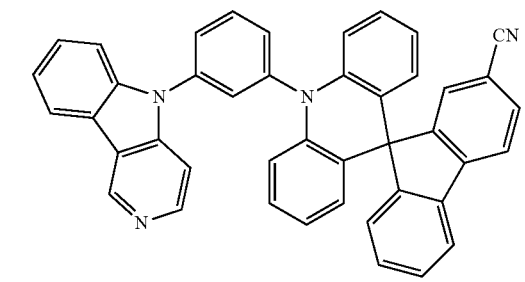
23
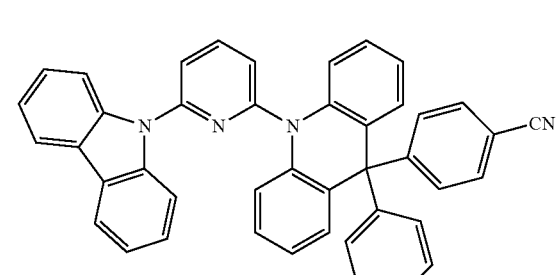
28
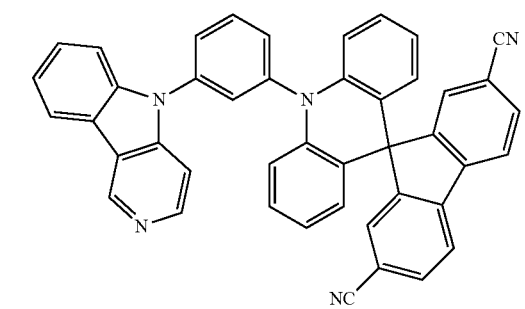
24
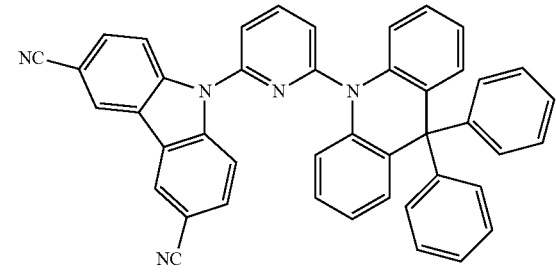
29
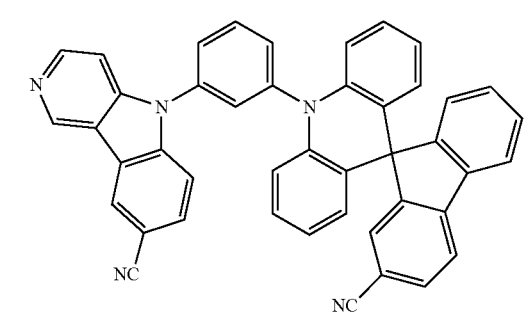
25
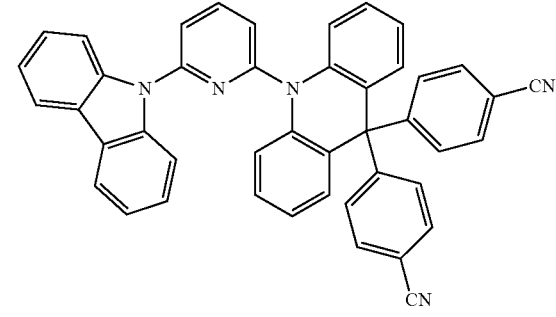
30

31
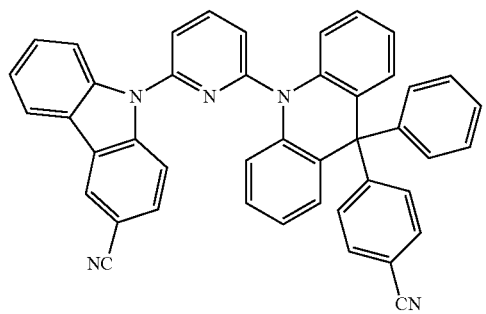
32
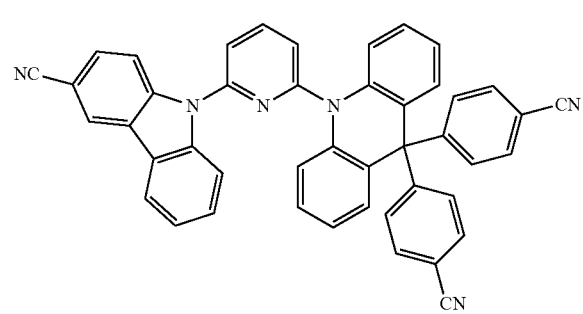
33
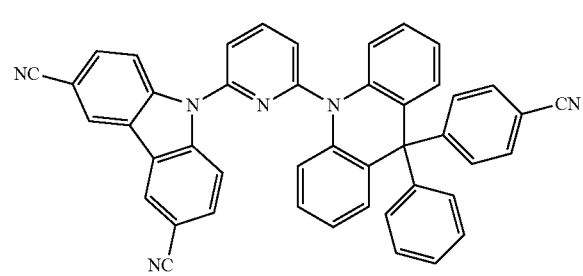
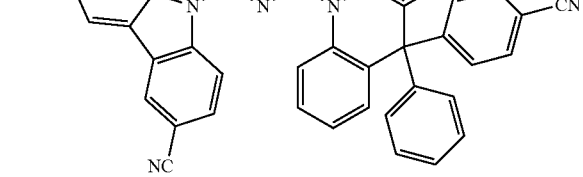
34
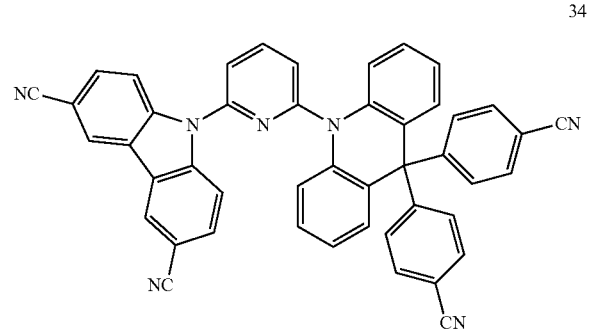
35
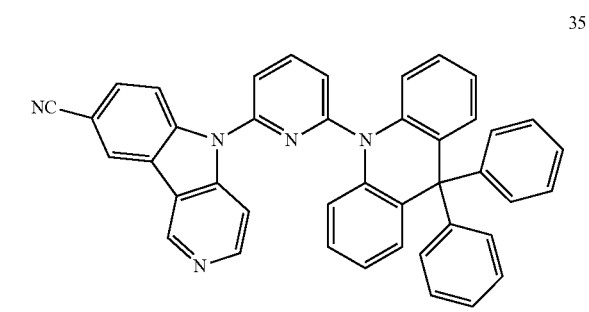
36
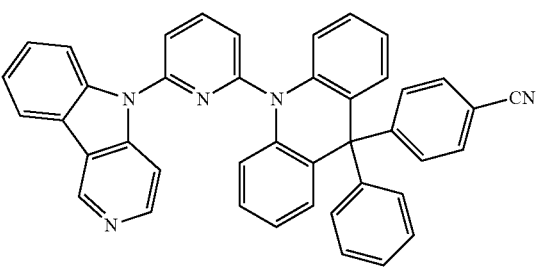
37
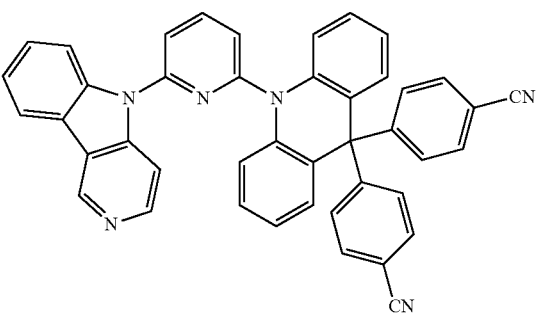
38
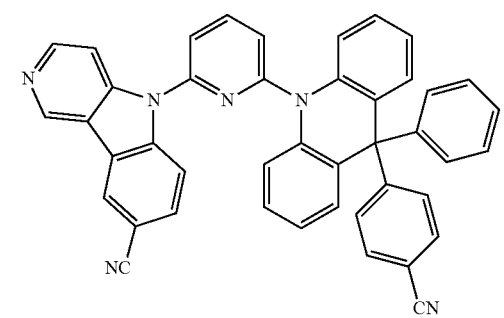
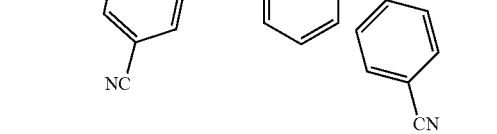
39
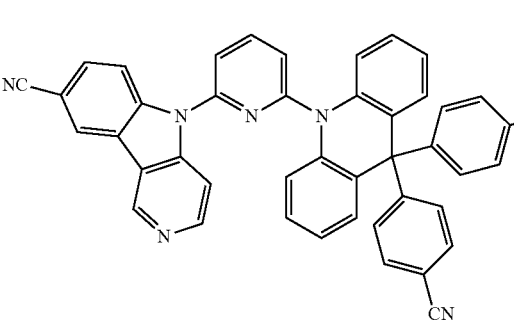
40
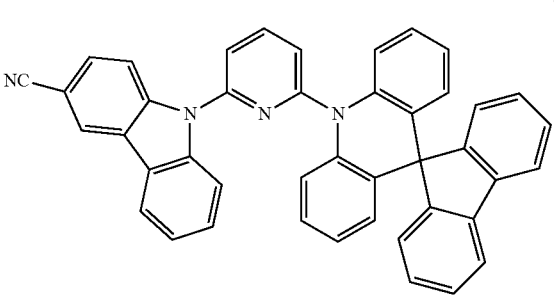

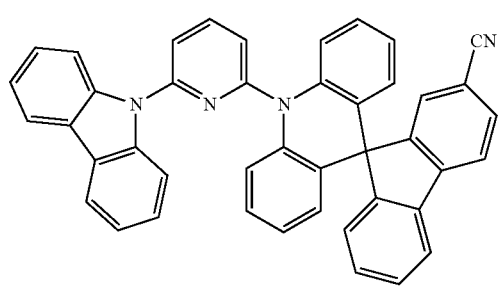
41
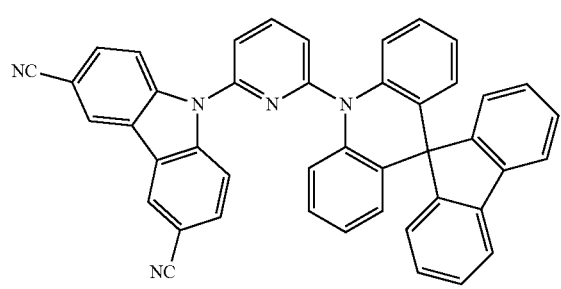
42
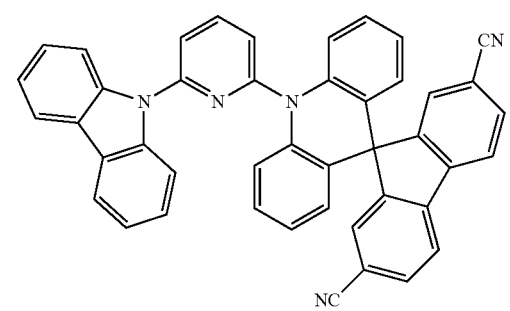
43
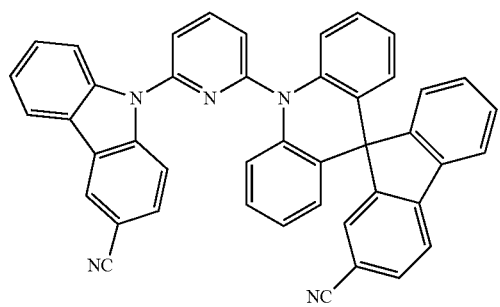
44
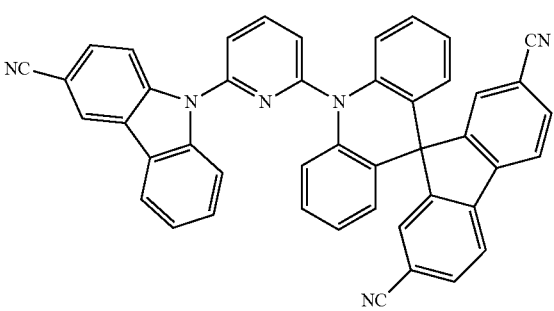
45
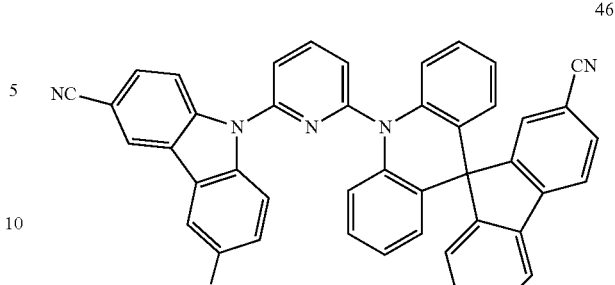
46
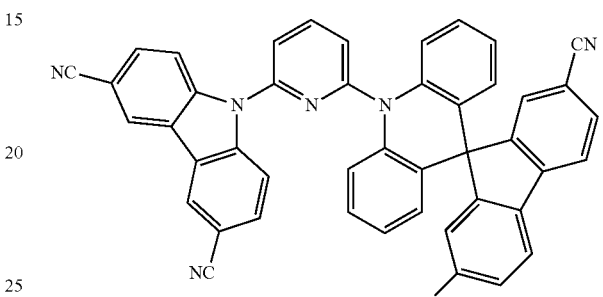
47
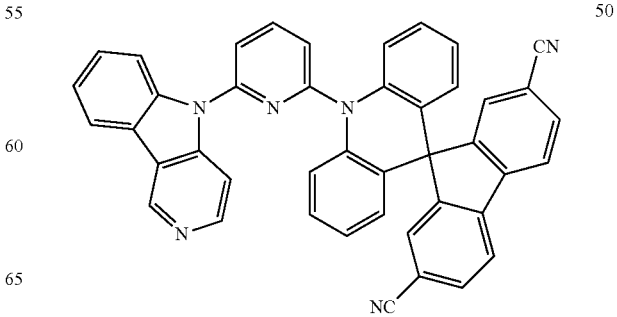
48
49
50

51
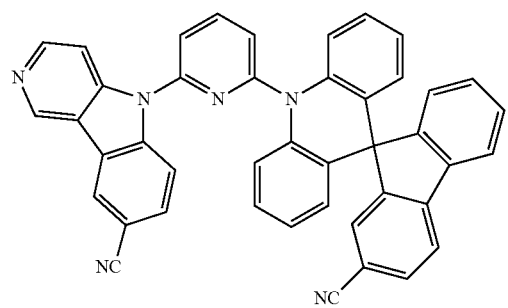
52
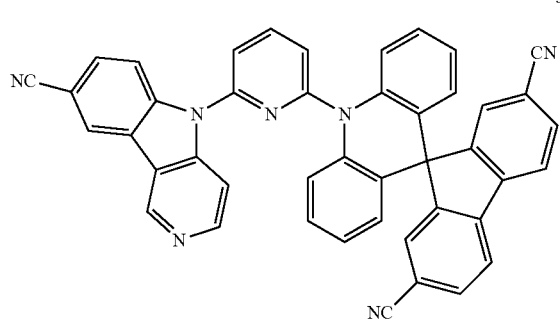
53
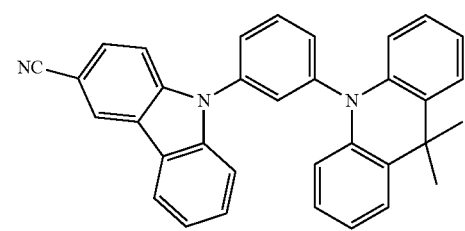
54
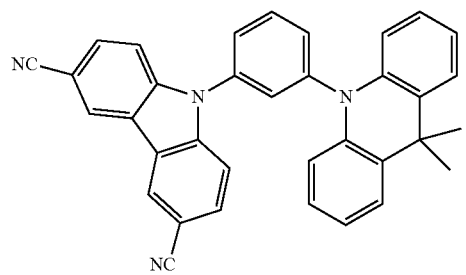
55
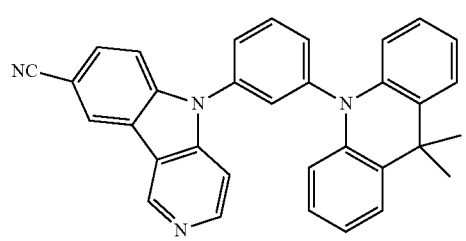
56
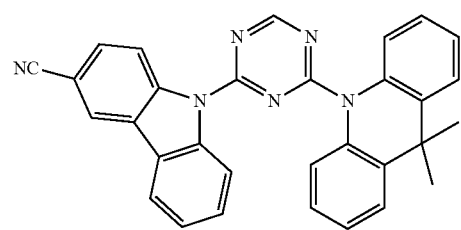
57
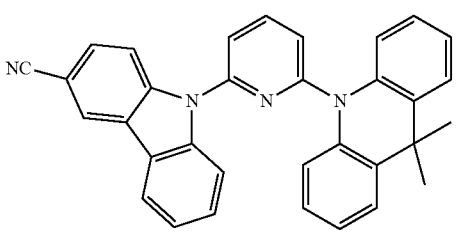
58
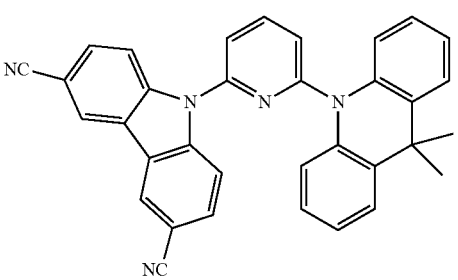
59
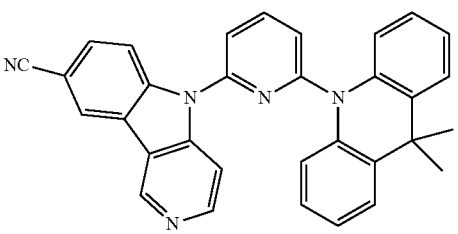
60
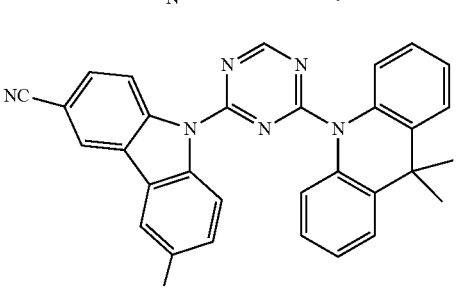
61
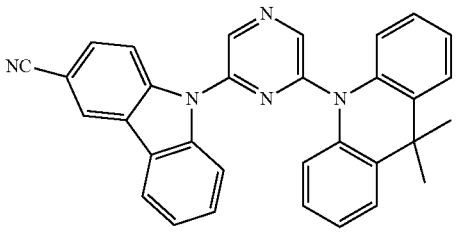
62
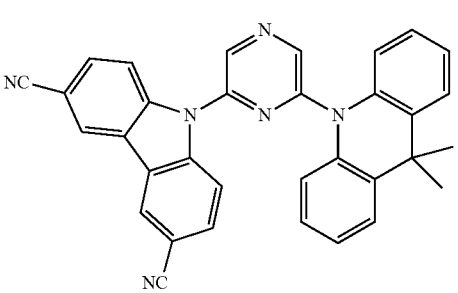

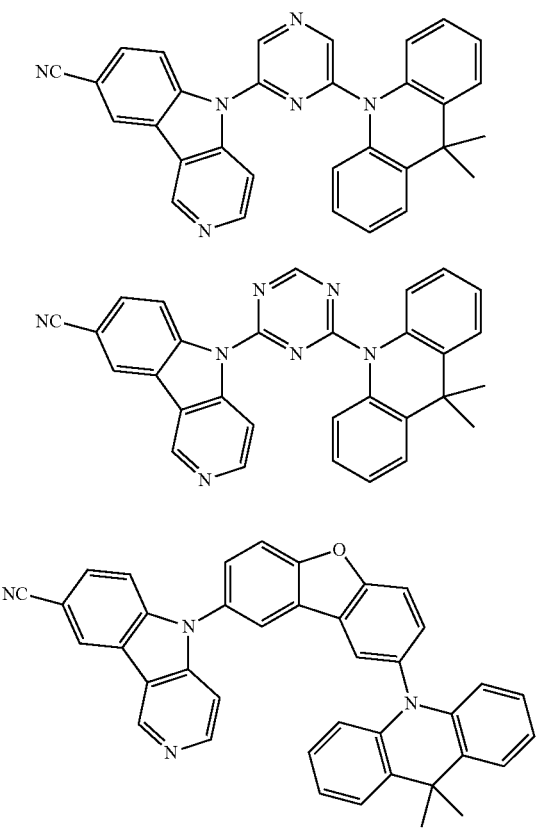
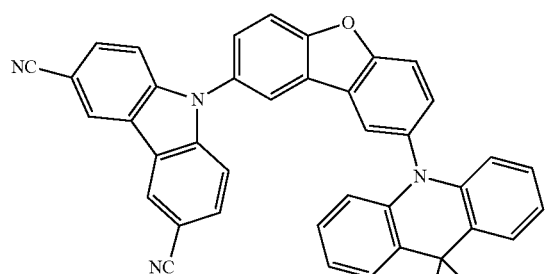
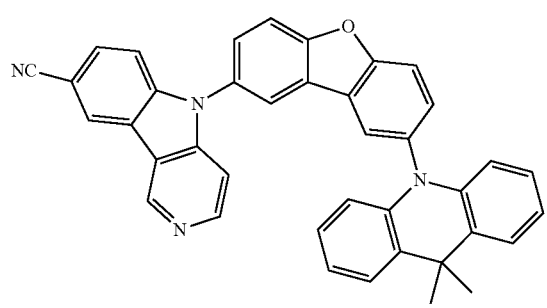
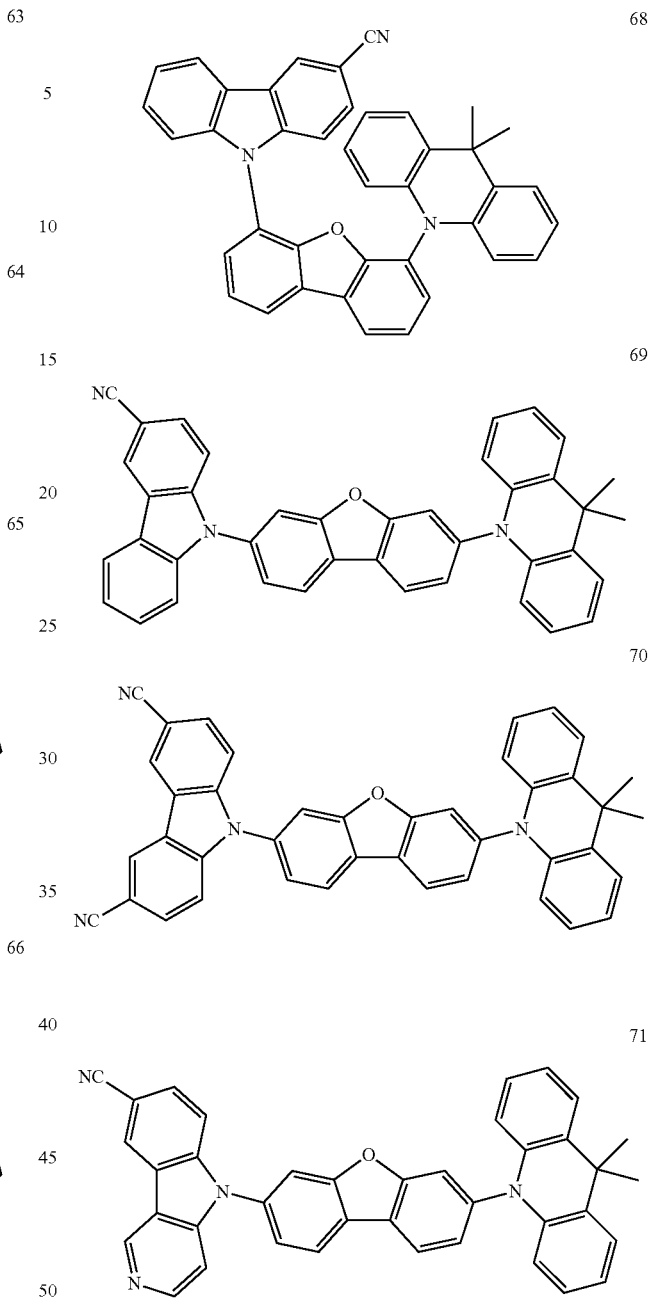
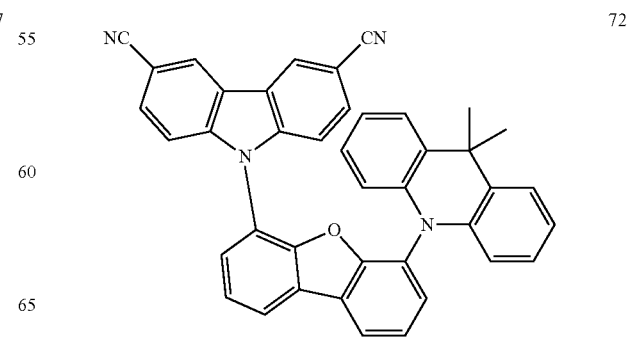

73
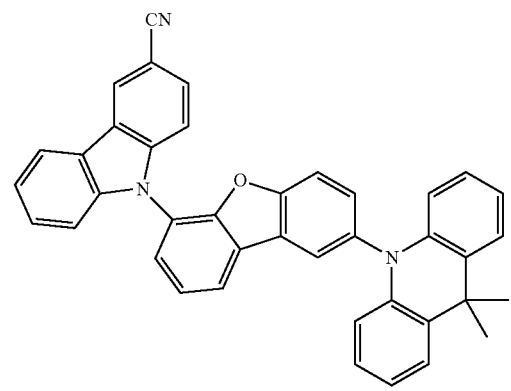
74
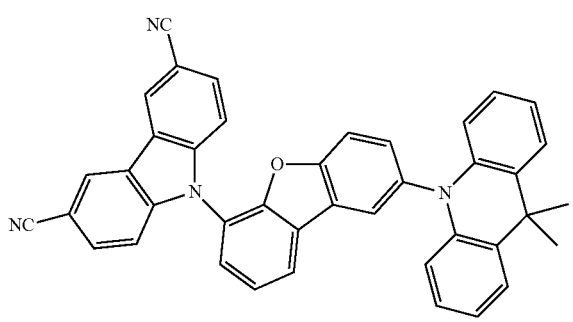
75
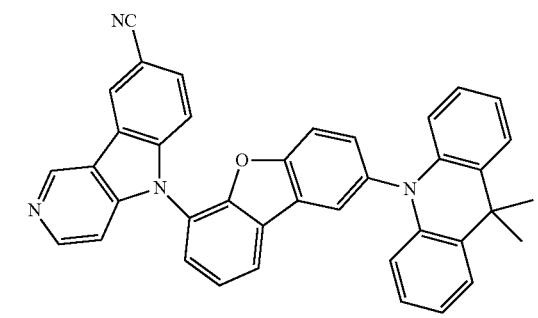
76
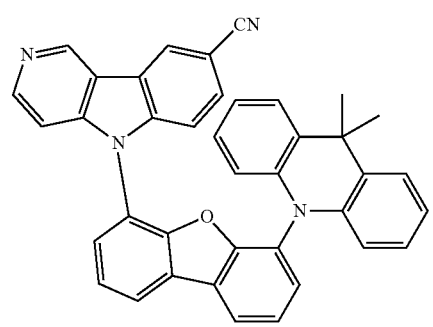
77
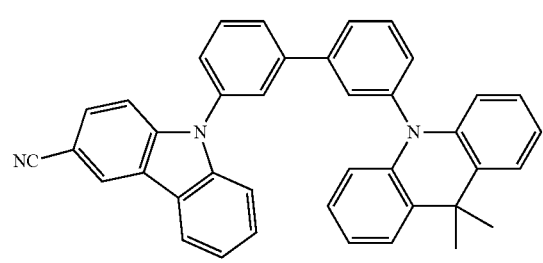
78
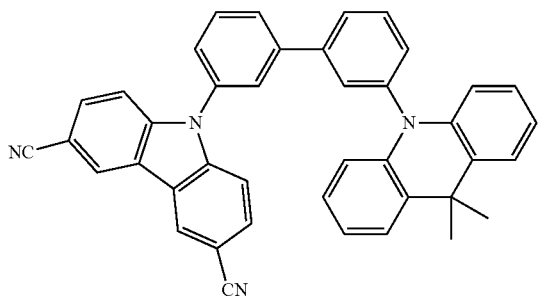
79
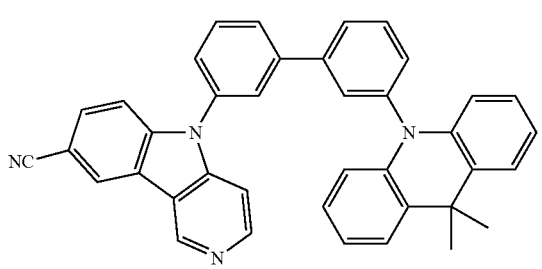
80
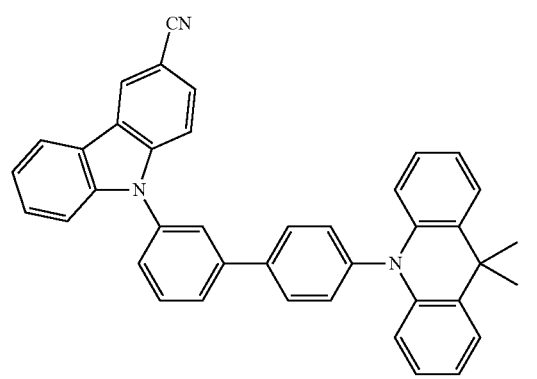
81
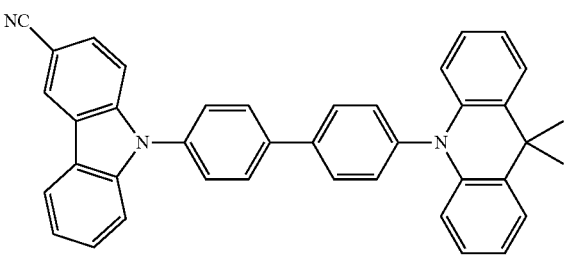
82
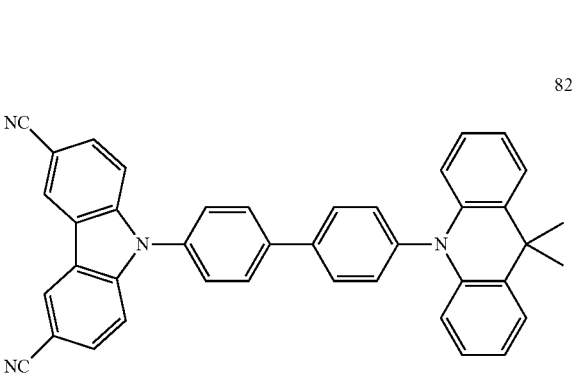

83
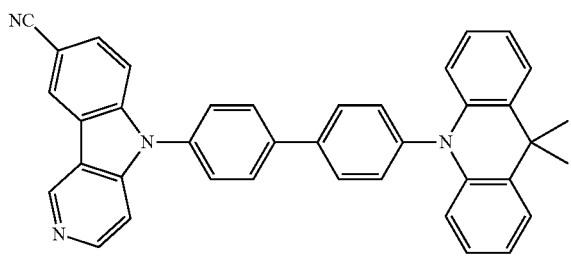
84
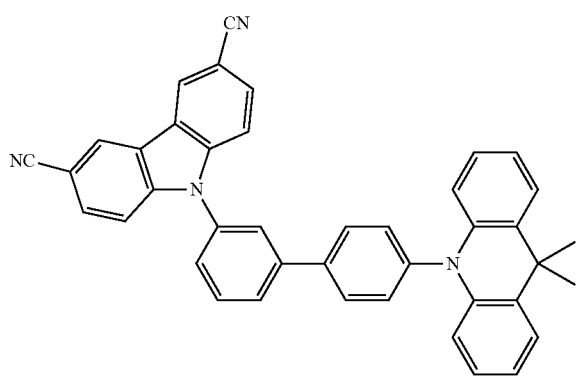
85
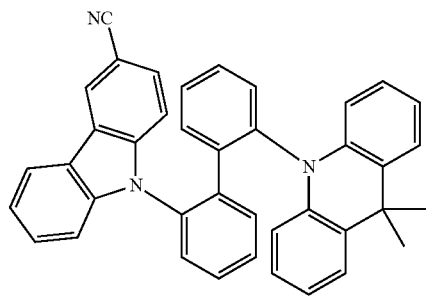
86
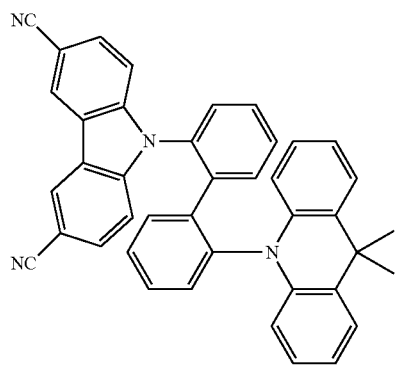
87
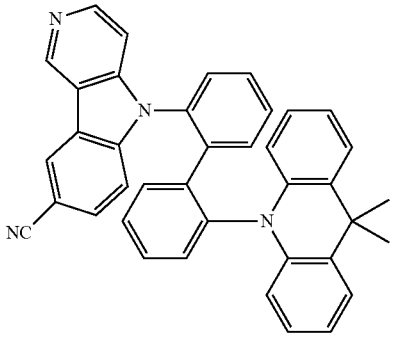
88
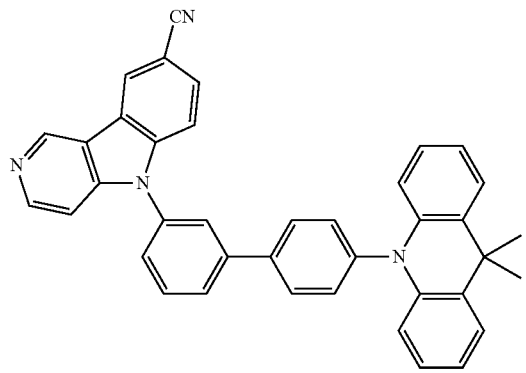
89
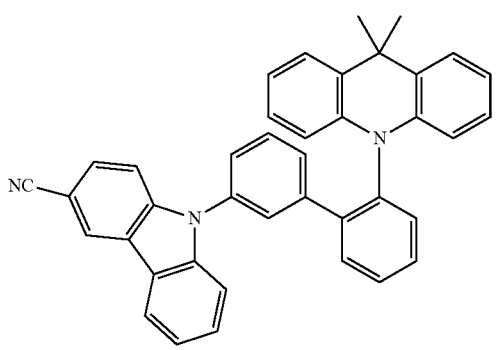
90
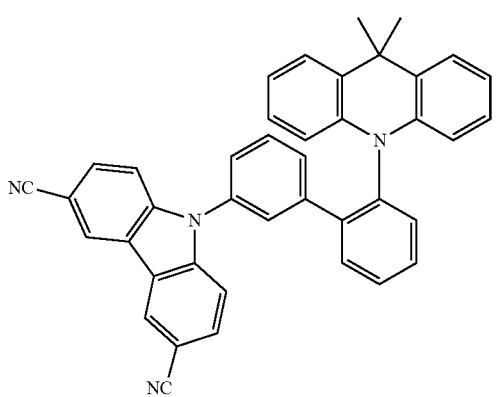

91
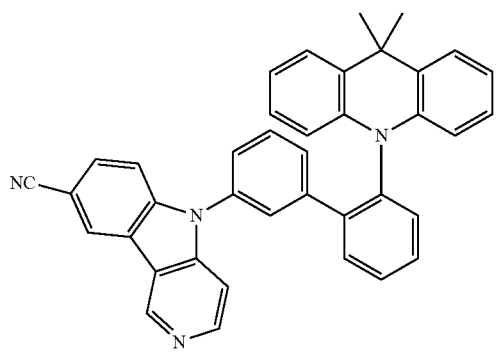
92
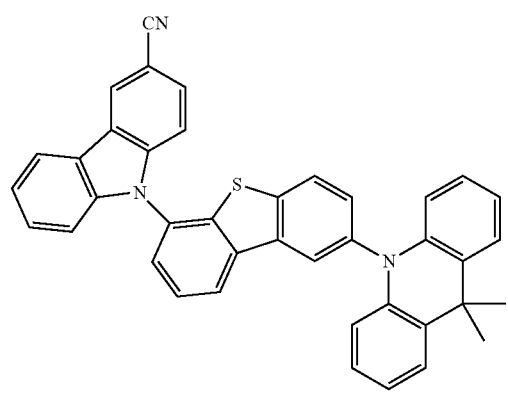
93
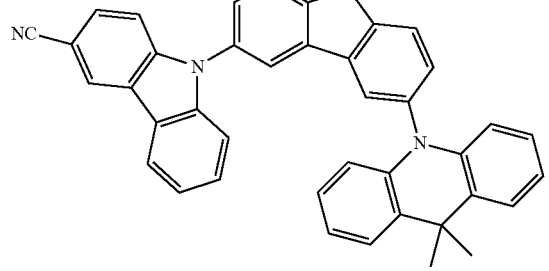
94
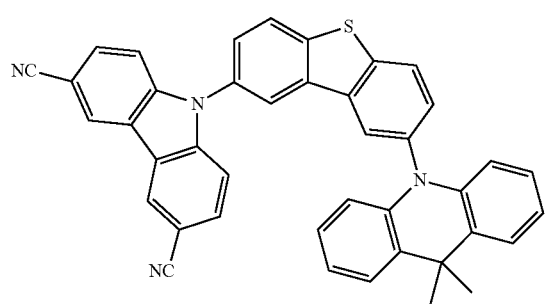
95
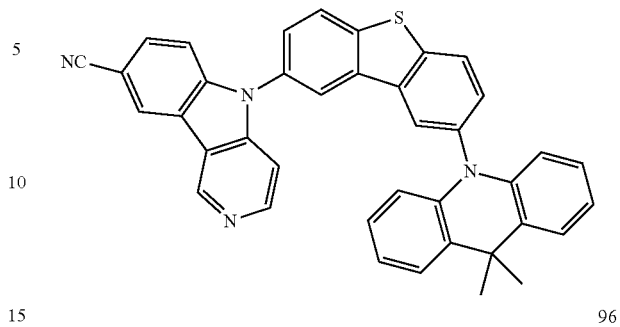
96
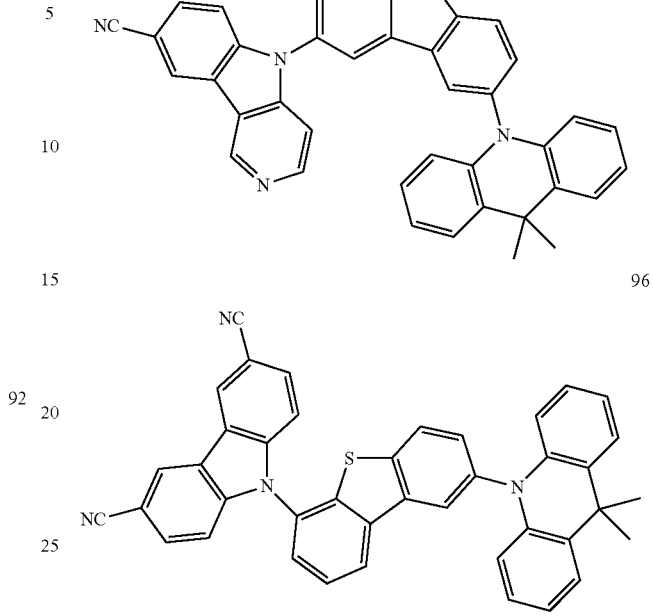
97
98
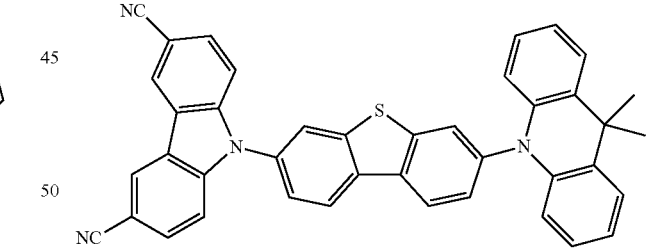
99
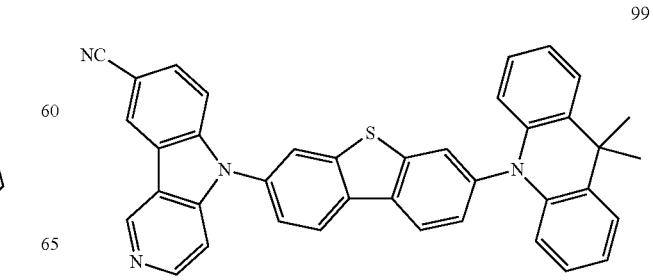

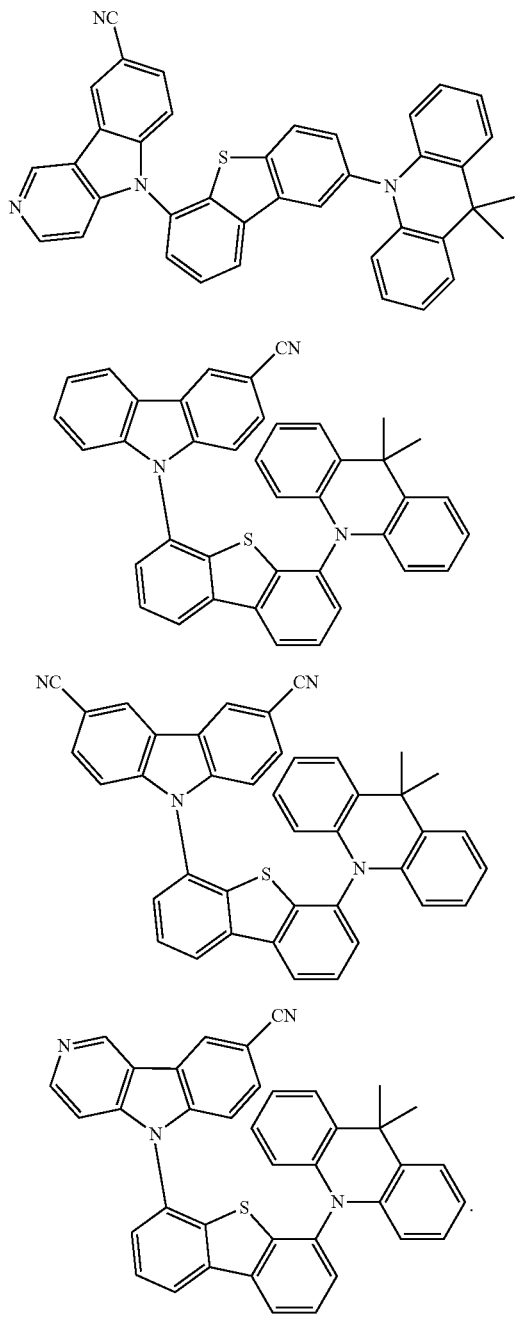

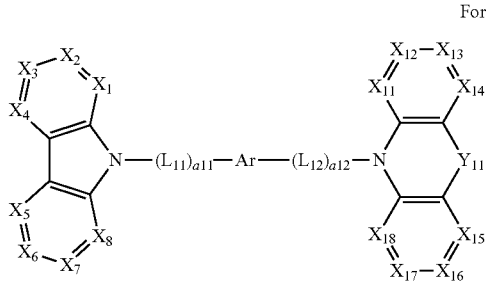

Formula 1

12. An organic light-emitting device comprising:
a first electrode;
a second electrode; and
an organic layer disposed between the first electrode and the second electrode, wherein the organic layer comprises an emission layer and the condensed cyclic compound of Formula 1 of claim 1.

13. The organic light-emitting device of claim 12, wherein the emission layer comprises the condensed cyclic compound of Formula 1.

14. The organic light-emitting device of claim 13, wherein the emission layer further comprises a phosphorescent dopant.

15. The condensed cyclic compound of claim 1, at least one of $X_1$ to $X_8$ in Formula 1 is C(CN); at least one of $X_{11}$ to $X_{18}$ in Formula 1 is C(CN); or $Y_{11}$ in Formula 1 is a group including a cyano (—CN) group.

16. A condensed cyclic compound represented by Formula 1:

wherein, in Formula 1,
$X_1$ is N or $C(R_1)$, $X_2$ is N or $C(R_2)$, $X_3$ is N or $C(R_3)$, $X_4$ is N or $C(R_4)$, $X_5$ is N or $C(R_5)$, $X_6$ is N or $C(R_6)$, $X_7$ is N or $C(R_7)$, $X_8$ is N or $C(R_8)$, $X_{11}$ is N or $C(R_{11})$, $X_{12}$ is N or $C(R_{12})$, $X_{13}$ is N or $C(R_{13})$, $X_{14}$ is N or $C(R_{14})$, $X_{15}$ is N or $C(R_{15})$, $X_{16}$ is N or $C(R_{16})$, $X_{17}$ is N or $C(R_{17})$, and $X_{18}$ is N or $C(R_{18})$,
$Y_{11}$ is $C(R_{101})(R_{102})$ or $Si(R_{101})(R_{102})$,
$R_1$ to $R_8$, $R_{11}$ to $R_{18}$, $R_{101}$, and $R_{102}$ each are independently selected from:
a hydrogen, a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, and —$Si(Q_1)(Q_2)(Q_3)$, wherein the substituted or unsubstituted monovalent non-aromatic condensed heteropolycyclic group does not comprise a substituted or an unsubstituted carbazolyl group,
wherein $R_{101}$ and $R_{102}$ are linked to each other to form a compound represented by Formula 8:

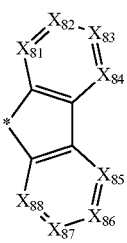

Formula 8 wherein, in Formula 8,

* indicates a carbon atom comprised in $Y_{11}$ of Formula 1,
$X_{81}$ is N or $C(R_{81})$, $X_{82}$ is N or $C(R_{82})$, $X_{83}$ is N or $C(R_{83})$, $X_{84}$ is N or $C(R_{84})$, $X_{85}$ is N or $C(R_{85})$, $X_{86}$ is N or $C(R_{86})$, $X_{87}$ is N or $C(R_{87})$, and $X_{88}$ is N or $C(R_{88})$, $R_{81}$ to $R_{88}$ each are independently selected from a hydrogen, a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —Si$(Q_{31})(Q_{32})(Q_{33})$, and $Q_{31}$ to $Q_{33}$ each are independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, and a triazinyl group, wherein, in Formula 1,
Ar is a group represented by one of Formulae 2A to 2D:

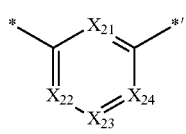

Formula 2A

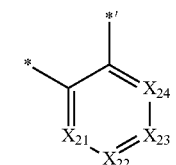

Formula 2B

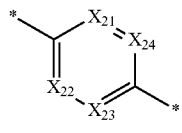

Formula 2C

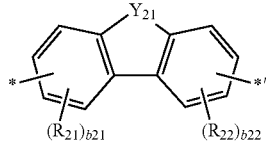

Formula 2D wherein, in Formulae 2A to 2D,
* and *' each independently indicate a binding site to a neighboring atom,
$X_{21}$ is N or $C(R_{21})$, $X_{22}$ is N or $C(R_{22})$, $X_{23}$ is N or $C(R_{23})$, and $X_{24}$ is N or $C(R_{24})$,
$Y_{21}$ is O, S, P(=O)$_2$, Se, $C(R_{25})(R_{26})$, or Si$(R_{25})(R_{26})$,
$R_{21}$ to $R_{26}$ each are independently selected from a hydrogen, a deuterium, a $C_1$-$C_4$ alkyl group, a $C_6$-$C_{20}$ aryl group, a $C_1$-$C_{20}$ heteroaryl group, and —Si$(Q_{11})(Q_{12})(Q_{13})$,
b21 and b22 each are independently selected from integers of 1 to 3, provided that when b21 is 2 or more, groups $R_{21}$ are identical to or different from each other, and provided that when b22 is 2 or more, groups $R_{22}$ are identical to or different from each other, $L_{11}$ and $L_{12}$ each are independently selected from:
a phenylene group, a pyridinylene group, a pyrimidinylene group, a pyrazinylene group, a pyridazinylene group, a triazinylene group, a dibenzofuranylene group, a dibenzothiophenylene group, and a dibenzosilolylene group; and
a phenylene group, a pyridinylene group, a pyrimidinylene group, a pyrazinylene group, a pyridazinylene group, a triazinylene group, a dibenzofuranylene group, a dibenzothiophenylene group, and a dibenzosilolylene group, each substituted with at least one of a deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —Si$(Q_{21})(Q_{22})(Q_{23})$, a11 and a12 each are independently selected from 0, 1, 2, 3, 4, and 5, provided that when a11 is 2 or more, groups $L_{11}$ are identical to or different from each other, and provided that when a12 is 2 or more, groups $L_{12}$ are identical to or different from each other, and $Q_1$ to $Q_3$, $Q_{11}$ to $Q_{13}$, $Q_{21}$ to $Q_{23}$, and $Q_{31}$ to $Q_{33}$ each are independently selected from a hydrogen, a $C_1$-$C_{60}$ alkyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic condensed heteropolycyclic group, provided that the monovalent non-aromatic condensed heteropolycyclic group does not comprise a carbazolyl group, wherein the condensed cyclic compound represented by Formula 1 comprises at least one cyano (—CN) group.

17. A condensed cyclic compound represented by Formula 1:

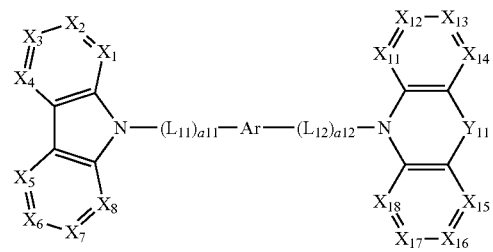

Formula 1 wherein, in Formula 1,
$X_1$ is N or $C(R_1)$, $X_2$ is N or $C(R_2)$, $X_3$ is N or $C(R_3)$, $X_4$ is N or $C(R_4)$, $X_5$ is N or $C(R_5)$, $X_6$ is N or $C(R_6)$, $X_7$ is N or $C(R_7)$, $X_8$ is N or $C(R_8)$, $X_{11}$ is N or $C(R_{11})$, $X_{12}$ is N or $C(R_{12})$, $X_{13}$ is N or $C(R_{13})$, $X_{14}$ is N or $C(R_{14})$, $X_{15}$ is N or $C(R_{15})$, $X_{16}$ is N or $C(R_{16})$, $X_{17}$ is N or $C(R_{17})$, and $X_{18}$ is N or $C(R_{18})$,
$Y_{11}$ is $C(R_{101})(R_{102})$ or Si$(R_{101})(R_{102})$,
$R_1$ to $R_8$, $R_{11}$ to $R_{18}$, $R_{101}$, and $R_{102}$ each are independently selected from:
a hydrogen, a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$), wherein the substituted or unsubstituted monovalent non-aromatic condensed heteropolycyclic group does not comprise a substituted or an unsubstituted carbazolyl group, wherein at least one of $a_{11}$ and $a_{12}$ is not 0, and $L_{11}$ and $L_{12}$ each are independently selected from:

a phenylene group, a pyridinylene group, a pyrimidinylene group, a pyrazinylene group, a pyridazinylene group, a triazinylene group, a dibenzofuranylene group, and a dibenzothiophenylene group; and a phenylene group, a pyridinylene group, a pyrimidinylene group, a pyrazinylene group, a pyridazinylene group, a triazinylene group, a dibenzofuranylene group, and a dibenzothiophenylene group, each substituted with at least one of a deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —Si($Q_{21}$)($Q_{22}$)($Q_{23}$), wherein, in Formula 1, Ar is a group represented by one of Formulae 2A to 2D:

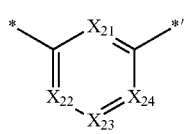

Formula 2A

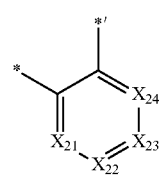

Formula 2B

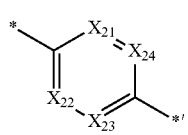

Formula 2C

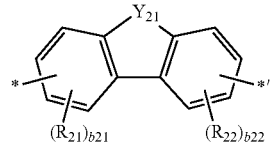

Formula 2D wherein, in Formulae 2A to 2D,

* and *' each independently indicate a binding site to a neighboring atom, $X_{21}$ is N or C($R_{21}$), $X_{22}$ is N or C($R_{22}$), $X_{23}$ is N or C($R_{23}$), and $X_{24}$ is N or C($R_{24}$), $Y_{21}$ is O, S, P(=O)$_2$, Se, C($R_{25}$)($R_{26}$), or Si($R_{25}$)($R_{26}$), $R_{21}$ to $R_{26}$ each are independently selected from a hydrogen, a deuterium, a $C_1$-$C_4$ alkyl group, a $C_6$-$C_{20}$ aryl group, a $C_1$-$C_{20}$ heteroaryl group, and —Si($Q_{11}$)($Q_{12}$)($Q_{13}$), b21 and b22 each are independently selected from integers of 1 to 3, provided that when b21 is 2 or more, groups $R_{21}$ are identical to or different from each other, and provided that when b22 is 2 or more, groups $R_{22}$ are identical to or different from each other, $L_{11}$ and $L_{12}$ each are independently selected from:

a phenylene group, a pyridinylene group, a pyrimidinylene group, a pyrazinylene group, a pyridazinylene group, a triazinylene group, a dibenzofuranylene group, a dibenzothiophenylene group, and a dibenzosilolylene group; and a phenylene group, a pyridinylene group, a pyrimidinylene group, a pyrazinylene group, a pyridazinylene group, a triazinylene group, a dibenzofuranylene group, a dibenzothiophenylene group, and a dibenzosilolylene group, each substituted with at least one of a deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —Si($Q_{21}$)($Q_{22}$)($Q_{23}$), a11 and a12 each are independently selected from 0, 1, 2, 3, 4, and 5, provided that when a11 is 2 or more, groups $L_{11}$ are identical to or different from each other, and provided that when a12 is 2 or more, groups $L_{12}$ are identical to or different from each other, and $Q_1$ to $Q_3$, $Q_{11}$ to $Q_{13}$, $Q_{21}$ to $Q_{23}$, and $Q_{31}$ to $Q_{33}$ each are independently selected from a hydrogen, a $C_1$-$C_{60}$ alkyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic condensed heteropolycyclic group, provided that the monovalent non-aromatic condensed heteropolycyclic group does not comprise a carbazolyl group, wherein the condensed cyclic compound represented by Formula 1 comprises at least one cyano (—CN) group.

18. The condensed cyclic compound of claim 17, wherein at least one of $a_{11}$ and $a_{12}$ is not 0, and $L_{11}$ and $L_{12}$ each are independently selected from:

a phenylene group, a pyridinylene group, a pyrimidinylene group, and a triazinylene group; and a phenylene group, a pyridinylene group, a pyrimidinylene group, and a triazinylene group, each substituted with at least one of a deuterium, a methyl group, an ethyl group, an n-propyl group, an iso-propyl group, an n-butyl group, an isobutyl group, a sec-butyl group, a tert-butyl group, a phenyl group, a pyridinyl group, a pyrimidinyl group, a pyrazinyl group, a pyridazinyl group, a triazinyl group, and —Si($Q_{21}$)($Q_{22}$)($Q_{23}$).

19. A condensed cyclic compound represented by one of Formulae 1-21 to 1-47:

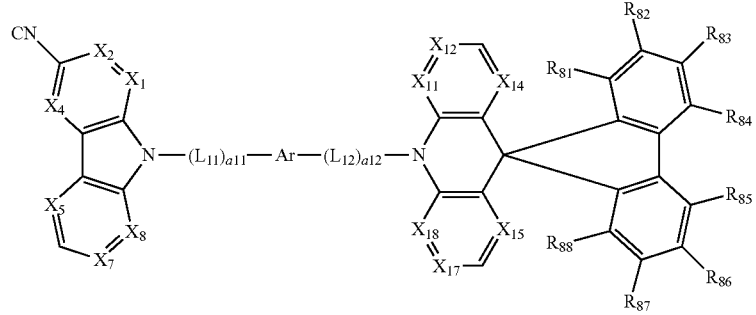

1-21

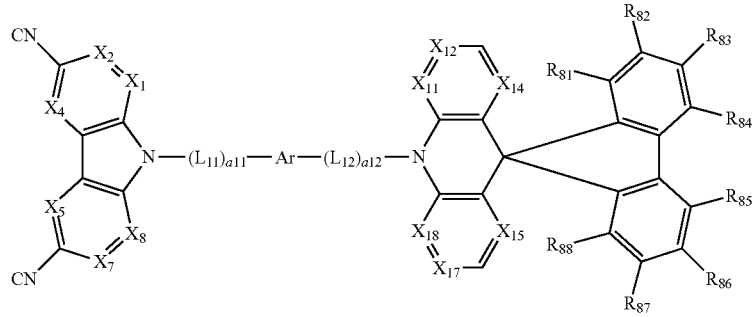

1-22

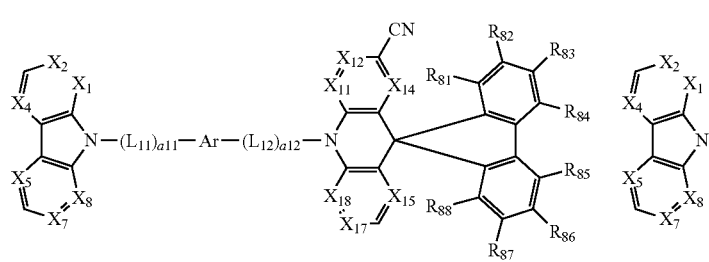

1-23

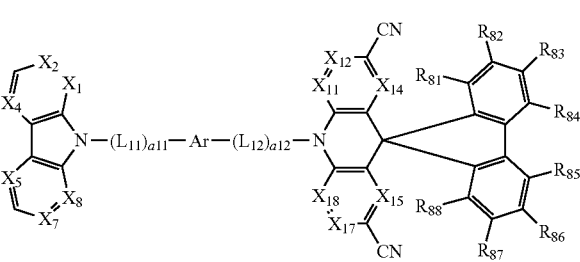

1-24

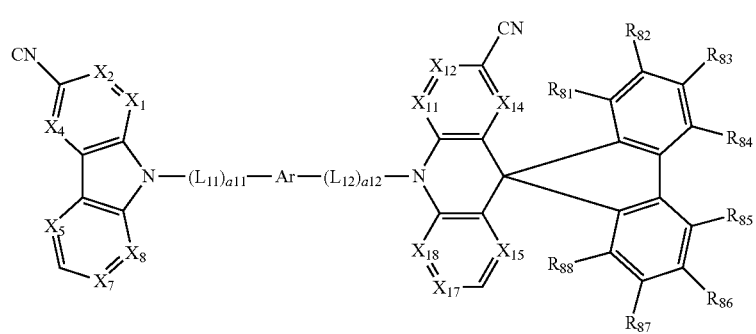

1-25

-continued
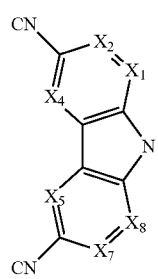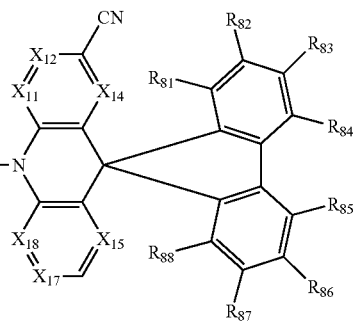
1-26
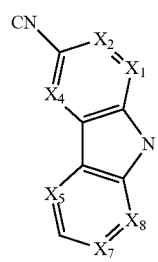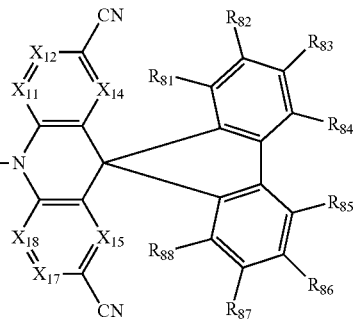
1-27
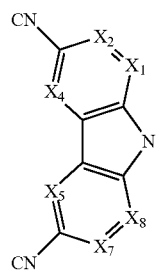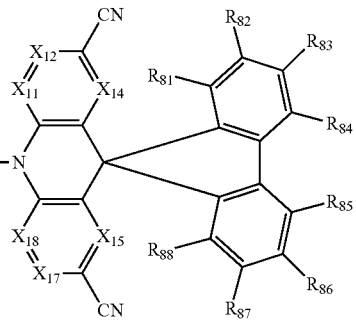
1-28
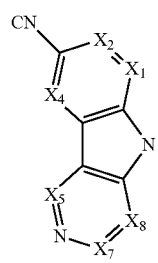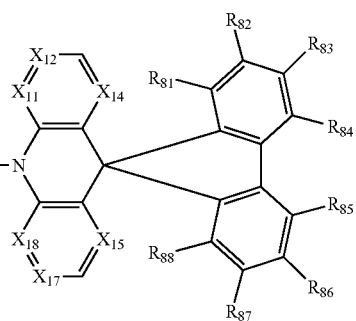
1-29
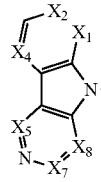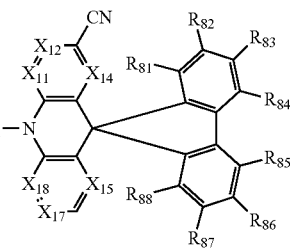
1-30
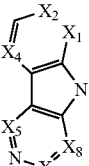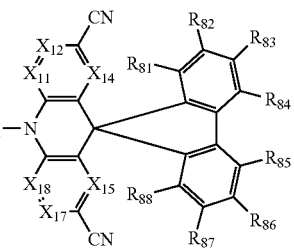
1-31

-continued
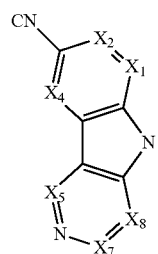 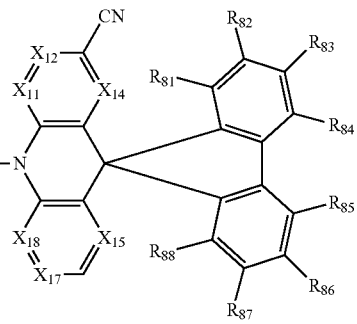
1-32
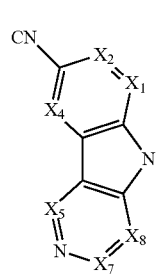 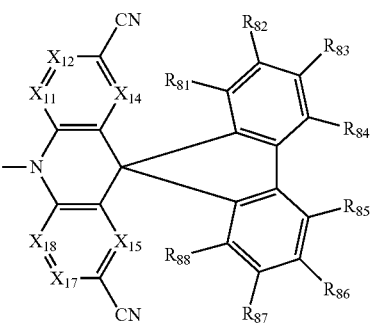
1-33
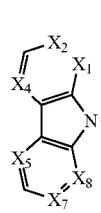 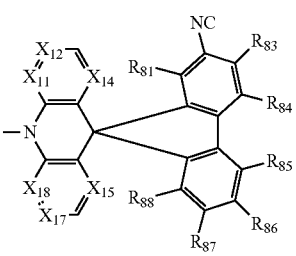 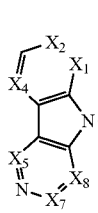 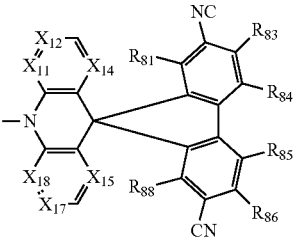
1-34                                           1-35
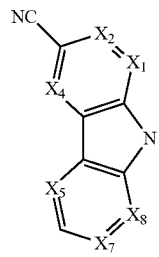 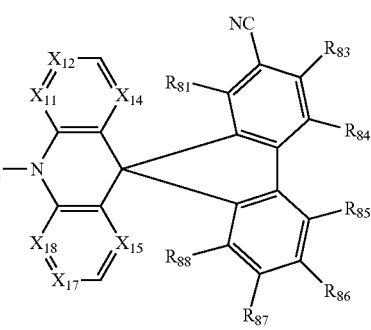
1-36
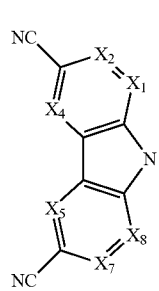 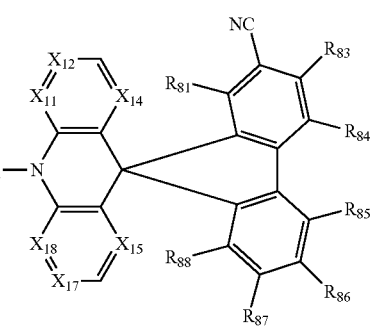
1-37

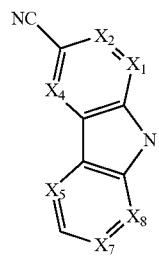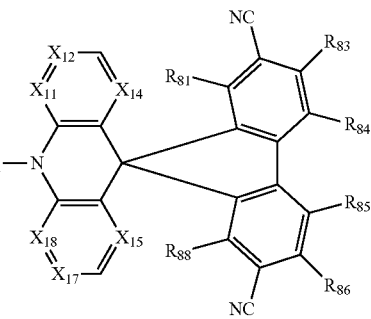
1-38
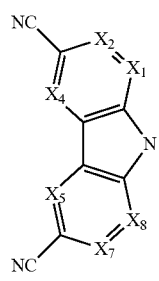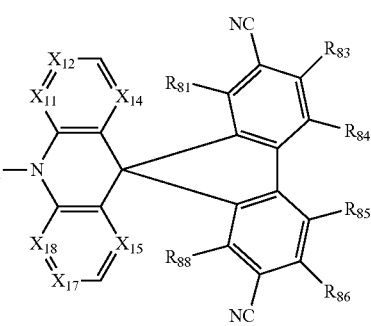
1-39
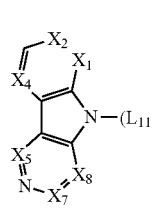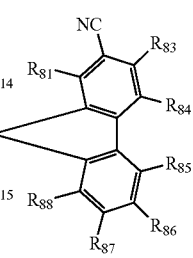
1-40
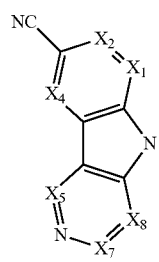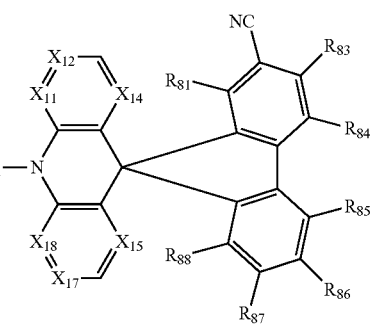
1-41
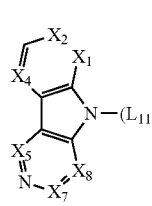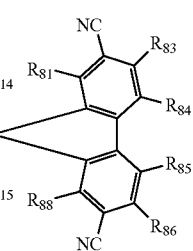
1-42

-continued

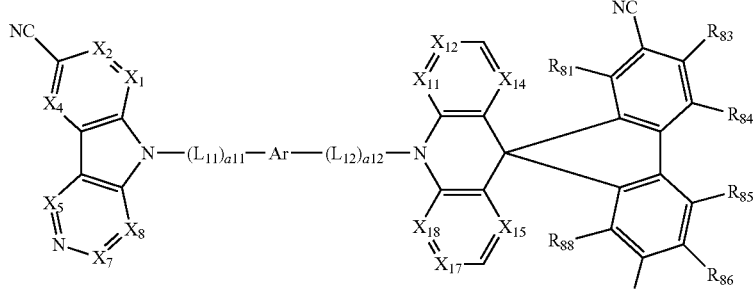

1-43

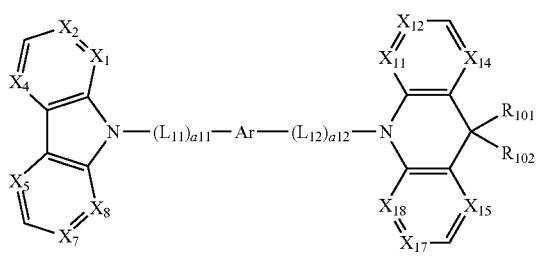

1-44

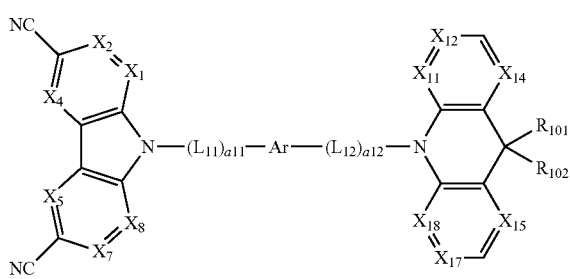

1-45

1-46

1-47 wherein, in Formulae 1-21 to 1-47, $X_1$ is N or $C(R_1)$, $X_2$ is N or $C(R_2)$, $X_4$ is N or $C(R_4)$, $X_5$ is N or $C(R_5)$, $X_7$ is N or $C(R_7)$, $X_8$ is N or $C(R_8)$, $X_{11}$ is N or $C(R_{11})$, $X_{12}$ is N or $C(R_{12})$, $X_{14}$ is N or $C(R_{14})$, $X_{15}$ is N or $C(R_{15})$, $X_{17}$ is N or $C(R_{17})$, and $X_{18}$ is N or $C(R_{18})$, $R_1$, $R_2$, $R_4$, $R_5$, $R_7$, $R_8$, $R_{11}$, $R_{12}$, $R_{14}$, $R_{15}$, $R_{17}$, $R_{18}$ each are independently selected from:

a hydrogen, a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, and —Si$(Q_1)(Q_2)(Q_3)$, wherein the substituted or unsubstituted monovalent non-aromatic condensed heteropolycyclic group does not comprise a substituted or an unsubstituted carbazolyl group, Ar is a group represented by one of Formulae 2A to 2D:

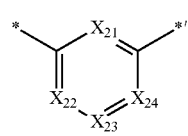

Formula 2A

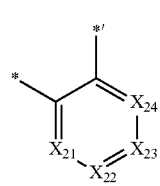

Formula 2B

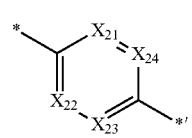

Formula 2C

165

-continued

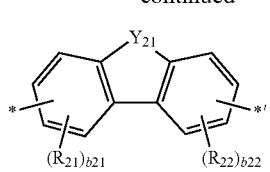

Formula 2D wherein, in Formulae 2A to 2D,
* and *' each independently indicate a binding site to a neighboring atom,
$X_{21}$ is N or $C(R_{21})$, $X_{22}$ is N or $C(R_{22})$, $X_{23}$ is N or $C(R_{23})$, and $X_{24}$ is N or $C(R_{24})$,
$Y_{21}$ is O, S, P(=O)$_2$, Se, $C(R_{25})(R_{26})$, or $Si(R_{25})(R_{26})$,
$R_{21}$ to $R_{26}$ each are independently selected from a hydrogen, a deuterium, a $C_1$-$C_4$ alkyl group, a $C_6$-$C_{20}$ aryl group, a $C_1$-$C_{20}$ heteroaryl group, and —$Si(Q_{11})(Q_{12})(Q_{13})$,
b21 and b22 each are independently selected from integers of 1 to 3, provided that when b21 is 2 or more, groups $R_{21}$ are identical to or different from each other, and provided that when b22 is 2 or more, groups $R_{22}$ are identical to or different from each other,
$L_{11}$ and $L_{12}$ each are independently selected from:
a phenylene group, a pyridinylene group, a pyrimidinylene group, a pyrazinylene group, a pyridazinylene group, a triazinylene group, a dibenzofuranylene group, a dibenzothiophenylene group, and a dibenzosilolylene group; and
a phenylene group, a pyridinylene group, a pyrimidinylene group, a pyrazinylene group, a pyridazinylene group, a triazinylene group, a dibenzofuranylene group, a dibenzothiophenylene group, and a dibenzosilolylene group, each substituted with at least one of a deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —$Si(Q_{21})(Q_{22})(Q_{23})$,
a11 and a12 each are independently selected from 0, 1, 2, 3, 4, and 5, provided that when a11 is 2 or more, groups $L_{11}$ are identical to or different from each other, and provided that when a12 is 2 or more, groups $L_{12}$ are identical to or different from each other, and
$Q_1$ to $Q_3$, $Q_{11}$ to $Q_{13}$, $Q_{21}$ to $Q_{23}$, and $Q_{31}$ to $Q_{33}$ each are independently selected from a hydrogen, a $C_1$-$C_{60}$ alkyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic condensed heteropolycyclic group, provided that the monovalent non-aromatic condensed heteropolycyclic group does not comprise a carbazolyl group,
wherein the condensed cyclic compound represented by one of Formulae 1-44 comprises at least one cyano (—CN) group,
$R_{81}$ to $R_{88}$ each are independently selected from a hydrogen, a deuterium, —F, —Cl, —Br, —I, a hydroxyl group, a cyano (—CN) group, a nitro group, an amino group, an amidino group, a hydrazine group, a hydra-

166 zone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —$Si(Q_{31})(Q_{32})(Q_{33})$,
$Q_{31}$ to $Q_{33}$ each are independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, and a triazinyl group, and
$R_{101}$ and $R_{102}$ each are independently selected from:
a methyl group, an ethyl group, an n-propyl group, an iso-propyl group, an n-butyl group, an isobutyl group, a sec-butyl group, a tert-butyl group, a phenyl group, and a naphthyl group; and
a methyl group, an ethyl group, an n-propyl group, an iso-propyl group, an n-butyl group, an isobutyl group, a sec-butyl group, a tert-butyl group, a phenyl group, and a naphthyl group, each substituted with a cyano (—CN) group.

20. A condensed cyclic compound represented by Formula 1:

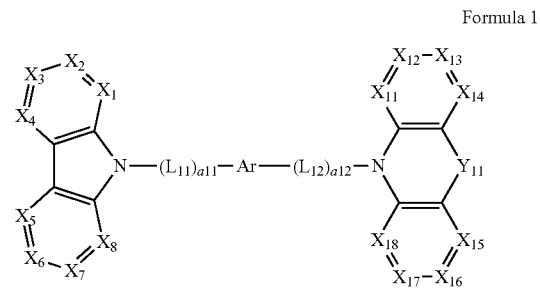

Formula 1 wherein, in Formula 1,
$X_1$ is N or $C(R_1)$, $X_2$ is N or $C(R_2)$, $X_3$ is N or $C(R_3)$, $X_4$ is N or $C(R_4)$, $X_5$ is N or $C(R_5)$, $X_6$ is N or $C(R_6)$, $X_7$ is N or $C(R_7)$, $X_8$ is N or $C(R_8)$, $X_{11}$ is N or $C(R_{11})$, $X_{12}$ is N or $C(R_{12})$, $X_{13}$ is N or $C(R_{13})$, $X_{14}$ is N or $C(R_{14})$, $X_{15}$ is N or $C(R_{15})$, $X_{16}$ is N or $C(R_{16})$, $X_{17}$ is N or $C(R_{17})$, and $X_{18}$ is N or $C(R_{18})$,
$Y_{11}$ is $C(R_{101})(R_{102})$ or $Si(R_{101})(R_{102})$,
$R_{11}$ to $R_{18}$, $R_{101}$, and $R_{102}$ each are independently selected from:
a hydrogen, a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$), wherein the substituted or unsubstituted monovalent non-aromatic condensed heteropolycyclic group does not comprise a substituted or an unsubstituted carbazolyl group, $R_1$ to $R_8$ each are independently selected from a hydrogen, a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$), wherein the substituted or unsubstituted monovalent non-aromatic condensed heteropolycyclic group does not comprise a substituted or an unsubstituted carbazolyl group, wherein at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_6$ arylthio group, the substituted $C_2$-$C_{60}$ heteroaryl group, the substituted monovalent non-aromatic condensed polycyclic group, and the substituted monovalent non-aromatic condensed heteropolycyclic group is selected from a deuterium, —F, —Cl, —Br, —I, a hydroxyl group, a cyano (—CN) group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a monovalent non-aromatic condensed polycyclic group, a monovalent non-aromatic condensed heteropolycyclic group, and —Si($Q_{31}$)($Q_{32}$)($Q_{33}$), wherein $Q_1$ to $Q_3$, $Q_{11}$ to $Q_{13}$, $Q_{21}$ to $Q_{23}$, and $Q_{31}$ to $Q_{33}$ are each independently selected from a hydrogen, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, wherein, in Formula 1, Ar is a group represented by one of Formulae 2A to 2D:

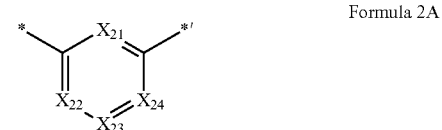

Formula 2A

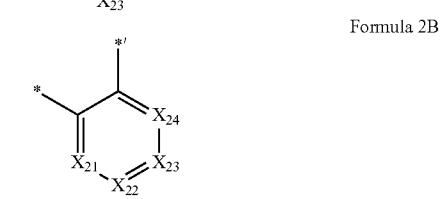

Formula 2B

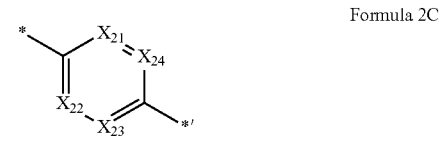

Formula 2C

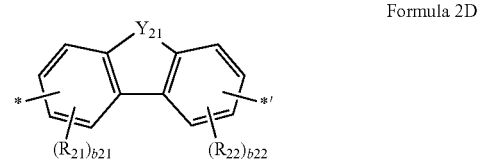

Formula 2D wherein, in Formulae 2A to 2D,

* and *' each independently indicate a binding site to a neighboring atom, $X_{21}$ is N or C($R_{21}$), $X_{22}$ is N or C($R_{22}$), $X_{23}$ is N or C($R_{23}$), and $X_{24}$ is N or C($R_{24}$), $Y_{21}$ is O, S, P(=O)$_2$, Se, C($R_{25}$)($R_{26}$), or Si($R_{25}$)($R_{26}$), $R_{21}$ to $R_{26}$ each are independently selected from a hydrogen, a deuterium, a $C_1$-$C_4$ alkyl group, a $C_6$-$C_{20}$ aryl group, a $C_1$-$C_{20}$ heteroaryl group, and —Si($Q_{11}$)($Q_{12}$)($Q_{13}$), b21 and b22 each are independently selected from integers of 1 to 3, provided that when b21 is 2 or more, groups $R_{21}$ are identical to or different from each other, and provided that when b22 is 2 or more, groups $R_{22}$ are identical to or different from each other, $L_{11}$ and $L_{12}$ each are independently selected from:

a phenylene group, a pyridinylene group, a pyrimidinylene group, a pyrazinylene group, a pyridazinylene group, a triazinylene group, a dibenzofuranylene group, a dibenzothiophenylene group, and a dibenzosilolylene group; and a phenylene group, a pyridinylene group, a pyrimidinylene group, a pyrazinylene group, a pyridazinylene group, a triazinylene group, a dibenzofuranylene group, a dibenzothiophenylene group, and a dibenzosilolylene group, each substituted with at least one of a deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and $-Si(Q_{21})(Q_{22})(Q_{23})$, a11 and a12 each are independently selected from 0, 1, 2, 3, 4, and 5, provided that when a11 is 2 or more, groups $L_{11}$ are identical to or different from each other, and provided that when a12 is 2 or more, groups $L_{12}$ are identical to or different from each other, and $Q_1$ to $Q_3$, $Q_{11}$ to $Q_{13}$, $Q_{21}$ to $Q_{23}$, and $Q_{31}$ to $Q_{33}$ each are independently selected from a hydrogen, a $C_1$-$C_{60}$ alkyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic condensed heteropolycyclic group, provided that the monovalent non-aromatic condensed heteropolycyclic group does not comprise a carbazolyl group, wherein the condensed cyclic compound represented by Formula 1 comprises at least one cyano (—CN) group.

* * * * *